United States Patent
Raineri et al.

(10) Patent No.: US 10,414,807 B2
(45) Date of Patent: Sep. 17, 2019

(54) **TRANSCRIPTION FACTOR GENES AND PROTEINS FROM *HELIANTHUS ANNUUS*, AND TRANSGENIC PLANTS INCLUDING THE SAME**

(71) Applicants: Consejo Nacional De Investigaciones Cientificas Y Tecnicas, Buenos Aires (AR); Universidad Nacional Del Litoral, Santa Fe (AR)

(72) Inventors: Jesica Raineri, Santa Fe (AR); Raquel Lia Chan, Santa Fe (AR); Jorge Giacomelli, Santa Fe (AR)

(73) Assignees: CONSEJO NACIONAL DE INVESTIGACIONES CIENTIFICAS Y TECNICAS, Buenos Aires (AR); UNIVERSIDAD NACIONAL DEL LITORAL, Santa Fe (AR)

( * ) Notice: Subject to any disclaimer, the term of this patent is extended or adjusted under 35 U.S.C. 154(b) by 27 days.

(21) Appl. No.: 15/307,333

(22) PCT Filed: Apr. 30, 2015

(86) PCT No.: PCT/GB2015/051269
§ 371 (c)(1),
(2) Date: Oct. 27, 2016

(87) PCT Pub. No.: WO2015/166256
PCT Pub. Date: Nov. 5, 2015

(65) Prior Publication Data
US 2017/0044221 A1  Feb. 16, 2017

Related U.S. Application Data

(60) Provisional application No. 61/986,730, filed on Apr. 30, 2014.

(51) Int. Cl.
*C12N 15/82* (2006.01)
*C07K 14/415* (2006.01)

(52) U.S. Cl.
CPC ........ *C07K 14/415* (2013.01); *C12N 15/8261* (2013.01); *C12N 15/8271* (2013.01); *C12N 15/8273* (2013.01); *C12N 15/8279* (2013.01); *Y02A 40/146* (2018.01)

(58) Field of Classification Search
None
See application file for complete search history.

(56) References Cited

U.S. PATENT DOCUMENTS

2010/0263093 A1* 10/2010 Chen .................... C07K 14/415
800/298

OTHER PUBLICATIONS

Sequence Accession GE487953, Nov. 3, 2008, attached as a sequence alignment in the Office Action (Year: 2008).*
Brivanlou, et al., "Signal Transduction and the Control of Gene Expression," Science Compass Review (or online at http://science.sciencemag.org/content/295/5556/813), vol. 295, pp. 813-818, published Feb. 1, 2002.
Ciolkowski, et al., "Studies on DNA-Binding Selectivity of WRKY Transcription Factors Lend Structural Clues into WRKY—Domain Function," Plant Mol Biol (2008), vol. 68, pp. 81-92, published Jun. 4, 2008.
Eulgem, et al., "Networks of WRKY Transcription Factors in Defense Signaling," ScienceDirect, vol. 10, pp. 366-371. Apr. 20, 2007.
Giacomelli, et al., "Expression Analyses Indicate the Involvement of Sunflower WRKY Transcription Factors in Stress Responses, and Phylogenetic Reconstructions Reveal the Existnce of a Novel Clade in the Asteraceae," Plant Science, vol. 178 (2010), pp. 398-410. Available online Feb. 17, 2010.
Giacomelli, "Thesis on Caracterización Funcional de Genes de Girasol Que Codifican Factores de Transcripción de la Familia WRKY. HaWRKY6 y su Regulación por el MicroRNA396," Universidad Nacional Del Litoral (English translation of Abstract provided), 2012.
Giacomelli, "Role of Recently Evolved miRNA Regulation of Sunflower HaWRKY6 in Response to Temperature Damage," New Phytologist Research Report, (2012) vol. 195, pp. 766-773, Accepted Jul. 2, 2012.
Peng et al., "Letters to Nature," Nature vol. 400, pp. 256-261, published Jul. 15, 1999.
Peng et al., "The *Arabidopsis* GAI Gene Defines a Signaling Pathway that Negatively Regulates Gibberellin Responses," Genes & Development, vol. 11, pp. 3194-3205, revised version accepted Sep. 17, 1997.
Rushton et al., "WRKY Transcription Factors," Trends in Plant Science, vol. 15, No. 5, pp. 247-258, available online Mar. 19, 2010.

* cited by examiner

*Primary Examiner* — Elizabeth F McElwain
(74) *Attorney, Agent, or Firm* — McKee, Voorhees & Sease, PLC

(57) ABSTRACT

A polynucleotide having at least 80% sequence identity with the full-length nucleotide sequence of SEQ ID NO: 1 and substantially identical polynucleotides; an isolated polypeptide having at least 80% sequence identity with the full-length amino acid sequence of SEQ ID NO: 2 and substantially identical polypeptides; and polynucleotides encoding the Ha WRKY76 polypeptide and substantially identical polypeptides are described. Also described are vectors and recombinant expression cassettes containing the c DNA polynucleotide, a polynucleotide encoding the Ha WRKY76 polypeptide, or substantially identical polynucleotides. Transgenic plants containing such expression cassettes, related methods and uses are also provided.

34 Claims, 33 Drawing Sheets
Specification includes a Sequence Listing.

Fig. 1

```
HaWKRY76      MAVDFVGIQSTDHLLNRMFQLLSHDLNVSSTYTHAVSAFKRTGHARFRRGPSSTTGDTNG

HaT13|007971  MAVDFVGIQSTDHLLNRMFQLLSHDLNVSSTYTHAVSAFKRTGHARFRRGPSSTTGDTNG
              ************************************************************

HaWKRY76      PSTSSHSEGKSRDTTSFVQNECFSNKPVTEITTTTTSTSSSSVVSSSTGGNLDGSVSNGK

HaT13|007971  PSTSSHSEGKSRDTTSFVQNECFSNKSVTEITTTTTSTSSSSVVSSSTGGNLDGSVSNGK
              *************************.**********************************

HaWKRY76      QFSSLGIVAPAPTFSSRKPPLPSTHRKRCGADRPVASVHGSGSGCHCCSKRRKTGSKREI

HaT13|007971  QFSSLGIVAPAPTFSSRKPPLPSTHRKRCGADRPVASVHGSGSGCHCCSKRRKTGSKREI
              ************************************************************

HaWKRY76      RRVPITGSKITSIPADDYSWKKYGEKKIDGSLYPRVYYKCITGKGCPARKRVELSADDSK

HaT13|007971  RRVPITGSKITSIPADDYSWKKYGEKKIDGSLYPRVYYKCITGKGCPARKRVELSADDSK
              ************************************************************

HaWKRY76      MLIVTYDGEHRHRDRHAPVPMSLTGVYGEPK
HaT13|007971  MLIVTYDGEHRHRDRHAPVPMSLTGVYGESK
              ***************************** *
```

Fig. 2A

| | |
|---|---|
| HaWKRY76 | atggcggttgatttcgtcggaattcaatctaccgatcatcttctaaaccgcatgttccag |
| HaT13\|007971 | atggcggttgatttcgtcggaattcaatctaccgatcatcttctaaaccgcatgttccag |
| | ************************************************************ |
| HaWKRY76 | ttattaagtcacgatttaaacgtttcgtcaacctacacgcacgcggtttctgctttcaaa |
| HaT13\|007971 | ttattaagtcacgatttaaacgtttcgtcaacctacacgcacgcggtttctgctttcaaa |
| | ************************************************************ |
| HaWKRY76 | cgcaccggtcacgcacggttccgccgtggaccgtcgtctaccaccggagacactaacgga |
| HaT13\|007971 | cgcaccggtcacgcacggttccgccgtggaccgtcgtctaccaccggagacactaacgga |
| | ************************************************************ |
| HaWKRY76 | ccttcaacttcttcacattcggaaggtaaatcacgagatgcgacttcgtttgtacaaaac |
| HaT13\|007971 | ccttcaacttcttcacattcggaaggtaaatcacgagatacgacttcgtttgtacaaaac |
| | ****************************************.*************** |
| HaWKRY76 | gagtgtttttcaaacaaaccggtgacggagataacgacgacgacgacgtcaacgagctcg |
| HaT13\|007971 | gagtgtttttcaaacaaatcggtgacggagataacgacgacgacgacgtcaacgagctcg |
| | ****************.*************************************** |
| HaWKRY76 | tcgtctgtagtatcgtcttccaccggtggaaacttagacggaagtgtttccaacggtaaa |
| HaT13\|007971 | tcgtctgtagtatcttcttccaccggtggaaacttagacggaagtgtttccaacggtaaa |
| | ***********.******************************************** |
| HaWKRY76 | cagttttcttcgttaggtatagtagctccggcgccgacgttctcgtctagaaaaccaccg |
| HaT13\|007971 | cagttttcttcgttaggtatagtagctccggcgccgacgttctcgtctagaaaaccaccg |
| | ************************************************************ |
| HaWKRY76 | ttaccgtcgacacaccggaaaaggtgcggcgctgatcgtcctgttgcttccgtacacgga |
| HaT13\|007971 | ttaccgtcgacacaccggaaaaggtgcggcgctgatcgtcctgttgcttccgtacacgga |
| | ************************************************************ |
| HaWKRY76 | tccggaagcggttgccattgttgttccaagagaaggaaaaccggatctaaacgtgaaatt |
| HaT13\|007971 | tccggaagcggttgccattgttgttccaagagaaggaaaaccggatctaaacgtgaaatt |

Fig. 2B

```
                    ************************************************************
HaWKRY76            agaagagttccgattaccggatctaaaattacaagcatacctgctgatgattactcatgg
HaT13|007971        agaagagttccgattaccggatctaaaattacaagcatacctgctgatgattactcatgg
                    ************************************************************

HaWKRY76            aaaaagtacggcgagaagaagatcgacggttcactttatccacgagtatattacaaatgt
HaT13|007971        aaaaagtacggcgagaagaagatcgacggttcactttatccacgagtatattacaaatgt
                    ************************************************************

HaWKRY76            attaccggaaaaggatgtccggcgaggaagcgcgtggagttaagcgccgacgattcgaag
HaT13|007971        attaccggaaaaggatgtccggcgaggaagcgcgtggagttaagcgccgacgattcgaag
                    ************************************************************

HaWKRY76            atgcttattgttacttacgacggagaacaccgtcaccgtgaccgtcacgcgccggtacct
HaT13|007971        atgcttattgttacttacgacggagaacaccgtcaccgtgaccgtcacgcgccggtacct
                    ************************************************************

HaWKRY76            atgagtttgaccggtgtgtatggtgagccaaagtgaa
HaT13|007971        atgagtttgaccggtgtgtatggtgagtcaaagtgag
                    *************************** *******.
```

Fig. 3

```
HaWRKY76       MAVDFVGIQSTDHLLNRMFQLLSHDLNVSSTYTHAVSAFKRTGHARFRRGPSSTTGDTNG
HuCL13748C001  MAVDFVGIQSTDHHLNRMFQLSTHDLNVSSTYTHAVSAFKRTGHARFRRGPSSTTGDTNG
               *************:******::**************************************

HaWRKY76       PSTSSHSEGKSRDTTSFVQNECFSNKPVTEITTTTTSTSSSSVVSSSTGGNLDGSVSNGK
HuCL13748C001  PSTSSHSEGKSRDTTSFVQNECFSNKSVTEITTTTTSTSSSSVVSSSTGGNLDGSVSNGK
               **************************.*********************************

HaWRKY76       QFSSLGIVAPAPTFSSRKPPLPSTHRKRCGADRPVASVHGSGSGCHCCSKRRKTGSKREI
HuCL13748C001  QFFSLGIVAPAPTFSSRKPPLPSTHRKRCSADRPVASVHGSGSGCHCCSKRRKTGSKREI
               ** *************************.*******************************

HaWRKY76       RRVPITGSKITSIPADDYSWKKYGEKKIDGSLYPRVYYKCITGKGCPARKRVELSADDSK
HuCL13748C001  RRVPITGSKITSIPADDYSWKKYGEKKIDGSLYPRVYYKCITGKGCPARKRVELSADDSK
               ************************************************************

HaWRKY76       MLIVTYDGEHRHRDRHAPVPMSLTGVYGEPK
HuCL13748C001  MLIVTYDGEHRHRDRHVPVLMSLTGVYGESK
               ****************.**.*********.*
```

Fig. 4A

| | |
|---|---|
| HaWRKY76 | atggcggttgatttcgtcggaattcaatctaccgatcatcttctaaaccgcatgttccag |
| HuCL13748C001 | atggcggttgatttcgtcggaattcaatctacagatcatcatctaaaccgcatgtttcag |
| | ********************************** ** *********.* |
| HaWRKY76 | ttattaagtcacgatttaaacgtttcgtcaacctacacgcacgcggtttctgctttcaaa |
| HuCL13748C001 | ttatcaactcacgatttaaacgtttcgtcaacctacacacacgcggtttctgctttcaaa |
| | **. ********************************.***************** |
| HaWRKY76 | cgcaccggtcacgcacggttccgccgtggaccgtcgtctaccaccggagacactaacgga |
| HuCL13748C001 | cgcaccggtcacgcacggttccgccgtggaccgtcgtctaccaccggagacactaacgga |
| | ************************************************************ |
| HaWRKY76 | ccttcaacttcttcacattcggaaggtaaatcacgagatgcgacttcgtttgtacaaaac |
| HuCL13748C001 | ccttcaacttcttcacattcggaaggtaaatcacgagatacgacgtcgtttgtacaaaac |
| | *************************************. ************ |
| HaWRKY76 | gagtgttttcaaacaaaccggtgacggagataacgacgacgacgacgtcaacgagctcg |
| HuCL13748C001 | gagtgttttcaaacaaatcggtgacggagataacgacgacgacgacgtcaacgagctcg |
| | ***************.**************************************** |
| HaWRKY76 | tcgtctgtagtatcgtcttccaccggtggaaacttagacggaagtgtttccaacggtaaa |
| HuCL13748C001 | tcgtctgtagtatcgtcttccaccggtggaaacttagacggaagtgtttccaacggtaaa |
| | ************************************************************ |
| HaWRKY76 | cagtttcttcgttaggtatagtagctccggcgccgacgttctcgtctagaaaaccaccg |
| HuCL13748C001 | cagttttttcgttaggtatagtagctccggcgccgacgttctcgtctagaaaaccaccg |
| | ****.*************************************************** |
| HaWRKY76 | ttaccgtcgacacaccggaaaaggtgcggcgctgatcgtcctgttgcttccgtacacgga |
| HuCL13748C001 | ctaccgtcgactcatcggaaaaggtgcagcgctgatcgtcctgttgcttccgtacacgga |
| | .****** .*********.*******.********************* |
| HaWRKY76 | tccggaagcggttgccattgttgttccaagagaaggaaaaccggatctaaacgtgaaatt |
| HuCL13748C001 | tctggaagcggttgccattgttgttccaagagaaggaaaaccggatctaaacgtgaaatt |

Fig. 4B

```
                    **.************************************************************
HaWRKY76            agaagagttccgattaccggatctaaaattacaagcatacctgctgatgattactcatgg
HuCL13748C001       agaagagttccgattaccggatctaaaattacaagcatacctgctgatgattactcatgg
                    ************************************************************

HaWRKY76            aaaaagtacggcgagaagaagatcgacggttcactttatccacgagtatattacaaatgt
HuCL13748C001       aaaaagtacggcgagaagaagatcgacggttcactttatccacgagtgtattacaaatgt
                    ************************************.***********

HaWRKY76            attaccggaaaaggatgtccggcgaggaagcgcgtggagttaagcgccgacgattcgaag
HuCL13748C001       attaccggaaaaggatgtccggcgaggaagcgcgtggagttaagcgccgacgattcgaag
                    ************************************************************

HaWRKY76            atgcttattgttacttacgacggagaacaccgtcaccgtgaccgtcacgcgccggtacct
HuCL13748C001       atgcttattgttacttacgacggagaacaccgtcaccgtgaccgtcacgtgccggtactt
                    *************************************************.*******.*

HaWRKY76            atgagtttgaccggtgtgtatggtgagccaaagtgaa
HuCL13748C001       atgagtttgaccggtgtgtatggtgagtcaaagtgag
                    ***************************.*******.
```

Fig. 7
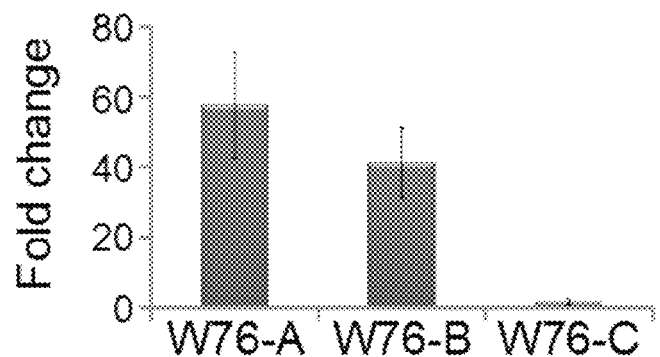
Fig. 8
a
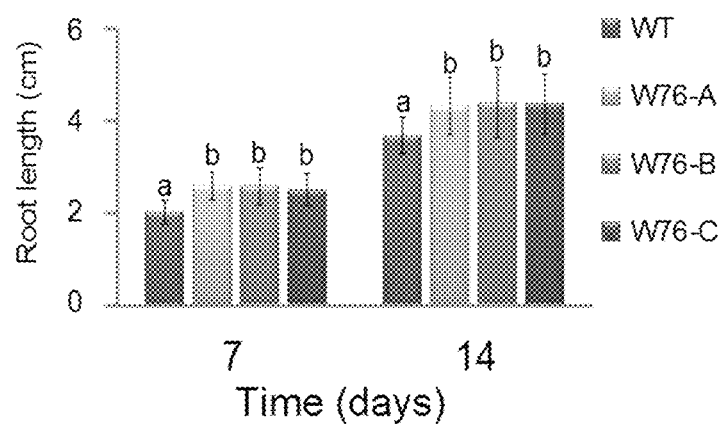
b
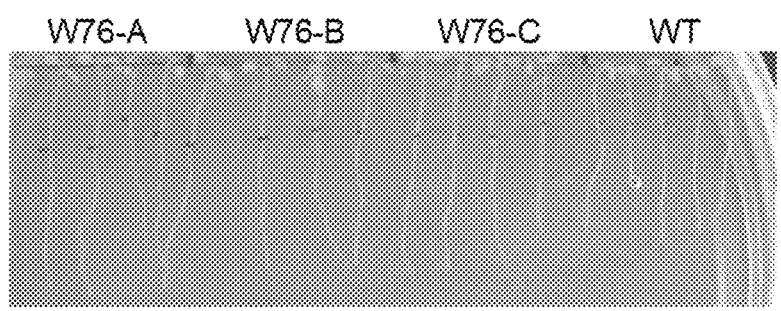

TRANSCRIPTION FACTOR GENES AND PROTEINS FROM *HELIANTHUS ANNUUS*, AND TRANSGENIC PLANTS INCLUDING THE SAME

CROSS-REFERENCE TO RELATED APPLICATIONS

This is a U.S. National Phase application claiming priority to PCT/GB2015/051269 filed Apr. 30, 2015, which claims priority to 61/986,730 filed. Apr. 30, 2014, the entire contents of which are hereby expressly incorporated by reference in its entirety including, without limitation, the specification, claims, and abstract, as well as any figures, tables, or drawings thereof.

BACKGROUND

Abiotic environmental stresses, such as drought, salinity, wind, heat, and cold, are major limiting factors of plant growth and crop yield. Prolonged or continuous exposure to drought conditions causes major alterations in the plant metabolism that ultimately lead to cell death and, consequently, losses in crop yield. High salt content in some soils results in less water being available for cell intake; thus, high salt concentration has an effect on plants similar to the effect of drought on plants. Under freezing temperatures, plant cells lose water as a result of ice formation within the plant. Because crop damage from abiotic stresses is predominantly due to dehydration, water availability is an important aspect of the abiotic stresses and their effects on plant growth. Losses in crop yield of major crops caused by these stresses represent a major economic factor and contribute to food shortages in many underdeveloped countries.

Most plants have evolved protective mechanisms against dehydration caused by abiotic stress. However, if the severity and duration of the abiotic stress conditions are too great, the effects on development, growth, and yield of most crop plants are profound. Developing plants efficient in water use is therefore a strategy that has the potential to benefit human life. Many agricultural companies have attempted to identify genes that could confer tolerance to abiotic stress responses, in an effort to develop transgenic abiotic stress-tolerant crop plants. For example, the genome of the plant model *Arabidopsis* was the first to be sequenced and released by 2000. Although some genes that play a role in stress responses or efficient water utilization in plants have been characterized, the characterization and cloning of plant genes that confer the desired stress tolerance and/or efficient water utilization characteristics remain largely fragmented and incomplete.

The sunflower belongs to the Asteraceae family, whose members represent 10% of the flowering plants. However, the genome sequence of this species is largely unknown and the huge quantity of expressed sequence tags (ESTs) from *Helianthus* (sunflower) species available in public databases have not yet been well explored.

SUMMARY

Embodiments relate to a polynucleotide having at least 85% sequence identity with the full-length nucleotide sequence of SEQ ID NO: 1 or SEQ ID NO: 9, or substantially identical variant polynucleotides, for example as shown in SEQ ID NO:11. A polynucleotide according to specific embodiments contains at least one of: (a) adenine as the nucleotide corresponding to position 817 of the full-length nucleotide sequence of SEQ ID NO: 1 or 11; and (b) cytosine as the nucleotide corresponding to position 808 of the full-length nucleotide sequence of SEQ ID NO: 1 or 11. In other embodiments, the polynucleotide may also contain at least one of the following: (c) cytosine as the nucleotide corresponding to position 33 of the full-length nucleotide sequence of SEQ ID NO: 1 or 11; (d) cytosine as the nucleotide corresponding to position 259 of the full-length nucleotide sequence of SEQ ID NO: 1 or 11; and (e) guanine as the nucleotide corresponding to position 315 of the full-length nucleotide sequence of SEQ ID NO: 1 or 11.

Embodiments also relate to vectors comprising a polynucleotide as described herein, recombinant expression cassettes comprising a polynucleotide described herein operably linked to a promoter, transgenic plants comprising such a recombinant expression cassette, and methods for producing such vectors, cassettes, and transgenic plants.

Embodiments also relate to isolated polypeptides having at least 85% sequence identity with the full-length amino acid sequence of SEQ ID NO: 2 or 12, or substantially identical polypeptides, for example as shown in SEQ ID NO:12. Polypeptides according to specific embodiments contain at least one of: (a) proline as the amino acid corresponding to position 270 of the full-length amino acid sequence of SEQ ID NO: 2 or 12; and (b) proline as the amino acid corresponding to position 87 of the full-length amino acid sequence of SEQ ID NO: 2 or 12. In embodiments, a polypeptide disclosed herein may contain at least one of: (c) proline as the amino acid corresponding to position 260 of the full-length amino acid sequence of SEQ ID NO: 2 or 12; (d) serine as the amino acid corresponding to position 123 of the full-length amino acid sequence of SEQ ID NO: 2 or 12; (e) leucine as the amino acid corresponding to position 14 of the full-length amino acid sequence of SEQ ID NO: 2 or 12; (f) leucine as the amino acid corresponding to position 22 of the full-length amino acid sequence of SEQ ID NO: 2 or 12; and (g) serine as the amino acid corresponding to position 23 of the full-length amino acid sequence of SEQ ID NO: 2 or 12.

Some embodiments relate to polynucleotides that encode a polypeptide described herein. A vector comprising a polynucleotide that encodes a polypeptide described herein, a recombinant expression cassette comprising such a polynucleotide operably linked to a promoter, transgenic plants comprising such a recombinant expression cassette, and methods for producing such products are also provided.

Some embodiments relate to recombinant expression cassettes comprising an isolated polynucleotide operably linked to a promoter, wherein the polynucleotide is a member selected from the group consisting of: (a) a polynucleotide that encodes the polypeptide of SEQ ID NO: 2 or a variant thereof, for example SEQ ID NO: 2; and (b) the polynucleotide of SEQ ID NO: 1 or 9 or a variant thereof.

The invention also relates to transgenic plants comprise such a recombinant expression cassette. The invention further provides a method of producing a transgenic plant comprising: (a) introducing into a plant cell such a recombinant expression cassette; and (b) culturing the plant cell under plant growing conditions to produce the transgenic plant. The invention also provides methods for modulating a plant phenotype, for example increasing yield of a plant under non-stress conditions comprising introducing and expressing a polynucleotide described herein, for example the polynucleotide of SEQ ID NO: 1 or a variant thereof, for example SEQ ID NO: 11, or SEQ ID NO: 9 or a variant thereof. Also, the invention provides a method for increasing stress tolerance of a plant to severe and/or moderate stress comprising introducing and expressing a polynucleotide described herein, for example the polynucleotide of SEQ ID NO: 1 or a variant thereof, for example SEQ ID NO: 11, or SEQ ID NO: 9 or a variant thereof.

In another aspect, the invention provides the use of a polynucleotide described herein, for example the polynucleotide of SEQ ID NO: 1 or a variant thereof, for example SEQ ID NO: 11, or SEQ ID NO: 9 or a variant thereof or a polypeptide encoded by any of these polynucleotides in altering a plant phenotype, specifically in increasing yield of a plant under non-stress conditions and/or for increasing stress tolerance of a plant to severe and moderate stress.

BRIEF DESCRIPTION OF THE SEQUENCES

SEQ ID NO: 1 is an isolated nucleotide sequence (cDNA) of the HaWRKY76 polynucleotide.

SEQ ID NO: 2 is an isolated amino acid sequence of the HaWRKY76 polypeptide.

SEQ ID NO: 3 is an isolated nucleotide sequence of the HaT131007971 polynucleotide (as identified in the Helia database).

SEQ ID NO: 4 is an isolated amino acid sequence of the HaT131007971 polypeptide (as identified in the *Helianthus annuus* cv. XRQ transcriptome portal).

SEQ ID NO: 5 is an isolated nucleotide sequence of the HuCL13748C001 polynucleotide (as identified in the Helia database).

SEQ ID NO: 6 is an isolated amino acid sequence of the HuCL13748C001 polypeptide (as identified in the Helia database).

SEQ ID NO: 7 is a conserved motif.

SEQ ID NO: 8 is a conserved motif.

SEQ ID NO: 9 is the HaWRKY76 genomic DNA.

SEQ ID NO: 10 is the promoter DNA.

SEQ ID NO: 11 is an isolated variant nucleotide sequence (cDNA) of the HaWRKY76 polynucleotide SEQ ID NO: 12 is an isolated amino acid sequence of the HaWRKY76 polypeptide.

BRIEF DESCRIPTION OF THE DRAWINGS

FIG. 1 is a comparison of the amino acid sequence of the HaT131007971 polypeptide of SEQ ID NO: 4 with the amino acid sequence of the HaWRKY76 polypeptide of SEQ ID NO: 2.

FIG. 2 is a comparison of the nucleotide sequence of the HaT131007971 polynucleotide of SEQ ID NO: 3 with the nucleotide sequence of the HaWRKY76 polynucleotide of SEQ ID NO: 1.

FIG. 3 is a comparison of the amino acid sequence of the HuCL13748C001 polypeptide of SEQ ID NO: 6 with the amino acid sequence of the HaWRKY76 polypeptide of SEQ ID NO: 2.

FIG. 4 shows the nucleotide sequence of the HaWRKY76 polynucleotide of SEQ ID NO: 1 with a related sequence.

FIG. 7 shows the Ha WRKY76 expression levels of three homozygous transgenic lines of *Arabidopsis* transgenic plants bearing the construct 35S:HaWRKY76.

FIG. 8A shows root lengths of three homozygous transgenic lines of *Arabidopsis* transgenic plants bearing the construct 35S:HaWRKY76 and of WT control plants, and the photograph of FIG. 8B shows roots of the 7-day-old plants grown on Petri dishes.

FIG. 21A shows the content of soluble glucose per mg fresh rosette weight of the respective plants, FIG. 21B shown the sucrose content per mg fresh rosette weight of the respective plants, and FIG. 21C shows the starch content per mg fresh rosette weight of the respective plants. Different letters indicate samples that are significantly different (p value<0.05).

DETAILED DESCRIPTION OF THE EMBODIMENTS OF THE INVENTION

Definitions

Figure 5:
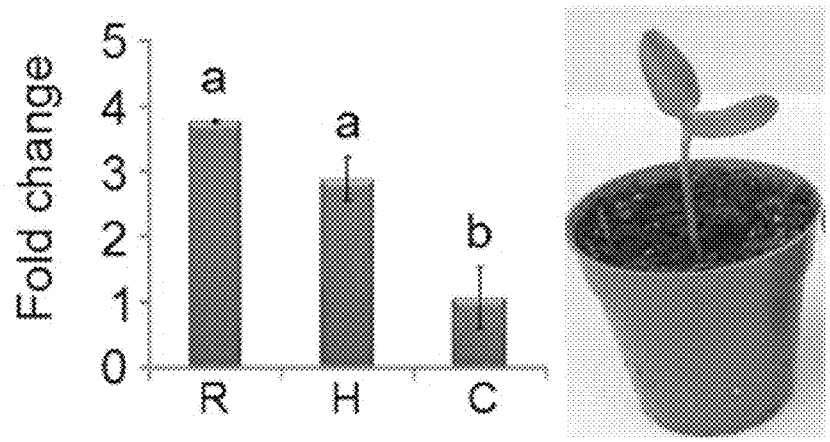
FIG. 5 shows the HaWRKY76 expression levels in the roots, hypocotyls, and cotyledons in 5-day-old sunflower seedlings. Different letters indicate samples that are significantly different (p value<0.05). An illustrative photograph of a sunflower plant in the developmental stage used to take the RNA samples is shown in the right side.

Unless otherwise indicated, nucleic acids are written left to right in 5' to 3' orientation, and amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "amplified" refers to the construction of multiple copies of a nucleic acid sequence or multiple copies complementary to the nucleic acid sequence using at least one of the nucleic acid sequence as a template. Amplification systems include, but are not limited to, polymerase chain reaction (PCR), ligase chain reaction (LCR) system, nucleic acid sequence based amplification (NASBA), Q-Beta Replicase systems, transcription-based amplification system (TAS), and strand displacement amplification (SDA). See, e.g., D. H. Persing et al., "Diagnostic Molecular Microbiology: Principles and Applications," American Society for Microbiology, Washington D.C. (1993).

The term "introduced" or "introducing" as used herein in the context of inserting into a cell refers to the incorporation of a nucleic acid into a target cell, such as a plant cell, such that the nucleic acid may be incorporated into the genome of the cell (e.g., chromosome, plasmid, plastid or mitochondrial DNA), converted into an autonomous replicon, or transiently expressed (e.g., transfected mRNA). In embodiments, introducing a nucleotide sequence into a plant cell results in transformation of the plant cell to cause stable or transient expression of the sequence.

The term "isolated" as used herein refers to material, such as a nucleic acid or a protein, which is substantially or essentially free of components that normally accompany or interact with the material within its naturally occurring environment. The isolated material may include a material not found with the material in its natural environment, or if the material is in its natural environment, the material has been synthetically (i.e., non-naturally) altered by deliberate human intervention to form a composition and/or be found in a location in the cell (e.g., genome or subcellular organelle) not native to the material found in that environment. The alteration forming the synthetic material can be performed on the material within or removed from its natural state. For example, a naturally occurring nucleic acid becomes an isolated nucleic acid if it is altered, by means of human intervention on the cell from which it originates. Likewise, a naturally occurring nucleic acid (e.g., a promoter) becomes isolated if it is introduced by non-naturally occurring means to a locus of the genome not native to that nucleic acid, as discussed further below.

As used herein, the term "nucleic acid" (or "polynucleotide") refers to a deoxyribonucleotide or a ribonucleotide polymer, or analog thereof, that has the essential nature of natural nucleotides in that it hybridizes, under stringent hybridization conditions, to substantially the same nucleotide sequence as naturally occurring nucleotides and/or allows translation into the same amino acid(s) as the naturally occurring nucleotide(s). A polynucleotide can be full-length or a sub-sequence of a native or heterologous structural or regulatory gene. Unless otherwise indicated herein, the term refers to a specified sequence, as well as the complementary sequence thereof. Thus, DNAs or RNAs with backbones modified for stability or for other reasons, as well as DNAs and RNAs comprising unusual or modified bases, are polynucleotides as the term is defined herein. The term polynucleotide also encompasses chemically, enzymatically, or metabolically modified forms of polynucleotides, as well as the chemical forms of DNA and RNA characteristic of simple and complex cells. The term "nucleic acid" (or "polynucleotide") may be used in place of, inter alia, gene, cDNA, mRNA, or cRNA.

As used herein, the term "operably linked" refers to a functional linkage between sequences, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous in the same reading frame.

The term "plant" is used broadly herein to describe a plant at any stage of development, to a part of a plant (e.g., plant cell, plant cell culture, plant organ, plant seed, etc.), and to progeny thereof. A "plant cell" is the structural and physiological unit of the plant, comprising a protoplast and a cell wall. A plant cell can be in the form of an isolated single cell or a cultured cell, or can be part of a higher organized unit, such as plant tissue, a plant organ, or a plant. Thus, a plant cell can be a protoplast, a gamete-producing cell, or a cell or collection of cells that can regenerate into a whole plant. As used herein, a "seed" comprises multiple plant cells and is capable of regenerating into a whole plant, and may therefore be considered a plant cell. A plant tissue or organ can be a seed, protoplast, callus, or any other group of plant cells that is organized into a structural or functional unit. Parts of a plant that are particularly useful in embodiments include non-harvestable parts and parts used for propagation of progeny plants. A harvestable part of a plant may include the flowers, pollen, seedlings, tubers, leaves, stems, fruit, seeds, roots, and the like. Parts of the plant used for propagation include, e.g., seeds, fruits, cuttings, seedlings, tubers, rootstocks, and the like. The class of plants that may be used is generally as broad as the class of higher plants amenable to transformation techniques, including both monocotyledonous and dicotyledonous plants.

The terms "polypeptide" and "protein" as used herein refer to a polymer of amino acid residues. The terms encompass amino acid polymers, in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids. The polypeptide group includes, but is not limited to, DNA binding proteins, protein kinases, protein phosphatases, GTP-binding proteins, and receptors.

As used herein, the term "promoter" refers to a region of DNA that is upstream from the start of transcription and that is involved in recognition and binding of RNA polymerase and other proteins to initiate transcription. The promoter may be any polynucleotide sequence that shows transcriptional activity in the host (target) plant cells, plant parts, or plants.

As used herein, the term "recombinant" refers to a cell or vector that has been modified by the introduction of a heterologous nucleic acid or a cell that is derived from a cell so modified. For example, recombinant cells express genes that are not found in identical form within the native (non-recombinant) form of the cell or express native genes that are otherwise abnormally expressed, under-expressed, or not expressed at all as a result of deliberate human intervention. The term does not encompass the alteration of the cell or vector by naturally occurring events (e.g., spontaneous mutation, or natural transformation, transduction, or transposition).

As used herein, the term "recombinant expression cassette" (or "expression cassette") refers to a nucleic acid construct that is recombinantly or synthetically generated with a series of specified nucleic acid elements, that permits transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes a nucleic acid to be transcribed and a promoter.

As used herein, the term "regulatory element" means a nucleotide sequence that, when operatively linked to a coding region of a gene, effects transcription of the coding region such that a ribonucleic acid (RNA) molecule is transcribed from the coding region. Regulatory elements include promoters, enhancers, silencers, 3'-untranslated or 5'-untranslated sequences of transcribed sequences, e.g., a poly-A signal sequence or other protein or RNA stabilizing element, or other gene expression control elements known to regulate gene expression or the amount of expression of a gene product.

The terms "residue", "amino acid residue", and "amino acid" are used interchangeably herein to refer to an amino acid that is incorporated into a protein, polypeptide, or peptide. The amino acid may be a naturally occurring amino acid and, unless otherwise limited, may encompass non-natural analogs of natural amino acids that can function in a similar manner as naturally occurring amino acids.

As used herein, "sequence identity" in the context of two polynucleotide or polypeptide sequences refers to the residues in the two sequences that are the same when aligned for maximum correspondence over a comparison window of a contiguous and specified segment of a polynucleotide sequence. When percentage of sequence identity is used in reference to proteins, it is recognized that residue positions that are not identical often differ by conservative amino acid substitutions. Where sequences differ in conservative substitutions, the percent sequence identity may be adjusted upwards to correct for the conservative nature of the substitution. Sequences differing by such conservative mutations are said to have "sequence similarity." Methods for making this adjustment are well known to persons skilled in the art. The "percentage" of sequence identity means the value determined by comparing two optimally aligned sequences over a comparison window, wherein the portion of the polynucleotide sequence in the comparison window may include additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, the term "transgenic plant" refers to a plant that includes within its genome a heterologous polynucleotide. Generally, the heterologous polynucleotide is stably integrated within the genome of the transgenic plant, such that the polynucleotide is passed on to successive generations. The term "transgenic" is used herein to describe any cell, cell line, callus, tissue, plant part or plant (also referred to herein as a "target cell" or "host cell") the genotype of which has been altered by the presence of a heterologous nucleic acid, and includes transgenic plants that have been initially altered, as well as those created by sexual crosses or asexual propagation from the initial transgenic plants. The term "transgenic" as used herein does not encompass the alteration of the genome by naturally occurring events, such as random cross-fertilization or spontaneous mutation.

As used herein, the term "vector" refers to a nucleic acid used in the transfection of a target cell and into which can be inserted a polynucleotide. Vectors are often replicons. Expression vectors permit transcription of a nucleic acid inserted therein.

As used herein, the term "wild-type" (or "WT") refers to a cell or plant that has not been genetically modified to knock out or over-express polypeptides according to embodiments of the present disclosure. Wild-type cells or plants may be used as controls to compare levels of expression and the extent and nature of trait modification in genetically modified (i.e., transgenic) cells or plants in which polypeptide expression is altered or ectopically expressed by, for example, knocking out or over-expressing a gene.

Detailed Description of Embodiments

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

External stress factors, from both biological and abiotic origins, affect the levels of specific proteins by transcriptional and/or post-transcriptional regulation. The ability of a given species to survive various stress conditions is intimately related to a series of molecular responses involving activation and repression of certain genes. The stress tolerance of a species appears to be controlled primarily at the transcriptional level, depending on the transcription factor activity.

As in other species, the primary players regulating gene expression in sunflowers are transcription factors and genomic regulatory regions (as well as small RNAs, including miRNAs). Transcription factors are proteins that are able to recognize and bind specific DNA sequences present in the regulatory regions of their target genes, and modulate their transcription. It is known that transcription factors have a modular structure and exhibit at least two types of domains: a DNA binding domain; and a protein-protein interaction domain, which mediates (directly or indirectly) the activation or repression of transcription. See Brivanlou and Darnell, "Signal transduction and the control of gene expression," *Science* 295:813-818 (2002). Additionally, transgenic plants comprising isolated polynucleotides encoding transcription factors may also modify expression of endogenous genes, polynucleotides, and proteins. See Peng et al., *Genes and Development* 11:3194-3205 (1997), and Peng et al., *Nature* 400:256-261 (1999).

Within a single plant species, gene duplication may cause two copies of a particular gene, giving rise to two or more genes with similar sequences and often similar functions, known as paralogs. A paralog is therefore a similar gene formed by duplication within the same species. Paralogs typically cluster together or in the same clade (i.e., a group of similar genes) when a gene family phylogeny is analyzed using programs known to persons skilled in the art. For example, a clade of very similar transcription factors of the same species typically will share a common function (e.g., flowering time, drought tolerance, etc.). Analysis of groups of similar genes having a similar function that fall within one clade can yield sub-sequences that are particular to that clade. These sub-sequences, known as "consensus sequences," can be used not only to define the sequences within each clade, but also to define the functions of these genes; genes within a clade may contain paralogous sequences, or orthologous sequences that share the same function. See, e.g., Mount, "Bioinformatics: Sequence and Genome Analysis," Cold Spring Harbor Laboratory Press, Cold Spring Harbor, N.Y., p. 543 (2001).

Transcription factor gene sequences are conserved across diverse eukaryotic species lines. Plants are no exception to this observation; diverse plant species possess transcription factors that have similar sequences and functions. Speciation for the production of new species from a parental species gives rise to two or more genes with similar sequence and similar function. These genes, or "orthologs," often have an identical function within their host plants and are often interchangeable between species without losing function. Because plants have common ancestors, many genes in any plant species will have a corresponding orthologous gene in another plant species. Once a phylogenic tree for a gene family of one species has been construed using a program, such as CLUSTAL, potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence. By using a phylogenetic analysis, persons skilled in the art would be able to predict similar functions conferred by closely-related polypeptides. An orthologous sequence of a plant, including plants specifically mentioned herein, can have at least 70%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the Ha nucleic acid or protein described herein. The invention also includes embodiments that relate to orthologous sequences.

Although approximately 2000 plant transcription factors have been identified in plants in silico and classified in families and sub-families according to similarities in the respective binding domains, gene structures, functions and other structural features, only a small percentage of those transcription factors has been functionally characterized (even in model plants). The WRKY transcription factors of *Arabidopsis* are an example of one such classified family, which has also been functionally characterized as related to abiotic and biotic stress responses. See, e.g., Giacomelli et al. (2010) and Giacomelli et al. (2012). Specifically, the distinct transcription factors of the WRKY family in *Arabidopsis* and numerous closely-related sequences from dicots and monocots have been shown to confer increased water deprivation tolerance.

The WRKY transcription factors are primarily characterized by the presence of a 60 amino acid conserved region containing the four WRKY amino acids and a zinc-finger-like motif, which together form the WRKY domain. These proteins are unique to plants and have been classified in *Arabidopsis* into three main groups (I, II, and III) on the basis of both the number of WRKY domains and the pattern of the zinc-finger-like motif, with the second group being further classified in five subgroups (IIa, IIb, IIc, IId, and IIe). See Eulgem and Somssich, "Networks of WRKY transcription factors in defense signaling," *Curr. Opin. Plant Biol.* 10:366-371 (2007); and Rushton et al., "WRKY transcription factors," *Trends in Plant Sci.*, 15:247-258 (2010).

In a study to identify and characterize WRKY transcription in the sunflower (belonging to the Asteraceae family) using in silico approaches and gene expression surveys, a bioinformatics analysis of EST databases estimated the existence of 97 sunflower WRKY members. See Giacomelli et al., "Expression analyses indicate the involvement of sunflower WRKY transcription factors in stress responses, and phylogenetic reconstruction reveal the existence of a novel clade in the Asteraceae," *Plant Science* 178:398-410 (2010). Phylogenetic trees constructed with WRKY domains resolved the same seven groups assigned to *Arabidopsis*, as well as a novel clade diverging with the lid subgroup as described above, with traits apparently specific to Asteraceae. The 2010 study referenced above indicated that the WRKY family has undergone a particular diversification, which could be the source of specific new functions. A partial sequence of HaWRKY76, a member of this Asteraceae specific clade, was also reported in the study.

A schematic representation of the deduced proteins with a WKKY motif corresponding to EST-clusters from *Helianthus* spp. and *Lactuca* spp. is provided in Giacomelli et al. (2010), which shows the putative conserved primary structural features of the *Helianthus/Lactuca* WKKY (WKKY-GEK, SEQ ID NO:7) motif encoding proteins. All of the expressed sequence tags (ESTs) identified as proteins having WKKY motif-encoding sequences (52) were obtained from GenBank, and the EST-clusters resulting from the assembly (18) were translated. In Giacomelli's schematic representation, conserved primary structural features identified by using MEME (Bailey and Elkan (1994)) are identified with grey boxes and labels. Box A shows the N-terminal consensus sequence, box H shows the HARF motif, box C shows the calmodulin-binding protein, box Z shows the zinc cluster, and box P shows the proline-rich motif. An alignment was performed using MAFFT (Lopez R. (1997)) and two regions from it are shown in detail below the scheme described above. The first region shown is the serine-rich region, which has divergences in five identified clusters. The second region shows is the WKKY domain.

The WKKY clade proteins present structural differences relative to members of the WRKY family. Specifically, the WKKY proteins contain motifs unique to the lid WRKY members, the C, the HARF and a zinc cluster upstream of the WKKY domain (not the zinc-finger-like motif proper of the WRKY domain). Moreover, they exhibit an additional remarkable feature: the presence of two substitutions in the main region of the WRKYGQK (SEQ ID NO:8) domain that result in a WKKYGEK motif (SEQ ID NO:7). Other signatures that have not been reported in other WRKY proteins, such as a conserved N-terminal region, a putative serine-threonine kinase domain, and proline-rich region (P), were also clearly identified.

Since WKKY proteins share conserved structures with lid WRKY group members, it is possible that they have some properties in common. For example, the expression of members of the lid WRKY group is induced by pathogen infection and SA. Additionally, EMSA assays performed with AtWRKY11 showed that the substitution of RK by KR in the WRKY domain avoided the interaction with the W-box. See Ciolkowski et al., "Studies on DNA-binding selectivity of WRKY transcription factors lend structural clues into WERKY-domain function," *Plant Molecular Biology* 68:81-92 (2008). In contrast, EMSA assays performed with HaWRKY76 indicated that this protein selected a different DNA sequence. Because WKKY proteins share conserved structures with lid WRKY members, it is possible that the proteins have in common the properties associated with these structures. Similar to the expression of proteins belonging to the lid WRKY group being induced by pathogen infection and SA concomitantly with a calcium discharge, the zinc cluster could be involved in determining the DNA affinity as it was demonstrated for AtWRKY11. However, this *Arabidopsis* transcription factor presented a reduced affinity for a W-box when a single D to E amino acid was substituted within the N-terminal region to the WRKY domain. Because sunflower proteins with a WKKY motif do not have a D within the zinc cluster, different amino acids could be determining the affinity of these proteins for their target sequences.

The expression of sunflower WRKY genes is regulated by hormones, abiotic and biotic factors, and wounding. The published study of Giacomelli et al. (2010) includes a comparative diagram of selected expression profiles of sunflower WRKY genes after three-hour treatments with hormones or factors associated with stress, i.e., the hormones CK (100 µM 6-benzylaminopurine), GA (100 µM gibberellin $A_3$), AUX (100 µM indole-3-acetic acid), ACC (30 µM aminocyclopropane-carboxylic acid), JA (200 µM MeJA), and SA (1 mM), the wounding damage (WO), MAN 350 mM D-mannitol), SALT (150 mM NaCl) and the *Pseudomonas syringae* DC3000 spraying (PS). The transcript levels were measured by quantitative RT-PCR and standard errors were calculated from three biological replicates in which actin transcripts (HaACTIN) were used as internal controls.

The presence of the exclusive stretches found only in members of the WKKY clade suggests that they could be the basis of a neo-functionality. In this sense, the serine-rich sequence found by the ELM program could be a target of a serine-threonine kinase. PPLP motifs are proline-rich sequences present in ligands interacting with WW domains. Notably, proline residues in the PPLP motif identified in sunflower WKKYs are quite equally distributed as in FY PPLP [PxP(x)$_7$PPLP], but the spacer sequences are completely different.

Besides the 2010 publication and the subsequent Ph.D. Thesis of Jorge Giacomelli (2011), no additional information regarding any HaWRKY76 sequences (including the HaWRKY76 sequence of Giacomelli (2010)) have been reported, and no functional analyses have been conducted.

Using techniques described herein, the inventors have now cloned the complete HaWRKY76 under the control of a 35S CaMV promoter. The HaWRKY76 nucleotide sequence and polypeptide (protein) sequence below correspond to SEQ ID NO: 1 and SEQ ID NO: 2, respectively. The HaWRKY76 transcription factor has a WKK motif because there is a change of R to K in the WRKY domain. Thus, HaWRKY76 is also referred to as a WKKY transcription factor herein.

HaWRKY76 nucleotide sequence of SEQ ID NO: 1 (cDNA)

```
atggcggttgatttcgtcggaattcaatctaccgatcatcttctaaaccg catgttccagttattaagtcacgatttaaacgtttcgtcaacctacacgc acgcggtttctgctttcaaacgcaccggtcacgcacggttccgccgtgga ccgtcgtctaccaccggagacactaacggaccttcaacttcttcacattc ggaaggtaaatcacgagatacgacttcgtttgtacaaaacgagtgttttt caaacaaaccggtgacggagataacgacgacgacgacgtcaacgagctcg tcgtctgtagtatcgtcttccaccggtggaaacttagacggaagtgtttc caacggtaaacagttttcttcgttaggtatagtagctccggcgccgacgt tctcgtctagaaaaccaccgttaccgtcgacacaccggaaaaggtgcggc gctgatcgtcctgttgcttccgtacacggatccggaagcggttgccattg ttgttccaagagaaggaaaaccggatctaaacgtgaaattagaagagttc cgattaccggatctaaaattacaagcatacctgctgatgattactcatgg aaaaagtacggcgagaagaagatcgacggttcactttatccacgagtata
```

-continued

```
ttacaaatgtattaccggaaaaggatgtccggcgaggaagcgcgtggagt taagcgccgacgattcgaagatgcttattgttacttacgacggagaacac cgtcaccgtgaccgtcacgcgccggtacctatgagtttgaccggtgtgta tggtgagccaaagtgaa Corresponding HaWRKY76 polypeptide (protein)
sequence of SEQ ID NO: 2
MAVDFVGIQSTDHLLNRMFQLLSHDLNVSSTYTHAVSAFKRTGHARFRRG

PSSTTGDTNGPSTSSHSEGKSRDTTSFVQNECFSNKPVTEITTTTTSTSS

SSVVSSSTGGNLDGSVSNGKQFSSLGIVAPAPTFSSRKPPLPSTHRKRCG

ADRPVASVHGSGSGCHCCSKRRKTGSKREIRRVPITGSKITSIPADDYSW

KKYGEKKIDGSLYPRVYYKCITGKGCPARKRVELSADDSKMLIVTYDGEH

RHRDRHAPVPMSLTGVYGEPK
```

A sequence having similarity with the HaWRKY76 sequences disclosed herein has been reported in the Helia database. The gene and protein sequences of HaT131007971 correspond to SEQ ID NO: 3 and SEQ ID NO: 4, respectively. A comparison of the HaT131007971 polypeptide (protein) sequence (SEQ ID NO: 4) with the full-length polypeptide (protein) sequence of HaWRKY76 (SEQ ID NO: 2) indicates several differences, as shown in FIG. 1. A comparison of the HaT131007971 polynucleotide sequence (SEQ ID NO: 3) with the full-length polynucleotide sequence of HaWRKY76 (SEQ ID NO: 1) indicates several differences, as shown in FIG. 2.

Another sequence having similarity with the HaWRKY76 sequences disclosed herein is HuCL13748C001, which has also been reported in the Helia database. The gene and protein sequences of the HuCL13748C001 correspond to SEQ ID NO: 5 and SEQ ID NO: 6, respectively. A comparison of the polypeptide (protein) sequence of HuCL13748C001 (SEQ ID NO: 6) with the full-length polypeptide (protein) sequence of HaWRKY76 (SEQ ID NO: 2) indicates several differences, as shown in FIG. 3. A comparison of the polynucleotide sequence of HuCL13748C001 (SEQ ID NO: 5) and the full-length polynucleotide sequence of HaWRKY76 (SEQ ID NO: 1) indicates several differences, as shown in FIG. 4. These differences have not yet been evaluated for functional roles, but some of them are not conservative and/or located in putative functional domains.

It is generally understood that the up-regulation of a certain gene by any abiotic stress factor does not mean that the gene will confer tolerance to such stress if it is used as a transgene. Moreover, the ability of a gene to confer tolerance to a given stress factor does not imply that it will confer tolerance to other stress factors. Many examples of genes conferring tolerance to drought but not to, e.g., high temperatures, are described in scientific literature and understood by persons skilled in the art. In the same way, tolerance to low temperatures above 0° C. (chilling) is generally not concomitant with tolerance to low temperatures below 0° C. (freezing) since different molecular mechanisms are playing a role in these responses.

In the same way, it is also generally understood that tolerance to drought does not imply tolerance to submergence or waterlogging because different signal transduction pathways are triggered in these responses. Likewise, tolerance to drought or to any other abiotic stress factor does not imply increased yield under such stresses. While tolerance is usually evaluated and reported as a percentage of survivors after a severe stress treatment, the yield under such conditions is generally not informed under moderate stress conditions. See e.g., Skirycz et al., "Survival and growth of *Arabidopsis* plants given limited water are not equal," *Nature Biotechnology* 29:212-214 (2011) (reporting that 25 genes known to confer drought tolerance exhibited decreased yield in standard conditions or under a moderate drought stress). Such moderate stress is the most common and probable growing condition encountered by plants in the field.

Thus, a combination of increased yield (or at least no decrease in yield) and stress tolerance represents a very valuable characteristic of technologies to improve crops. As described in connection with the various embodiments and specific Examples provided herein, HaWRKY76 unexpectedly offers this highly advantageous combination of characteristics.

As indicated above, the complete HaWRKY76 was cloned under the control of the 35S CaMV promoter. This construct was further used to transform *Arabidopsis* plants to produce transgenic plants exhibiting different expression levels of HaWRKY76. Plants produced according to the methods described herein were analyzed both in standard growth conditions and in growth conditions in which they were subjected to abiotic stress factors.

The analysis revealed, among other things, that when grown under standard conditions, 35S:HaWRKY76 transgenic plants have a similar number of rosette leaves, life cycle duration and stem length as the corresponding WT control plants. However, transgenic plants bearing the construct 35S:HaWRKY76 were found to have longer roots and larger rosettes than corresponding WT control plants. Moreover, total protein and chlorophyll contents of the transgenic plants were found to be proportional to the rosette weight (i.e., 35S:HaWRKY76 plants produce more biomass and protein than control plants). Furthermore, when subjected to water stress, transgenic plants bearing the construct 35S:HaWRKY76 were found to be more tolerant to drought than corresponding WT control plants, and similar properties were observed when the transgenic plants were stressed by submergence or waterlogging. Notably, transgenic plants bearing the construct 35S:HaWRKY76 not only demonstrated improved tolerance to the various moderate and severe stress conditions, but also exhibited higher yields than the corresponding WT control plants (yield evaluated as a measure of seed production).

The HaWRKY76 transcription factor polypeptides confer on transgenic plants produced according to methods described herein improved stress tolerance, as well as increased yield in standard growing conditions. Specifically, as evidenced by the various Examples and applicable Figures, the inventors unexpectedly discovered that the HaWRKY76 sequences confer tolerance to drought, submergence and waterlogging, while also increasing yield in standard conditions.

It will be understood by persons skilled in the art that embodiments of the invention also relate to, among other things, the isolation and functional characterization of the HaWRKY76 nucleotide and amino acid sequences, transgenic plants transformed with constructs comprising the HaWRKY76 polynucleotide sequences, and methods of producing transgenic plants expressing the HaWRKY76 polypeptide sequences disclosed herein, wherein the transgenic plants have improved stress tolerance and increased yield in comparison to corresponding control plants, for example WT plants.

WRKY76 Transcription Factor Polynucleotides

In embodiments of the aspects of the invention, the polynucleotides described herein include nucleotide sequences that encode WRKY76 transcription factors and transcription factor homolog polypeptides and sequences complementary thereto, as well as unique fragments of a coding sequence, or a sequence complementary thereto. The polynucleotides may be, e.g., DNA or RNA, such as mRNA, cRNA, synthetic RNA, genomic DNA, cDNA synthetic DNA, oligonucleotides, etc. The polynucleotides are either double-stranded or single-stranded and include either or both sense (i.e., coding) sequences and antisense (i.e., non-coding, complementary) sequences. The polynucleotides may include the coding sequence of a transcription factor or transcription factor homolog polypeptide, in isolation, in combination with additional coding sequences, in combination with non-coding sequences (e.g., introns, regulatory elements such as promoters, enhancers, terminators, and the like), and/or in a vector or host environment in which the polynucleotide encoding a transcription factor or transcription factor homolog polypeptide is an endogenous or exogenous gene. WRKY76 transcription factors include the signature motif WKKYGEK (SEQ ID NO:7). WRKY76 transcription factors also include a conserved serine-threonine kinase domain and a proline-rich region.

Representative polynucleotides of WRKY76 transcription factors include the full-length polynucleotide sequence of SEQ ID NO: 1, and functional variants or parts thereof which retain biological function of the full-length polynucleotide sequence of SEQ ID NO: 1 or SEQ ID NO:9, for example SEQ ID NO: 11. Preferably, variants are substantially identical polynucleotides. Substantially identical polynucleotides comprise nucleotide sequences that vary from the full-length amino acid sequence of SEQ ID NO: 1 by one or more modifications, including deletions, substitutions, or additions, the net effect of which is retained biological function of the WRKY76 polynucleotide. For example, substantially identical polynucleotides comprise nucleotide sequences that vary from the full-length amino acid sequence of SEQ ID NO: 1 by 1, 2, 3, 4, 5, 6, 7, 8, 9 or 10 substitutions, or additions. In some embodiments, variants, such as substantially identical WRKY76 polynucleotides may have at least 80% sequence identity with the full-length nucleotide sequence of SEQ ID NO: 1 or SEQ ID NO:9 as described herein, or by visual inspection. Preferably, the WRKY76 polynucleotides have at least 85% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity with the full-length nucleotide sequence of SEQ ID NO: 1. For example, sequence identity is at least 80%, 81%, 82%, 83%, 84%, 85%, 86%, 87%, 88%, 89%, 90%, 91%, 92%, 93%, 94%, 95%, 96%, 97%, 98%, 99% or 100%. A variant within the scope of the various aspects of the invention is shown in SEQ ID NO: 11 and the corresponding polypeptide SEQ ID NO: 12.

In some embodiments of the various aspects of the invention, the isolated polynucleotides of the invention contain at least one of the following: (a) adenine as the nucleotide corresponding to position 817 of the full-length nucleotide sequence of SEQ ID NO: 1 or a variant thereof, for example SEQ ID NO: 11; (b) cytosine as the nucleotide corresponding to position 808 of the full-length nucleotide sequence of SEQ ID NO: 1 or a variant thereof, for example SEQ ID NO: 11; (c) cytosine as the nucleotide corresponding to position 33 of the full-length nucleotide sequence of SEQ ID NO: 1 or a variant thereof, for example SEQ ID NO: 11; (d) cytosine as the nucleotide corresponding to position 259 of the full-length nucleotide sequence of SEQ ID NO: 1 or a variant thereof, for example SEQ ID NO: 11; and (e) guanine as the nucleotide corresponding to position 315 of the full-length nucleotide sequence of SEQ ID NO: 1 or a variant thereof, for example SEQ ID NO: 11. In particular, in one aspect, the invention relates to an isolated polynucleotide having at least 80% sequence identity with the full-length nucleotide sequence of SEQ ID NO: 1 or a variant thereof, for example SEQ ID NO: 11, wherein the polynucleotide contains at least one of:

(a) adenine as the nucleotide corresponding to position 817 of the full-length nucleotide sequence of SEQ ID NO: 1 or a variant thereof, for example SEQ ID NO: 11;

(b) cytosine as the nucleotide corresponding to position 808 of the full-length nucleotide sequence of SEQ ID NO: 1 or a variant thereof, for example SEQ ID NO: 11;

(c) cytosine as the nucleotide corresponding to position 33 of the full-length nucleotide sequence of SEQ ID NO: 1 or a variant thereof, for example SEQ ID NO: 11;

(d) cytosine as the nucleotide corresponding to position 259 of the full-length nucleotide sequence of SEQ ID NO: 1 or a variant thereof, for example SEQ ID NO: 11; and (e) guanine as the nucleotide corresponding to position 315 of the full-length nucleotide sequence of SEQ ID NO: 1 or a variant thereof, for example SEQ ID NO: 11. Preferably, the isolated polynucleotide is cDNA.

Substantially identical polynucleotide sequences may be polymorphic sequences, i.e., alternative sequences or alleles in a population in which the allelic difference may be as small as one base pair. Substantially identical polynucleotides may also comprise mutagenized sequences, including sequences comprising silent mutations. A mutation may comprise one or more residue changes, a deletion of one or more residues, or an insertion of one or more additional residues.

Representative polynucleotides according to some embodiments of the various aspects of the invention include the polynucleotide comprising or consisting of SEQ ID NO: 1 or SEQ ID NO: 9 and substantially identical nucleotides, and polynucleotides that encode the HaWRKY76 transcription factor polypeptide comprising or consisting of SEQ ID NO: 2. Thus, in one embodiment, the isolated polynucleotide comprises or consists of SEQ ID NO:1. In one embodiment, the isolated polynucleotide comprises or consists of SEQ ID NO:1.

Substantially identical polynucleotides according to embodiments include polynucleotides that hybridize specifically to or hybridize substantially to the full-length nucleotide sequence of SEQ ID NO: 1, 11 or 9 under stringent conditions. In the context of nucleic acid hybridization, two nucleotide sequences being compared may be designated as a probe and a target. A probe is a reference nucleic acid molecule, and a target is a test nucleic acid molecule, often found within a heterogeneous population of nucleic acid molecules. In this respect, a target sequence is synonymous with a test sequence.

In some embodiments of the aspects of the invention, the polynucleotides include primers and primer pairs that allow specific amplification of the disclosed polynucleotides or of any specific parts thereof, and probes that selectively or specifically hybridize to nucleic acid molecules of the invention or to any part thereof. Primers may also be used as probes and can be labeled with a detectable marker, such as, for example, a radioisotope, fluorescent compound, bioluminescent compound, a chemiluminescent compound, metal chelator or enzyme. A particular nucleotide sequence employed for hybridization studies or assays may include probe sequences that are complementary to at least about 14-40 nucleotide sequence of a nucleic acid molecule described herein. Probes may comprise 14-20 nucleotides, or even longer where desired, such as 30, 40, 50, 60, 100, 200, 300, or 500 nucleotides or up to the full length of SEQ ID NO: 1, 11 or SEQ ID NO: 9. Such fragments may be readily prepared, for example by chemical synthesis of the fragment, by application of nucleic acid amplification technology, or by introducing selected sequences into recombinant vectors for recombinant production.

Specific hybridization refers to the binding, duplexing, or hybridizing of a molecule only to a particular nucleotide sequence under stringent conditions when that sequence is present in a complex nucleic acid mixture (e.g., total cellular DNA or RNA). Specific hybridization may accommodate mismatches between the probe and the target sequence depending on the stringency of the hybridization conditions.

Stringent hybridization conditions and stringent hybridization wash conditions in the context of nucleic acid hybridization experiments, such as Southern and Northern blot analysis, are both sequence- and environment-dependent. Longer sequences hybridize specifically at higher temperatures. An extensive guide to the hybridization of nucleic acids is found in Tijssen, *Laboratory Techniques in Biochemistry and Molecular Biology—Hybridization with Nucleic Acid Probes*, Part I, Chapter 2, Elsevier, New York, N.Y. (1993). Generally, stringent hybridization and wash conditions are selected to be about 5° C. below the thermal melting point for the specific sequence at a defined ionic strength and pH. Typically, under stringent conditions a probe will hybridize specifically to its target sequence, but not to other sequences.

The Tm is the temperature (under defined ionic strength and pH) at which 50% of the target sequence hybridizes to a perfectly matched probe. Stringent conditions are selected to be equal to the Tm for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent conditions is 15 minutes in 0.1×SSC at 65° C., whereas an example of stringent wash conditions is 15 minutes in 0.2×SSC buffer at 65° C. See Sambrook et al., *Molecular Cloning: A Laboratory Manual*, Cold Spring Harbor Laboratory Press, Cold Spring Harbor, N.Y. (1989). Typically, a high stringency wash is preceded by a low stringency wash to remove background probe signal. An example of medium stringency conditions for a duplex of more than about 100 nucleotides is 15 minutes in 1×SSC at 45° C. An example of low stringency for a duplex of more than about 100 nucleotides is 15 minutes in 4 to 6×SSC at 40° C. For short probes (e.g., about 10 to 50 nucleotides), stringent conditions typically involve salt concentrations of less than about 1M Na+ ion, typically about 0.01 to 1M Na+ ion concentration (or other salts) at pH 7.0-8.3, and the temperature is typically at least about 30° C. Stringent conditions may also be achieved with the addition of destabilizing agents, such as formamide. Additional variations of these conditions will be readily apparent to those skilled in the art.

Stringency conditions may be selected such that an oligonucleotide that is perfectly complementary to the coding oligonucleotide hybridizes the coding oligonucleotide with at least about 5 to 10 times higher signal to noise ratio than the ratio for hybridization of the perfectly complementary oligonucleotide to a nucleic acid encoding a transcription factor know in the art. It may be desirable to select conditions for a particular assay such that a higher signal to noise ratio (e.g., about 15× or more) is obtained. Accordingly, a subject nucleic acid will hybridize to a unique coding oligonucleotide with at least 2 times (2×) or greater signal to noise ratio as compared to hybridization of the coding oligonucleotide to a nucleic acid encoding a known polypeptide. The particular signal will depend on the label used in the relevant assay, e.g., a fluorescent label, a calorimetric label, a radioactive label, or the like. Labeled hybridization or PCR probes for detecting related polynucleotide sequences may be produced by oligolabeling, nick translation, end-labeling, or PCR amplification using a labeled nucleotide.

A further indication that two nucleotide sequences are substantially identical is that proteins encoded by the polynucleotides are substantially identical, share an overall three-dimensional structure, or are biologically functional equivalents. Nucleic acid molecules that do not hybridize to teach other under stringent conditions are still substantially identical if the corresponding proteins are substantially identical. This may occur, for example, when two nucleotide sequences comprise conservatively substituted variants as permitted by the genetic code. Conservatively substituted variants refer to nucleotide sequences having degenerate codon substitution wherein the third position of one or more (or all) codons is/are substituted with mixed-base and/or deoxyinosine residues. See Batzer et al., *Nucleic Acids Res*, 19:5081 (1991), Ohtsuka et al., *J. Biol. Chem.* 260:2605-2608 (1991); and Rossolini et al., *Mol. Cell. Probes* 8:91-98 (1994).

Methods using manual alignment of sequences similar or homologous to one or more polynucleotide sequences or one or more polypeptides encoded by the polynucleotide sequences may be used to identify regions of similarity and conserved domains. Such manual methods are well known to persons skilled in the art and can include, for example, comparisons of the tertiary structure between a polypeptide sequence encoded by a polynucleotide that comprises a known function with a polypeptide sequence encoded by a nucleotide sequence that has a function not yet determined. Examples of tertiary structure may include predicted alpha helices, beta-sheets, amphipathic helices, leucine zipper motifs, zinc finger motifs, proline-rich regions, cysteine repeat motifs, and the like.

In embodiments of the aspects of the invention, the polynucleotides may include polynucleotides encoding the WRKY76 transcription factor polypeptide (protein) of SEQ ID NO: 2 or a variant thereof, such as a WRKY76 transcription factor polypeptide derived from the full-length amino acid sequence of SEQ ID NO: 2 containing one or more substitutions, deletions and/or additions of amino acid residues. The polynucleotides may therefore also include polynucleotides encoding a functional variant WRKY76 polypeptide as described herein, for example SEQ ID NO: 12.

Orthologs and paralogs of transcription factor polypeptides described herein may be cloned according to conventional methods. These may have at least 80%, 85%, 90 or 95% sequence identity to HaWRKY76. For example, cDNAs can be cloned using mRNA from a plant cell or tissue that expresses one of the transcription factor polypeptides described herein. Appropriate mRNA sources may be identified by interrogating Northern blots with probes designed from amino acid sequences within the scope of the present disclosure, after which a library is prepared from the mRNA obtained from a positive cell or tissue. Transcription factor-encoding cDNA is then isolated by, for example, PCR, using primers designed from a transcription factor gene sequence disclosed herein, or by probing with a partial or complete cDNA or with one or more sets of degenerate probes based on sequences disclosed herein. The cDNA library may be used to transform plant cells, as discussed further below, and expression of the cDNAs of interest is detected using, for example, methods known or described herein, such as microarrays, Northern blots, quantitative PCR, or any other technique for monitoring changes in expression. Genomic clones may also be isolated using similar techniques.

In embodiments of the aspects of the invention, the polynucleotides may be cloned, synthesized, altered, mutagenized, or combinations thereof. A nucleic acid can be isolated using standard molecular biology techniques and the sequence information provided herein. Standard recombinant DNA and molecular cloning techniques used to isolate nucleic acids are known to persons skilled in the art. In embodiments, a nucleic acid molecule can be amplified using cDNA or, alternatively, genomic DNA, as a template and appropriate oligonucleotide primers according to standard PCT amplification techniques. The nucleic acid molecule so amplified can be cloned into an appropriate vector and characterized by DNA sequence analysis.

WRKY76 Transcription Factor Polypeptides (Proteins)

Embodiments according to the various aspects of the invention also relate to isolated WRKY76 transcription factor polypeptides. The term polypeptides (proteins) refers to compounds made up of a single chain of amino acids joined by peptide bonds.

Representative polypeptides according to embodiments of the various aspects of the invention include the full-length amino acid sequence of SEQ ID NO: 2, and variants thereof, including substantially identical polypeptides. One variant is shown in SEQ ID NO: 12 Substantially identical polypeptides have amino acid sequences that vary from the full-length amino acid sequence of SEQ ID NO: 2 by one or more deletions, substitutions, or additions, the net of which is retained biological function of the WRKY76 polypeptide. In embodiments, the WRKY76 polypeptides have at least 80% sequence identity with the full-length amino acid sequence of SEQ ID NO: 2 as described herein, or by visual inspection. In embodiments, the WRKY76 polypeptides have at least 85% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity with the full-length amino acid sequence of SEQ ID NO: 2.

In some embodiments, substantially identical polypeptides contain at least one of the following: (a) proline as the amino acid corresponding to position 270 of the full-length amino acid sequence of SEQ ID NO: 2 or a variant thereof, for example SEQ ID NO: 12; (b) proline as the amino acid corresponding to position 260 of the full-length amino acid sequence of SEQ ID NO: 2 or a variant thereof, for example SEQ ID NO: 12; (c) proline as the amino acid corresponding to position 87 of the full-length amino acid sequence of SEQ ID NO: 2 or a variant thereof, for example SEQ ID NO: 12; (d) serine as the amino acid corresponding to position 123 of the full-length amino acid sequence of SEQ ID NO: 2 or a variant thereof, for example SEQ ID NO: 12; (e) leucine as the amino acid corresponding to position 14 of the full-length amino acid sequence of SEQ ID NO: 2 or a variant thereof, for example SEQ ID NO: 12; (f) leucine as the amino acid corresponding to position 22 of the full-length amino acid sequence of SEQ ID NO: 2 or a variant thereof, for example SEQ ID NO: 12; and (g) serine as the amino acid corresponding to position 23 of the full-length amino acid sequence of SEQ ID NO: 2 or a variant thereof, for example SEQ ID NO: 12. In particular, in one aspect, the invention relates to an isolated polypeptide comprising a sequence having at least 80% sequence identity with the full-length amino acid sequence of SEQ ID NO: 2, the polypeptide sequence containing at least one of:

(a) proline as the amino acid corresponding to position 270 of the full-length amino acid sequence of SEQ ID NO: 2 or a variant thereof, for example SEQ ID NO: 12;

(b) proline as the amino acid corresponding to position 87 of the full-length amino acid sequence of SEQ ID NO: 2 or a variant thereof, for example SEQ ID NO: 12;

(c) proline as the amino acid corresponding to position 260 of the full-length amino acid sequence of SEQ ID NO: 2 or a variant thereof, for example SEQ ID NO: 12;

(d) serine as the amino acid corresponding to position 123 of the full-length amino acid sequence of SEQ ID NO: 2 or a variant thereof, for example SEQ ID NO: 12;

(e) leucine as the amino acid corresponding to position 14 of the full-length amino acid sequence of SEQ ID NO: 2 or a variant thereof, for example SEQ ID NO: 12;

(f) leucine as the amino acid corresponding to position 22 of the full-length amino acid sequence of SEQ ID NO: 2 or a variant thereof, for example SEQ ID NO: 12; and (g) serine as the amino acid corresponding to position 23 of the full-length amino acid sequence of SEQ ID NO: 2 or a variant thereof, for example SEQ ID NO: 12.

Substantially identical sequences according to the embodiments of the various aspects of the invention may be polymorphic sequences, i.e., alternative sequences or alleles in a population in which the allelic difference may be as small as one base pair. Substantially identical polynucleotides may also comprise mutagenized sequences, including sequences comprising silent mutations. A mutation may comprise one or more residue changes, a deletion of one or more residues, or an insertion of one or more additional residues. In some embodiments, polypeptide variants can be functional fragments of the WRKY76 transcription factor polypeptide of SEQ ID NO: 2. Functional polypeptides may include amino acid sequences that are longer than the sequences described herein. For example, one or more amino acids may be added to the N-terminus or C-terminus of a polypeptide. Such additional amino acids may be employed in a variety of applications, including (but not limited to) purification applications. Methods of preparing elongated polypeptides are known to persons skilled in the art. In one embodiment, the isolated polypeptide comprises or consists of SEQ ID NO:2 or 12.

WRKY76 transcription factor polypeptides described herein and according to the various aspects of the invention may comprise naturally occurring amino acids, synthetic amino acids, genetically encoded amino acids, non-genetically encoded amino acids, and combinations thereof.

WRKY76 polypeptides described herein and according to the various aspects of the invention may also include polypeptides comprising amino acids that are conservatively substituted variants of the full-length amino acid sequence of SEQ ID NO: 2. A conservatively substituted variant refers to a polypeptide comprising an amino acid in which one or more residues have been conservatively substituted with a functionally similar residue. Examples of conservative substitutions include the substitution of one non-polar (hydrophobic) residue (e.g., isoleucine, valine, leucine, or methionine) for another, such as between arginine and lysine, between glutamine and asparagine, between glycine and serine; the substitution of one basic residue (e.g., lysine, arginine, or histidine) for another; or the substitution of one acidic residue (e.g., aspartic acid or glutamic acid) for another.

Isolated polypeptides according to embodiments may be purified and characterized using a variety of standard techniques that are known to persons skilled in the art. See Schröder et al., *The Peptides*, Academic Press, New York, N.Y. (1965).

Regulatory Elements

The invention also relates to a vector or nucleic acid construct comprising a polynucleotide as described above. In one embodiment, said isolated polynucleotide comprises or consists of SEQ ID NO: 1 or 11. In another aspect, the invention relates to a recombinant expression cassette comprising a polynucleotide as described above, wherein the polynucleotide is operably linked to a promoter. The polynucleotide may be in a sense or antisense orientation. In one embodiment, said isolated polynucleotide comprises or consists of SEQ ID NO: 1. In another aspect, the invention relates to recombinant expression cassette comprising an isolated polynucleotide operably linked to a promoter, wherein the polynucleotide is a member selected from the group consisting of:
 (a) a polynucleotide that encodes the polypeptide of SEQ ID NO: 2 or 12; and
 (b) the polynucleotide of SEQ ID NO: 1 or a variant thereof, for example SEQ ID NO: 11.

A regulatory element generally can increase or decrease the amount of transcription of a nucleotide sequence operatively linked to the element with respect to the level at which the nucleotide sequence would be transcribed absent the regulatory element.

In some embodiments of the aspects of the invention, stress-regulated regulatory elements, which regulate expression of an operatively linked nucleotide sequence in a plant in response to a stress condition, are also provided. The plant stress-regulated regulatory elements may be isolated from a polynucleotide sequence of a plant stress-regulated gene. Specifically, the plant stress-regulated regulatory elements may be isolated from a polynucleotide sequence of the WRKY76 gene comprising the nucleotide sequence of SEQ ID NO: 1, or a variant thereof or comprising a nucleotide sequence that is functionally equivalent to the full-length nucleotide sequence of SEQ ID NO: 1, for example SEQ ID NO: 11. Thus, a WRKY76 promoter, for example the HaWRKY76 promoter, may be used. This can be selected from SEQ ID NO: 10 or a sequence with at least 80%, 85%, 90%, or 95% sequence identity with SEQ ID NO: 10.

Methods for identifying and isolating a stress-regulated regulatory element from the polynucleotides, or genomic DNA clones corresponding thereto, are known to persons skilled in the art. For example, methods of making deletion constructs or linker-scanner constructs can be used to identify nucleotide sequences that are responsive to a stress condition. Generally, such constructs include a reporter gene operatively linked to the sequence to be examined for regulatory activity. By performing such assays, a plant stress-regulated regulatory element can be defined within a sequence of about 500 nucleotides or fewer, generally at least about 200 nucleotides or fewer, or about 50 to 100 nucleotides. Preferably, the minimal (core) sequence required for regulating a stress response of a plant is identified. The nucleotide sequences of the genes of a cluster can also be examined using a homology search engine to identify sequences of conserved identity, particularly in the nucleotide sequence upstream of the transcription start site.

Regulatory elements, as described and defined herein, may be isolated from a naturally occurring genomic DNA sequence or can be synthetic (e.g., a synthetic promoter). The regulatory elements can be constitutively expressed so as to maintain gene expression at a relative level of activity (basal level), or can be regulated. Constitutively expressed regulatory elements can be expressed in any cell type, or can be tissue specific (expressed only in particular cell types), or phase specific (expressed only during particular developmental or growth stages of a plant cell). Regulatory elements (e.g., a tissue specific, phase specific, or inducible regulatory element) useful in constructing a recombinant polynucleotide or in practicing methods described herein include regulatory elements that are found in a plant genome. In some embodiments, the regulatory elements may be from an organism other than a plant, such as a plant or animal virus, or an animal or other multicellular organism.

In some embodiments, a regulatory element that is a promoter element is provided. Particularly useful promoters include, but are not limited to, constitutive, inducible, temporally regulated, developmentally regulated, spatially-regulated, chemically regulated, stress-responsive, tissue-specific, viral and synthetic promoters. Promoter sequences are generally understood to be strong or weak. A strong promoter provides for a high level of gene expression, whereas a weak promoter provides for a low level of gene expression. An inducible promoter is a promoter that allows gene expression to be turned on and off in response to an exogenously added agent, or to an environmental or developmental stimulus. An isolated promoter sequence that is a strong promoter for heterologous nucleic acid is typically advantageous because it provides for a sufficient level of gene expression to allow for easy detection and selection of transformed cells, while providing a high level of gene expression when desired.

Several domains within a plant promoter region are necessary for the full function of the promoter. The first of these domains within the promoter region lies immediately upstream of the structural gene and forms the "core promoter region" containing consensus sequences, normally 70 base pairs immediately upstream of the gene. The core promoter region represents a transcription initiation sequence that defines the transcription start point for the structural gene. The presence of the core promoter region defines a sequence as being a promoter; that is, if the region is absent, the promoter is non-functional. The core promoter region on its own is, however, insufficient to provide full promoter activity. A series of regulatory sequences upstream of the core constitute the remainder of the promoter. These regulatory sequences determine expression levels, the spatial and temporal patterns of expression and, for the specific subset of promoters, the expression level under inductive conditions (e.g., light, temperature, chemicals, hormones).

To define a minimal promoter region, a DNA segment representing the promoter region is removed from the 5'-region of the gene of interest and operably linked to the coding sequence of a marker (reporter) gene by recombinant DNA techniques known to persons skilled in the art. The reporter gene is operably linked downstream of the promoter, so that transcripts initiating at the promoter proceed through the reporter gene. Reporter genes generally encode proteins that are easily measured. The construct containing the reporter gene under the control of the promoter is then introduced into an appropriate plant cell by transfection techniques known to persons skilled in the art. The level of enzyme activity corresponds to the amount of enzyme produced, which, in turn, reveals the level of expression from the promoter of interest. This level of expression can be compared to that achieved using other promoters to determine the relative strength of the promoter under study. To ensure that the expression level is due to the promoter, rather than the stability of the mRNA, the level of the reporter mRNA can be measured directly (e.g., by Northern blot analysis).

Once enzyme activity is detected, mutational and/or deletional analyses may be performed to determine the minimal region and/or sequences required to initiate transcription. Sequences may be deleted at the 5'-end of the promoter region and/or at the 3'-end of the promoter region, and nucleotide substitutions may be introduced. These constructs may then be introduced into cells and their activity determined.

The promoter selection depends on the temporal and spatial requirements for expression, as well as on the target species. In some embodiments, expression in multiple tissues may be desirable, while in others, tissue-specific (e.g., leaf-specific, seed-specific, petal-specific, anther-specific, or pith-specific) expression is desirable. Although promoters from dicotyledons have been shown to be operational in monocotyledons, and vice versa, dicotyledonous promoters are ideally selected for expression in dicotyledons, and monocotyledonous promoters are ideally selected for expression in monocotyledons. There is no restriction as to the origin or source of the promoter selected; it is sufficient that the selected promoter is operational in driving the expression of a nucleotide sequence described herein in the particular cell. That is, the promoter used in embodiments of the present disclosure may be any nucleotide sequence that shows transcriptional activity in the target (host) plant (cell, seed, etc.).

Accordingly, in embodiments, the promoter may be native or analogous, or foreign or heterologous, to the plant host and/or to the DNA sequence disclosed herein. Where the promoter is native or endogenous to the plant host, it is intended that the promoter is found in the native plant into which the promoter is introduced. Where the promoter is foreign or heterologous to the DNA sequence disclosed herein, the promoter is not the native or naturally occurring promoter for the operably linked DNA sequence disclosed herein. The promoter selected in embodiments may be "inducible" or "constitutive." An inducible promoter is a promoter that is under environmental control, whereas a constitutive promoter is a promoter that is active under most environmental conditions. Moreover, the promoter may be naturally-occurring, composed of portions of various naturally-occurring promoters, or partially or totally synthetic. Guidance for the design of promoters is provided by studies of promoter structure in Harley et al., *Nucleic Acids Res.* 15:2343-61 (1987). Additionally, the location of the promoter relative to the transcription start position may be optimized. See e.g., Roberts et al., *Proc. Natl. Acad. Sci.* 76:760-764, USA (1979).

For example, suitable constitutive promoters for use in plants according to the present disclosure may include promoters from plant viruses, such as the peanut chlorotic streak caulimovirus (PClSV) promoter, the 35S promoter from cauliflower mosaic virus (CaMV), promoters of *Chlorella* virus methyltransferase genes, the full-length transcript promoter from figwort mosaic virus (FMV); the promoters from such genes as rice actin, ubiquitin, pEMU, MAS, maize H4 histone, *Brassica napus* ALS4; and promoters of various *Agrobacterium* genes. See e.g., Odell et al., *Nature* 313:810-812 (1985); McElroy et al., *Plant Cell* 2:163-171 (1990); Christensen et al., *Plant Mol. Biol.* 12:619-632 (1989); Christensen et al., *Plant Mol. Biol.* 18:675-689 (1992); Last et al., *Theor. Appl. Genet.* 81:581-588 (1991); Velten et al., *EMBO J.* 3:2723-27310 (1984); Lepetit et al., *Mol. Gen. Genet.* 231:276-285 (1992); and U.S. Pat. Nos. 4,771,002; 5,102,796; 5,182,200; 5,428,147; 5,850,019; 5,563,328; 5,378,619.

Suitable inducible promoters for use in plants according to the present disclosure may include, for example, the promoter from the ACE1 system that responds to copper, the promoter of the maize In2 gene that responds to benzenesulfonamide herbicide safeners, and the promoter of the Tet repressor from Tn10. See Mett et al., *Proc. Natl. Acad. Sci.,* 90:4567-4571, USA (1993); Hershey et al., *Mol. Gen. Genet.* 227:229-237 (1991); and Gatz et al., *Mol. Gen. Genet.* 243:32-38 (1994). Another inducible promoter that may be used in plants described herein is one that responds to an inducting agent to which plants do not normally respond. An inducible promoter of this type may be the inducible promoter from a steroid hormone gene, the transcriptional activity of which is induced by glucocorticosteroid hormone, or the recent application of a chimeric transcription activator, SVE, for use in an estrogen receptor-based inducible plant expression system activated by estradiol. See Schena et al., *Proc. Natl. Acad. Sci.* 88:104-21 (1991); Zuo et al., *Plant J.* 24:265-273 (2000). Other inducible promoters suitable for use in embodiments may be selected from promoters described in EP 332104, PCT International Publication Nos. WO93/21334 and WO 97/06269. Promoters composed of portions of other promoters and partially or totally synthetic promoters may also be used. See e.g., Ni et al., *Plant J.* 7:661-676 (1995); and PCT International Publication No. 95/14098 (describing use of such promoters in plants).

In embodiments, the promoter may be a WRKY76-specific promoter cloned according to methods described herein.

The promoter may include, or be modified to include, one or more enhancer elements to thereby provide for higher levels of transcription. Examples of suitable enhancer elements for use in plants described herein include, for example, the PClSV enhancer element, the CaMV 35S enhancer element and the FMV enhancer element. See Maiti et al., *Transgenic Res.* 6:143-156 (1997); PCT International Publication No. WO 96/23898; and U.S. Pat. Nos. 5,850,019; 5,106,739; and 5,164,316.

Expression Constructs

Embodiments include recombinant constructs comprising one or more of the polynucleotide sequences described herein. The constructs typically comprise a vector, such as a plasmid, a cosmid, a phage, a virus, a bacterial artificial chromosome (BAC), a yeast artificial chromosome (YAC), or the like, into which a polynucleotide sequence as described herein has been inserted, in a forward or reverse orientation. In some embodiments, the constructs may further comprise regulatory sequences, including, e.g., a promoter that is operably linked to the sequence. Vectors and promoters suitable for recombinant constructs of the present disclosure may include those generally known to persons having skill in the art and/or described herein.

Constructs suitable for use in embodiments may contain a "signal sequence" or "leader sequence" to facilitate co-translational or post-translational transport of the polypeptide of interest to certain intracellular structures, such as the chloroplast (or other plastid), endoplasmic reticulum, or Golgi apparatus, or to be secreted. Such sequences include leader sequences targeting transport and/or glycosylation by passage into the endoplasmic reticulum, vacuoles, plastids including chloroplasts, mitochondria, and the like. For example, the constructs may be engineered to contain a signal peptide to facilitate transfer of the peptide to the endoplasmic reticulum. A signal sequence is known or suspected to result in co-translational or post-translational peptide transport across the cell membrane. In eukaryotes, this typically involves secretion into the Golgi apparatus, with some resulting glycosylation. Leader sequence refers to any sequence that, when translated, results in an amino acid sequence sufficient to trigger co-translational transport of the peptide chain to a sub-cellular organelle. Plant expression cassettes may also contain an intron, such that mRNA processing of the intron is required for expression Suitable constructs may also contain 5' and 3' untranslated regions. A 3' untranslated region is a polynucleotide located downstream of a coding sequence. Polyadenylation signal sequences and other sequences encoding regulatory signals capable of affecting the addition of polyadenylic acid tracts to the 3' end of the mRNA precursor or the 3' untranslated regions. A 5' untranslated region is a polynucleotide located upstream of a coding sequence.

Any of the sequences described herein may be incorporated into a cassette or vector for expression in plants. Expression vectors suitable for stable transformation of plant cells or for the establishment of transgenic plants are known by persons skilled in the art. See e.g., Weissbach and Weissbach, *Methods for Plant Molecular Biology*, Academic Press, (1989); and Gelvin et al., *Plant Molecular Biology Manual*, Kluwer Academic Publishers (1990). Specific examples may include those derived from a Ti plasmid of *Agrobacterium tumefaciens* and those described for use in dicotyledonous plants in Herrera-Estrella et al., *Nature* 303: 209 (1983) and Klee, *Bio/Technol.* 3:637-642 (1985). In embodiments, non-Ti vectors may be used to transfer the DNA into monocotyledonous plants and cells by using free DNA delivery techniques. Such methods may involve, for example, the use of liposomes, electroporation, microprojectile bombardment, silicon carbide whispers, and viruses.

The termination region may be native to the transcriptional initiation region, the sequence described herein, or may be derived from another source. Suitable termination regions may be derived from the Ti-plasmid of *A. tumefaciens*, such as the octopine synthase and nopaline synthase termination regions, or the termination region of a plant gene, such as soybean storage protein. See Guerineau et al., *Mol. Gen. Genet.* 262:141-144 (1991); Proudfoot, *Cell* 64:671-674 (1991); Sanfacon et al., *Genes Dev.* 5:141-149 (1991); Mogen et al., *Plant Cell* 2:1261-1272 (1990); Munroe et al., *Gene* 91:151-158 (1990); Ballas et al., *Nucleic Acids Res.* 17:7891-7903 (1989); and Joshi et al., *Nucleic Acids Res.* 15:9627-9639 (1987). These vectors are plant integrating vectors in that upon transformation, the vectors integrate a portion of vector DNA into the genome of the host plant. An example of a vector useful in embodiments is plasmid pBI121.

Where appropriate, the vector and WRKY76 transcription factor sequences disclosed herein may be optimized for increased expression in the transformed host cell. That is, the sequences may be synthesized using host cell-preferred codons for improved expression, or may be synthesized using codons at a host-preferred codon usage frequency. Generally, the GC content of the polynucleotide will be increased. See e.g., Campbell et al., *Plant Physiol.* 92:1-11 (1990). Methods for synthesizing host-preferred polynucleotides are known by persons skilled in the art. See e.g., Murray et al., *Nucleic Acids Res.* 17:477-498 (1989); U.S. Patent Application Publications Nos. 2004/0005600 and 2001/0003849; and U.S. Pat. Nos. 6,320,100; 6,075,185; 5,380,831; and 5,436,391, the entire disclosures of which are incorporated by reference herein.

For example, polynucleotides of interest can be targeted to the chloroplast for expression. In this manner, where the polynucleotide of interest is not directly inserted into the chloroplast, an expression cassette according to some embodiments may additionally contain a polynucleotide encoding a transcription factor polypeptide to direct the nucleotide of interest to the chloroplasts. Such transit peptides are known by persons skilled in the art. See e.g., Von Heijne et al., *Plant Mol. Biol. Rep.* 9:104-126 (1991); Clark et al., *J. Biol. Chem.* 264:17544-17550 (1989); Della-Cioppa et al., *Plant Phsyiol.* 84:965-968 (1987); Romer et al., *Biochem. Biophys. Res. Commun.* 196:1414-1421 (1993); and Shah et al., *Science* 233:478-481 (1986). The polynucleotides of interest to be targeted to the chloroplast may further be optimized for expression in the chloroplast to account for differences in codon usage between the plant nucleus and this organelle. In this manner, the polynucleotides of interest may be synthesized using chloroplast-preferred codons. See U.S. Pat. No. 5,380,831, the entire disclosure of which is incorporated by reference herein.

In embodiments, one or more plant expression cassette (i.e., a WRKY76 transcription factor open reading frame operably linked to a promoter) may be inserted into a plant transformation vector, which allows for the transformation of DNA into a cell. Such expression cassettes may be organized into more than one vector DNA molecule.

Plant expression vectors suitable for use in embodiments may comprise one or more DNA vector(s) for achieving plant transformation. For example, it is common practice for persons skilled in the art to utilize plant transformation vectors that include one or more cloned plant coding sequences (genomic or cDNA) under the transcriptional control of 5' and 3' regulatory sequences as a dominant selectable marker. Such plant transformation vectors typically also contain a promoter, a transcription initiation start site, an RNA processing signal, a transcription termination site, and/or a polyadenylation signal.

Binary vectors are plant transformation vectors that utilize two non-contiguous DNA vectors to encode all requisite cis- and trans-acting functions for transformation of plant cells. See Hellens et al., *Trends in Plant Sicence* 5:446-451 (2000). Binary vectors, as well as vectors with helper plasmids, are most often used for *Agrobacterium*-mediated transformations, in which the size and complexity of DNA segments needed to achieve efficient transformation is large, and in which it is therefore advantageous to separate functions among separate DNA molecules. Binary vectors also typically contain a plasmid vector that contains the cis-acting sequence required for T-DNA transfer (such as left border and right border), a selectable marker that is engineered to be capable of expression in a plant cell, and a polynucleotide of interest (i.e., a polynucleotide engineered to be capable of expression in a plant cell for which generation of transgenic plants is desired). Sequences required for bacterial replication may also be present on this plasmid vector. The cis-acting sequences are arranged in a fashion to allow for efficient transfer into plant cells and expression therein. For example, a selectable marker sequence and a sequence of interest are typically located between the left and right borders. Often a second plasmid vectors the trans-acting factors that mediate T-DNA transfer from *Agrobacterium* to the target (host) plant cells. This plasmid typically contains virulence functions (*Vir* genes) that allow infection of plant cells by *Agrobacterium*, and transfer of DNA by cleavage at border sequences and vir-mediated DNA transfer, as understood by persons skilled in the art. See e.g., Hellens et al., *Trends in Plant Science* 5:446-451 (2000). Several types of *Agrobacterium* strains (e.g., LBA4404, GV3101, EHA101, EHA105, etc.) may be used for plant transformation. The second plasmid vector is typically not necessary for introduction of polynucleotides into plants by other methods, such as by microprojection, microinjection, electroporation, etc.

In some embodiments, expression vectors include RNA processing signals that can be positioned within, upstream or downstream of the coding sequence. The expression vectors may include additional regulatory sequences from the 3'-untranslated region of plant genes. Initiation signals may also be used to aid in efficient translation of coding sequences. These signals can include, e.g., an ATG initiation codon and adjacent sequences. In cases where a coding sequence, its initiation codon and upstream sequences are inserted into the appropriate expression vector, no additional translational control signals may be needed. However, in cases where only coding sequences, or a portion thereof, are inserted, exogenous transcriptional control signals including the ATDG initiation codon can be separately provided. The initiation codon is provided in the correct reading frame to facilitate transcription. Exogenous transcription elements and initiation codons can be of various origins, both natural and synthetic. The efficiency of expression can be enhanced by including enhancers appropriate for the cell system in use.

In embodiments where co-suppression of a gene is desired, vectors in which RNA encoded by a transcription factor or transcription factor homologue cDNA is overexpressed may be used to obtain co-suppression of a corresponding endogenous gene. See e.g., U.S. Pat. No. 5,231,020. Such co-suppression (also termed "sense suppression") does not require that the entire transcription factor cDNA be introduced into the plant cells, nor does it require that the introduced sequence is identical to the endogenous transcription factor gene of interest. However, as with antisense suppression, the suppressive efficiency will be enhanced as the specificity of hybridization is increased.

Embodiments include host (i.e., target) cells transduced with vectors described herein, and the production of polypeptides by recombinant techniques. Host cells are genetically engineered (i.e., nucleic acids are introduced by transduction, transformation or transfection) with the vectors, which may be, e.g., a cloning vector or an expression vector comprising the relevant nucleic acids described herein. The vector may optionally be, for example, a plasmid, a viral particle, a phage, a naked nucleic acid, etc.

Using polynucleotides disclosed herein, a protein may be expressed in a recombinantly engineered cell, such as a plant cell. Persons skilled in the art are knowledgeable about various expression systems available for expression of a polynucleotide encoding a protein according to embodiments described herein.

The expression of isolated polynucleotides encoding a protein according to embodiments described herein will typically be achieved by operably linking, for example, the DNA or cDNA to a promoter, followed by incorporation thereof into an expression vector. Typical expression vectors contain transcription and translation terminators, initiation sequences, and promoters useful for regulation of the expression of the DNA encoding a protein described herein. To obtain a high level of expression of a cloned gene, it is typically desirable to construct expression vectors that contain, at minimum, a strong promoter to direct transcription, a ribosome binding site for translational initiation, and a transcription/translation termination site. Persons having ordinary skill in the art would recognize that modifications could be made to a protein of the present disclosure without diminishing its biological activity.

Embodiments and aspects of the invention include an expression cassette. The expression cassette that comprises at least: (1) a constitutive, inducible, or tissue-specific promoter; and (2) a recombinant polynucleotide having a polynucleotide sequence, or a complementary polynucleotide sequence thereof, selected from the group consisting of a polynucleotide sequence encoding: (a) a polypeptide sequence having a transcription factor sequence as described herein; (b) a polynucleotide sequence selected from the transcription factor polynucleotides described herein; or sequence variants (e.g., allelic or splice variants) of the polynucleotide sequences referenced in (a) or (b) above, where the sequence variant encodes a polypeptide that regulates transcription.

Expression Hosts

The invention also relates to host cells comprising polynucleotides as described above, nucleic acid constructs, vectors or expression cassettes as described above. For example, the polynucleotide comprises or consists of SEQ ID NO:1 or a variant thereof, or SEQ ID NO:9 or a variant thereof. In one embodiment, the variant comprises or consists of SEQ ID NO:11.

In some embodiments, host cells are transduced with vectors as described herein. Host cells are genetically engineered (i.e., nucleic acids are introduced, transformed or transfected) with the vectors described herein, which may be, e.g., a cloning vector or an expression vector comprising the relevant nucleic acids disclosed herein. The vector is optionally a plasmid, a viral particle, a phage, a nucleic acid, etc. The engineered host cells can be cultured in conventional nutrient media modified as appropriate for activating promoters, selecting transformants or amplifying the relevant gene. The culture conditions, such as temperature, pH and the like, may be those previously used with the host cell selected for expression, and will be apparent to those skilled in the art.

The host cell may be a eukaryotic cell, such as a yeast cell or a plant cell, or the host cell may be a prokaryotic cell, such as a bacterial cell, for example *Agrobacterium*. In some embodiments, plant protoplasts may be suitable for use. In preferred embodiments, the host cell is a plant cell. A kit comprising such a host cell is also within the scope of the invention.

For example, the DNA fragments may be introduced into plant tissues, cultured plant cells or plant protoplasts by standard methods, including, e.g., electroporation, infection by viral vectors such as cauliflower mosaic virus (CaMV), high velocity ballistic penetration by small particles with the nucleic acid either within the matrix of small beads or particles, or on the surface, use of pollen as a vector, or using *Agrobacterium tumefaciens* or *A. rhizogenes* carrying a T-DNA plasmid in which DNA fragments are cloned. See Fromm et al., *Proc. Natl. Acad. Sci.* 82:8524-5828 (1985); Hohn et al., *Molecular Biology of Plant Tumors*, Academic Press, New York, N.Y. pp. 549-560 (1982); U.S. Pat. No. 4,407,956; Klein et al., Nature 327:70-73 (1987); PCT International Publication No. WO 85/01856. The T-DNA plasmid is transmitted to plant cells upon infection by *Agrobacterium tumefaciens*, and a portion is stably integrated into the plant genome. See Horsch et al., *Science* 233:496-498 (1984); and Fraley et al., *Proc. Natl. Acad. Sci.* 80:4803-4807 (1983).

The host cell may include a nucleic acid as described above. In some embodiments the host cell may include a nucleic acid that encodes a polypeptide according to embodiments described above, such that the cell expresses a polypeptide of interest as described herein. In some embodiments, the cell may include vector sequences or the like. As will be understood by persons skilled in the art, cells and transgenic plants that include any polypeptide or polynucleotide sequence described herein (e.g., produced by transduction of a vector described herein) represent embodiments within the scope of the present disclosure.

For long-term, high-yield production of recombinant proteins, stable expression may be used. Host cells transformed with a nucleotide sequence encoding a polypeptide as disclosed herein are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by persons skilled in the art, expression vectors according to embodiments containing polynucleotides that encode mature proteins can be designed with signal sequences that direct secretion of the mature polypeptides through a prokaryotic or eukaryotic cell membrane.

Some embodiments of the invention relate to recombinant expression of a WRKY76 transcription factor protein in a stable cell line. Methods for generating a stable cell line following transformation of a heterologous construct into a host cell are known in the art. The transformed cells, tissues, and plants are therefore understood to encompass not only the end product of a transformation process, but also transgenic progeny or propagated forms thereof.

Transgenic Plants and Production Thereof

Embodiments also relate to transgenic plants, methods of producing the transgenic plants, and methods for modifying plant traits or conferring desirable traits upon host plants to produce transgenic plants having improved stress tolerance and yield in standard growing conditions. Also within the scope of the invention are plants obtained or obtainable by the methods described herein.

Polynucleotides disclosed herein are favorably employed to produce transgenic plants with various traits or characteristics that have been modified in a desirable manner, e.g., to improve the seed characteristics of the plant. For example, altering the expression levels or patterns of one or more of the transcription factors (or transcription factor homologues) disclosed herein, as compared with the levels of the same protein found in a control wild-type plant, can be used to modify a plant's traits. Illustrative examples of trait modification and improved characteristics resulting from altering expression levels of the disclosed WRKY76 transcription factor sequences are explained in more detail in the various Examples below.

In some aspects of the invention, plants expressing a heterologous WRKY76 transcription factor, including plants that express a WRKY76 transcription factor at elevated levels, are provided. Still other aspects of the invention relate to the generation of plants with conditional or inducible expression of a WKKY transcription factor protein as disclosed herein.

Thus, in one further aspect, the invention relates to a transgenic plant comprising and expressing a nucleic acid construct, vector or expression cassette comprising a nucleic acid that encodes a WRKY76 transcription factor. For example, said nucleic acid comprises or consists of SEQ ID NO:1 or a variant thereof, for example SEQ ID NO:11, or SEQ ID NO:9, a functional variant or part thereof as defined above. In one embodiment, said polynucleotide has at least 80% sequence identity with the full-length nucleotide sequence of SEQ ID NO: 1 or a variant thereof, for example SEQ ID NO:11. In another embodiment, said polynucleotide has at least 80% sequence identity with the full-length nucleotide sequence of SEQ ID NO: 1 or a variant thereof, for example SEQ ID NO:11, wherein the polynucleotide contains at least one of:

(a) adenine as the nucleotide corresponding to position 817 of the full-length nucleotide sequence of SEQ ID NO: 1 or a variant thereof, for example SEQ ID NO:11;

(b) cytosine as the nucleotide corresponding to position 808 of the full-length nucleotide sequence of SEQ ID NO: 1 or a variant thereof, for example SEQ ID NO:11;

(c) cytosine as the nucleotide corresponding to position 33 of the full-length nucleotide sequence of SEQ ID NO: 1 or a variant thereof, for example SEQ ID NO:11;

(d) cytosine as the nucleotide corresponding to position 259 of the full-length nucleotide sequence of SEQ ID NO: 1 or a variant thereof, for example SEQ ID NO:11; and (e) guanine as the nucleotide corresponding to position 315 of the full-length nucleotide sequence of SEQ ID NO: 1 or a variant thereof, for example SEQ ID NO:11.

A plant according to the various aspects of the invention, including the transgenic plants, methods and uses described herein may be a monocot or a dicot plant. A dicot plant may be selected from the families including, but not limited to Asteraceae, Brassicaceae (e.g. *Brassica napus*), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae. For example, the plant may be selected from lettuce, sunflower, *Arabidopsis*, broccoli, spinach, water melon, squash, cabbage, tomato, potato, yam, *capsicum*, tobacco, cotton, okra, apple, rose, strawberry, alfalfa, bean, soybean, field (fava) bean, pea, lentil, peanut, chickpea, apricots, pears, peach, grape vine, bell pepper, chilli or *citrus* species. A monocot plant may, for example, be selected from the families Arecaceae, Amaryllidaceae or Poaceae. For example, the plant may be a cereal crop, such as maize, wheat, rice, barley, oat, *sorghum*, rye, millet, buckwheat, or a grass crop such as *Lolium* species or *Festuca* species, or a crop such as sugar cane, onion, leek, yam or banana. Also included are biofuel and bioenergy crops such as rape/canola, sugar cane, sweet *sorghum*, *Panicum virgatum* (switchgrass), linseed, lupin and willow, poplar, poplar hybrids, *Miscanthus* or gymnosperms, such as loblolly pine. Also included are crops for silage (maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed) and for amenity purposes (e.g. turf grasses for golf courses), ornamentals for public and private gardens (e.g. snapdragon, petunia, roses, geranium, Nicotiana sp.) and plants and cut flowers for the home (African violets, Begonias, chrysanthemums, geraniums, Coleus spider plants, Dracaena, rubber plant). Preferably, the plant is a crop plant. By crop plant is meant any plant which is grown on a commercial scale for human or animal consumption or use. In a preferred embodiment, the plant is a cereal. Most preferred plants are maize, rice, wheat, oilseed rape/canola, sorghum, soybean, sunflower, alfalfa, potato, tomato, tobacco, grape, barley, pea, bean, field bean, lettuce, cotton, sugar cane, sugar beet, broccoli or other vegetable brassicas or poplar.

The term "plant" as used herein encompasses whole plants, ancestors and progeny of the plants and plant parts, including seeds, fruit, shoots, stems, leaves, roots (including tubers), flowers, tissues and organs, wherein each of the aforementioned comprise the nucleic acid construct as described herein. The term "plant" also encompasses plant cells, suspension cultures, callus tissue, embryos, meristematic regions, gametophytes, sporophytes, pollen and microspores, again wherein each of the aforementioned comprises the nucleic acid construct as described herein.

The aspects of the invention also extend to products derived, preferably directly derived, from a harvestable part of such a plant, such as dry pellets or powders, oil, fat and fatty acids, starch or proteins. The invention also relates to food products and food supplements comprising the plant of the invention or parts thereof.

The transgenic plants show increased tolerance to stress conditions, for example abiotic and biotic stress compared to a control plant, for example a wild type plant. In particular, the plants show increased stress response to abiotic stress selected from drought or irrigation.

Plants expressing a heterologous WRKY76 transcription factor protein may be further modified at more than one WRKY76 transcription factor locus or at a locus other than a WRKY76 transcription factor locus to confer increased stress tolerance or another trait of interest.

The invention also relates to method for producing transgenic plants comprising introducing and expressing in a plant a polynucleotide, vector or expression cassette as described above or a polynucleotide encoding a WRKY76 polypeptide as described above. Such methods comprise generating from the plant cell a transgenic plant that expresses the polynucleotide. In one embodiment, the method comprises introducing and expressing a nucleic acid that comprises or consists of SEQ ID NO:1, a functional variant or part thereof as defined above. In one embodiment, said polynucleotide has at least 80% sequence identity with the full-length nucleotide sequence of SEQ ID NO: 1. In another embodiment, said polynucleotide has at least 80% sequence identity with the full-length nucleotide sequence of SEQ ID NO: 1 or a variant thereof, for example SEQ ID NO:11 or SEQ ID NO:9, wherein the polynucleotide contains at least one of:
  (a) adenine as the nucleotide corresponding to position 817 of the full-length nucleotide sequence of SEQ ID NO: 1 or a variant thereof, for example SEQ ID NO:11;
  (b) cytosine as the nucleotide corresponding to position 808 of the full-length nucleotide sequence of SEQ ID NO: 1 or a variant thereof, for example SEQ ID NO:11;
  (c) cytosine as the nucleotide corresponding to position 33 of the full-length nucleotide sequence of SEQ ID NO: 1 or a variant thereof, for example SEQ ID NO:11;
  (d) cytosine as the nucleotide corresponding to position 259 of the full-length nucleotide sequence of SEQ ID NO: 1 or a variant thereof, for example SEQ ID NO:11; and
  (e) guanine as the nucleotide corresponding to position 315 of the full-length nucleotide sequence of SEQ ID NO: 1 or a variant thereof, for example SEQ ID NO:11.

To prepare a plant expressing a heterologous WRKY76 transcription factor according to embodiments, the introduction of a WKKY polynucleotide disclosed herein may be accomplished by techniques known in the art, including, but not limited to, electroporation or chemical transformation. See e.g., Ausubel, Current Protocols in Molecular Biology, John Wiley and Sons, Inc., Indianapolis, Ind. (1994). Markers conferring resistance to toxic substances may also be used to identify transformed cells (having taken up and expressed the test polynucleotide sequence) from non-transformed cells (those not containing or not expressing the test polynucleotide sequence). The stable transformation of "transformed" or "transgenic" plants as used herein refers to the introduction of a polynucleotide construct into a plant, such that it integrates into the genome of the plant and is capable of being inherited by progeny thereof.

In general, plant transformation methods involve transferring heterologous DNA into target plant cells, followed by applying a maximum threshold level of appropriate selection to recover the transformed plant cells from an untransformed cell mass. Subsequently, the transformed cells are differentiated into shoots after being placed on a regeneration medium supplemented with a maximum threshold level of selecting agent (e.g., temperature, herbicide, etc.). The shoots are then transferred to a selective rooting medium for recovering the rooted shoot or plantlet. The transgenic plantlet is then grown into a mature plant that produces fertile seeds. A general description of techniques and methods for generating transgenic plants may be found in Ayres et al., CRC Crit. Rev. Plant Sci. 13:219-239 (1994), and Bommineni et al., Maydica 42:107-120 (1997).

In general, since the transformed material contains many cells, both transformed and non-transformed cells are present in any piece of subjected target callus, tissue, or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Therefore, molecular and biochemical methods may be used for confirming the presence of the integrated nucleotide(s) of interest in the genome of the transgenic plant. For example, selectable markers, such as enzymes resulting in a change of color or luminescent molecules (e.g., GUS and luciferase), antibiotic-resistant genes (e.g., gentamicin and kanamycin-resistance genes) and chemical-resistant genes (e.g., herbicide-resistance genes) may be used to confirm the integration of the nucleotide(s) of interest in the genome of the transgenic plant. Alternatively, particularly in considering the safety of the transgenic plants, the transformed plants can be selected under environmental stresses avoiding the incorporation of any selectable marker genes.

Transformation and regeneration of both monocotyledonous and dicotyledonous plant cells has become routine, and the selection of the most appropriate transformation technique can be readily determined by the person skilled in the art. The choice of method will typically vary based on the type of plant to be transformed, as persons skilled in the art will recognize the suitability of particular methods for given plant types. Suitable methods for use in embodiments may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Successful examples of modifications of plant characteristics by transformation with cloned sequences, which serve to illustrate current knowledge in the art and are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369; and 5,610,042.

The generation of transgenic plants according to embodiments may be performed by methods known to persons skilled in the art, including: introduction of heterologous DNA by *Agrobacterium* into plant cells (*Agrobacterium*-mediated transformation); bombardment of plant cells with heterologous foreign DNA adhered to particles; and various other non-particle direct-mediated methods, such as micro-injection, electroporation, application of Ti plasmid, Ri plasmid, or plant virus vector, and direct DNA transformation.

Generally, there are three types of conventional *Agrobacterium*-mediated transformation methods. The first method involves co-cultivation of *Agrobacterium* with cultured isolated protoplasts. This method requires an established culture system that allows culturing protoplasts and plant regeneration from cultured protoplasts. The second method involves transformation of cells or tissues with *Agrobacterium*. This method requires that the plant cells or tissues can be transformed by *Agrobacterium*, and that the transformed cells or tissues can be induced to regenerate into whole plants. The third method involves the transformation of seeds, apices or meristems with *Agrobacterium*. This method requires micropropagation.

The efficiency of *Agrobacterium*-mediated transformation methods may be enhanced by, e.g., including in the *Agrobacterium* culture a natural wound response molecule, such as acetosyringone (AS), which has been shown to enhance transformation efficiency with *Agrobacterium tumefaciens*. See Shahla et al., *Plant Molec. Biol.* 8:291-298 (1987). Alternatively, transformation efficiency may be enhanced by wounding the target tissue to be transformed by, e.g., punching, maceration, bombardment with microprojectiles, etc. See e.g., Bidney et al., *Plant Molec. Biol.* 18:301-313 (1992).

In some embodiments, plant cells may be transfected with vectors via particle bombardment (e.g., with a gene gun). Particle mediated gene transfer methods are known in the art, are commercially available, and include, e.g., the gas driven gene delivery instrument described in U.S. Pat. No. 5,584,807, the contents of which are incorporated by reference herein. This method involves coating the polynucleotide sequence of interest onto heavy metal particles, and accelerating the coated particles under the pressure of compressed gas for delivery to the target tissue.

In some embodiments, specific initiation signals may be used to achieve more efficient translation of sequences encoding a polypeptide described herein, such as, e.g., the ATG initiation codon and adjacent sequences. In cases where sequences encoding the polypeptide of interest, its initiation codon, and upstream sequences are inserted into the appropriate expression vector, no additional transcriptional or translational control signals may be needed. However in cases where only the coding sequence or a portion thereof is inserted, heterologous translational control signals that include the ATG initiation codon may be provided.

In addition to expression of nucleic acids disclosed herein as gene replacement or plant phenotype modification nucleic acids, disclosed nucleic acids may also be used for sense and anti-sense suppression of expression, e.g., to down-regulate expression of the disclosed nucleic acids, as a further mechanism for modulating plant phenotypes. That is, nucleic acids described herein, or subsequences or anti-sense sequences thereof, can be used to block expression of naturally occurring homologous nucleic acids. A variety of sense and anti-sense technologies is known in the art. See e.g., Lichtenstein and Nellen, *Antisense Technology: A Practical Approach*, IRL Press at Oxford University, Oxford, England (1997). In general, sense or anti-sense sequences are introduced into a cell, where they are optionally amplified, e.g., by transcription. Such sequences include both simple oligonucleotide sequences and catalytic sequences, such as ribozymes.

For example, the reduction or elimination of expression (i.e., a "knock-out") of a transcription factor or transcription factor homologue polypeptide in a transgenic plant, e.g., to modify a plant trait, can be obtained by introducing an antisense construct corresponding to the polypeptide of interest as a cDNA. For antisense suppression, the transcription factor or homologue cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA or interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described herein results in the production of RNA molecules that are the reverse complement of mRNA molecules transcribed form the endogenous transcription factor gene in the plant cell.

In some embodiments, suppression of endogenous transcription factor gene expression can also be achieved using a ribozyme. Ribozymes are RNA molecules that possess highly specific endoribonuclease activity. The production and use of ribozymes are disclosed in U.S. Pat. Nos. 4,987,071 and 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

In some embodiments, vectors in which RNA encoded by a transcription factor or transcription factor homologue cDNA is over-expressed may be used to obtain co-suppression of a corresponding endogenous gene, as described in U.S. Pat. No. 5,231,020. Such co-suppression (also termed "sense suppression") does not require that the entire transcription factor cDNA to be introduced into the plant cell, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation, can also be used to suppress expression of an endogenous transcription factor, thereby reducing or eliminating its activity and modifying one or more traits. Methods for producing such constructs are described in U.S. Pat. No. 5,583,021. Preferably, such constructs are made by introducing a premature stop codon into the transcription factor gene.

Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homologue gene. Plants containing a single transgene insertion even at the desired gene can be crossed to generate homozygous plants for the mutation. See Koncz et al., *Methods in Arabidopsis Research*, World Scientific (1992).

Alternatively, a plant phenotype can be altered by eliminating an endogenous gene, such as a transcription factor or transcription factor homologue, e.g., by homologous recombination. See Kempin et al., *Nature*, 389:820 (1997).

Polynucleotides and polypeptides disclosed herein can also be expressed in a plant in the absence of an expression cassette by manipulating the activity or expression level of the endogenous gene by other means, e.g., by ectopically expressing a gene by T-DNA activation tagging. See Ichikawa et al., *Nature* 390:698-701 (1997); and Kakimoto et al., *Science* 274:982-985 (1996). This method entails transforming a plant with a gene tag containing multiple transcriptional enhancers and, once the tag has inserted into the genome, expression of a flanking gene coding sequence becomes deregulated. As another example, the transcriptional machinery in a plant can be modified so as to increase transcription levels of a polynucleotide disclosed herein. See e.g., PCT International Publications Nos. WO 96/06166 and WO 98/53057 (describing modifications of DNA binding specificity of zinc finger proteins by changing particular amino acids in the DNA binding motif).

Following transformation, the plants are preferably selected using a dominant selectable marker incorporated into the transformation vector. After transformed plants are selected and grown to maturity, those plants showing a modified trait are identified. The modified train can be any of the traits described herein. Additionally, to confirm that the modified trait is due to changes in expression levels or activity of the polypeptide or polynucleotide disclosed herein, the mRNA expression may be analyzed using Northern blots, RT-PCR or microarrays, or protein expression using immunoblots, Western blots, or gel shift assays.

In some embodiments, the plants may be homozygous for the WRKY76 polynucleotide disclosed herein, i.e., a transgenic plant that contains two added sequences, one sequence at the same locus on each chromosome of a chromosome pair. A homozygous transgenic plant according to these embodiments can be obtained by sexually mating (selfing) an independent segregating transgenic plant that contains the added sequences disclosed herein, germinating some of the seed produced and analyzing the resulting plants produced for enhanced enzyme activity and/or increased plant yield relative to a control (native, non-transgenic) or an independent segregant transgenic plant. Persons skilled in the art will understand that two different transgenic plants may be mated to produce offspring that contain two independently segregating added heterologous polynucleotides.

Cells that have been transformed may be grown into plants in conventional ways. See e.g., McCormick et al., *Plant Cell Rep.* 5:81-84 (1986). The plants may be grown, and either pollinated with the same transformed strain or different strains, the resulting hybrid having constitutive expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved. In this manner, the present disclosure provides for transformed seeds (also referred to as transgenic seeds) having a polynucleotide as disclosed herein (e.g., an expression cassette as disclosed herein) stably incorporated into their genome.

Methods for Modulating a Plant Phenotype

In another aspect, the invention relate to a method for modulating a plant phenotype comprising introducing and expressing in a plant a polynucleotide, vector or expression cassette as described above or a polynucleotide encoding a WRKY76 polypeptide as described above. Such methods comprise generating from the plant cell a transgenic plant that expresses the polynucleotide. In one embodiment, the method comprises introducing and expressing a nucleic acid that comprises or consists of SEQ ID NO:1 or a variant thereof, for example SEQ ID NO:11 or SEQ ID NO:9, a functional variant or part thereof as defined above. In one embodiment, said polynucleotide has at least 80% sequence identity with the full-length nucleotide sequence of SEQ ID NO: 1 or a variant thereof, for example SEQ ID NO:11. In another embodiment, said polynucleotide has at least 80% sequence identity with the full-length nucleotide sequence of SEQ ID NO: 1 or a variant thereof, for example SEQ ID NO:11, wherein the polynucleotide contains at least one of:

(a) adenine as the nucleotide corresponding to position 817 of the full-length nucleotide sequence of SEQ ID NO: 1 or a variant thereof, for example SEQ ID NO:11;

(b) cytosine as the nucleotide corresponding to position 808 of the full-length nucleotide sequence of SEQ ID NO: 1 or a variant thereof, for example SEQ ID NO:11;

(c) cytosine as the nucleotide corresponding to position 33 of the full-length nucleotide sequence of SEQ ID NO: 1 or a variant thereof, for example SEQ ID NO:11;

(d) cytosine as the nucleotide corresponding to position 259 of the full-length nucleotide sequence of SEQ ID NO: 1 or a variant thereof, for example SEQ ID NO:11; and (e) guanine as the nucleotide corresponding to position 315 of the full-length nucleotide sequence of SEQ ID NO: 1 or a variant thereof, for example SEQ ID NO:11.

The inventors have surprisingly demonstrated that expressing HaKRKY76 increases yield under standard growth conditions and also increases stress tolerance under mild and severe conditions. Thus, in one embodiment, said phenotype is increased yield and said method is directed to increasing yield of a plant compared to a control plant.

The term "yield" includes one or more of the following non-limitative list of features: early flowering time, biomass (vegetative biomass (root and/or shoot biomass) or seed/grain biomass), seed/grain yield, seed/grain viability and germination efficiency, seed/grain size, starch content of grain, early vigour, greenness index, increased growth rate, delayed senescence of green tissue. The term "yield" in general means a measurable produce of economic value, typically related to a specified crop, to an area, and to a period of time. Individual plant parts directly contribute to yield based on their number, size and/or weight. The actual yield is the yield per square meter for a crop and year, which is determined by dividing total production (includes both harvested and appraised production) by planted square meters.

Thus, according to the invention, yield comprises one or more of and can be measured by assessing one or more of: increased seed yield per plant, increased seed filling rate, increased number of filled seeds, increased harvest index, increased viability/germination efficiency, increased number or size of seeds/capsules/pods/grain, increased growth or increased branching, for example inflorescences with more branches, increased biomass or grain fill. Preferably, increased yield comprises an increased number of grain/seed/capsules/pods, increased biomass, increased growth, increased number of floral organs and/or floral increased branching. Yield is increased relative to a control plant. For example, the yield is increased by 2%, 3%, 4%, 5%-10%, 10%-50% or more compared to a control plant, for example by at least 10%, 15%, 20%, 25%, 30%, 35%, 40%, 45% or 50%.

In another embodiment, said phenotype is stress tolerance and said method relates to increasing stress tolerance of a plant. The term "stress" or "stress condition" as used herein includes abiotic and biotic stress. Said stress/stress tolerance is preferably selected from one or any combination of the following: freezing, low temperature, chilling, drought, high salinity, waterlogging. In one preferred embodiment, the stress is drought.

Species such as winter cereals are adapted to cold or moderate-cold weather and can tolerate temperatures ranging from 0° C. to 15° C., as well as freezing temperatures, rather well if they have previously been acclimated to reduced temperatures. By contrast, tropical and subtropical species, including important crops, such as maize, rice or tomato, are sensitive to low temperatures and appear to lack efficient acclimation mechanisms.

Furthermore, in *Arabidopsis* research, stress is often assessed under severe conditions that are lethal to wild type plants. For example, drought tolerance is assessed predominantly under quite severe conditions in which plant survival is scored after a prolonged period of soil drying. However, in temperate climates, limited water availability rarely causes plant death, but restricts biomass and seed yield. Moderate water stress, that is suboptimal availability of water for growth can occur during intermittent intervals of days or weeks between irrigation events and may limit leaf growth, light interception, photosynthesis and hence yield potential. Leaf growth inhibition by water stress is particularly undesirable during early establishment.

In Skirycz et al., 2011, different transgenic *Arabidopsis* events with enhanced tolerance to lethal drought were analyzed in a mild stress assay. The authors screened the literature in order to identify *Arabidopsis* genes that in gain- or loss-of-function situations confer drought stress tolerance without penalties in growth, and then selected 25 to perform the assay. In this assay, two lines showed larger plants while the rest were smaller, either in control or under drought conditions. However, growth reduction under mild stress was similar for all of the genotypes tested. The authors therefore concluded that enhanced survival under severe drought is not a good indicator for improved growth performance under mild/moderate stress conditions which can often be found in temperate climates. Superior survival under severe drought is often associated with constitutive activation of water-saving mechanisms, such as stomatal closure, that can lead to growth penalty. Therefore, genes that are useful in conferring tolerance to severe stress conditions in transgenic plants and increase survival rates are in most cases detrimental to plant yield when the transgenic plant expressing such transgene(s) is exposed to mild stress conditions.

The terms moderate or mild stress/stress conditions are used interchangeably and refer to non-severe stress non-lethal stress. Moderate stress, unlike severe stress, does not lead to plant death. Under moderate, that is non-lethal, stress conditions, wild type plants are able to survive, but show a decrease in growth and seed production and prolonged moderate stress can also result in developmental arrest. The decrease can be at least 5%-50% or more. The effects of severe stress are usually measured as % tage of surviving plants, whereas the effects of moderate stress can be measured by assessing yield, growth or other parameters other than plant survival. Tolerance to severe stress is measured as a percentage of survival, whereas moderate stress does not affect survival, but growth rates.

Accordingly, the term moderate stress as used herein results in a measurable decrease of growth rates in wild type plants. Assays that mimic moderate stress conditions for *Arabidopsis thaliana* plants are described herein and in Skirycz et al, 2011. The decrease may be at least 5%-50% or more, for example 5%-10%, 1-25%, 20-30%, 30-40%, 40-50%.

The precise conditions that define moderate stress vary from plant to plant and also between climate zones, but ultimately, these moderate conditions do not cause the plant to die. With regard to high salinity for example, most plants can tolerate and survive about 4 to 8 dS/m. Specifically, in rice, soil salinity beyond ECe~4 dS/m is considered moderate salinity while more than 8 dS/m becomes high. Similarly, pH 8.8-9.2 is considered as non-stress while 9.3-9.7 as moderate stress and equal or greater than 9.8 as higher stress.

Drought stress can be measured through leaf water potentials. Generally speaking, moderate drought stress is defined by a water potential of between −1 and −2 Mpa. This has for example been applied in experiments relating to barley and *Phaseolus vulgaris* L. (Wingler et al, 1999 and Torres-Franklin et al 2007).

Waterlogging/irrigation: stress. Waterlogging is flooding of the root system whereas submergence is related to immersion of the whole plant (Bailey-Serres et al, Trends in Plant Sciences, 2012, Vo. 17, No. 3, 129-138).

Moderate temperatures vary from plant to plant and specially between species. Normal temperature growth conditions for *Arabidopsis* are defined at 22-24° C. For example, at 28° C., *Arabidopsis* plants grow and survive, but show severe penalties because of "high" temperature stress associated with prolonged exposure to this temperature. However, the same temperature of 28° C. is optimal for sunflower, a species for which 22° C. or 38° C. causes mild, but not lethal stress. In other words, for each species and genotype, an optimal temperature range can be defined as well as a temperature range that induces mild stress or severe stress which leads to lethality.

Also, depending on the soil conditions and/or geographic region in which the plant is grown, "mild stress conditions" can be constant/permanent. For example, the yield of the same soybean (or maize) genotype exhibits differences every year when comparing different regions presenting varied rainfall regimes, even when no drought season occurred during this time.

Moderate stress conditions are common even in temperate climates and affect yield. A skilled person would be able to determine temperatures that can lead to mild stress for any given species based on common general knowledge in the technical field and/or routine methods.

Specifically, according of the aspects of the invention, HaWRKY76 can be expressed in another plant that is not sunflower to elicit the beneficial effects described herein.

In other aspects, the invention relates to plants or parts thereof obtained or obtainable by the methods described herein as well as products derived therefrom.

In yet another aspect, the invention relates to the use of a nucleic acid described above in increasing tolerance to abiotic or biotic stress. In one embodiment, said nucleic acid comprises or consists of SEQ ID NO:1 or a variant thereof, for example SEQ ID NO:11 or SEQ ID NO:9, a functional variant or part thereof as defined above. In one embodiment, said polynucleotide has at least 80% sequence identity with the full-length nucleotide sequence of SEQ ID NO: 1 or SEQ ID NO:9. In another embodiment, said polynucleotide has at least 80% sequence identity with the full-length nucleotide sequence of SEQ ID NO: 1 or a variant thereof, for example SEQ ID NO:11, wherein the polynucleotide contains at least one of:
 (a) adenine as the nucleotide corresponding to position 817 of the full-length nucleotide sequence of SEQ ID NO: 1 or a variant thereof, for example SEQ ID NO:11;
 (b) cytosine as the nucleotide corresponding to position 808 of the full-length nucleotide sequence of SEQ ID NO: 1 or a variant thereof, for example SEQ ID NO:11;
 (c) cytosine as the nucleotide corresponding to position 33 of the full-length nucleotide sequence of SEQ ID NO: 1 or a variant thereof, for example SEQ ID NO:11;
 (d) cytosine as the nucleotide corresponding to position 259 of the full-length nucleotide sequence of SEQ ID NO: 1 or a variant thereof, for example SEQ ID NO:11; and
 (e) guanine as the nucleotide corresponding to position 315 of the full-length nucleotide sequence of SEQ ID NO: 1 or a variant thereof, for example SEQ ID NO:11.

In one embodiment, said stress is abiotic stress and for example selected from drought or irrigation. In one embodiment, said stress is moderate stress. In another embodiment, said stress is severe stress.

In another aspect, the invention relates to an isolated HaWRKY76 promoter nucleic acid sequence. This can be selected from SEQ ID NO: 10 or a sequence with at least 80%, 85%, 90%, or 95% sequence identity with SEQ ID NO: 10. In one embodiment, the sequence does not comprise the 5' UTR. In another aspect, the invention relates to a vector comprising SEQ ID NO: 10 or a sequence with at least 80%, 85%, 90%, or 95% sequence identity with SEQ ID NO: 10. Also within the scope of the invention is plant expressing a construct comprising a nucleic acid molecule comprising SEQ ID NO: 10 or a sequence with at least 80%, 85%, 90%, or 95% sequence identity with SEQ ID NO: 10 operably linked to another nucleic acid sequence, a method for making such plants and uses thereof in controlling stress responses.

Specific embodiments are further described by the following Examples.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described. The application claims benefit from U.S. 61/986,730. HaWRKY76 is termed HaWKKY2 therein. Accordingly, the terms HaWRKY76 and HaWKKY2 are synonymous and are used interchangeably.

EXAMPLES

In reference to the following Examples, it will be recognized by persons skilled in the art that a transcription factor that is associated with a particular first trait may also be associated with at least one other, unrelated and inherent second trait which is not predicted by the first trait.

Genetic Construct

35SCaMV:HaWRKY76 was employed in the various Examples described below. The HaWRKY76 coding sequence was obtained from *Helianthus annuus* CF31 genotype. It was amplified by RT-PCR with specific oligonucleotides using as a template the total RNA of the leaves. The amplification product was cloned directly in the pBI121 vector. In this way, the cDNA expression was controlled by the 35S CaMV promoter. The construct 35S:HaWRKY76 was initially introduced in the BL21 (DE3) *E. coli* strain and then transferred to *Agrobacterium tumefaciens* strain LBA4404 by electroporation using the GENE PULSER™ (Bio-Rad). The protein sequence as shown in SEQ ID NO:12 was expressed in plants.

Plant Material and Growth Conditions

*Arabidopsis thaliana* ecotype Columbia (Col-0) was purchased from Lehle Seeds (Tucson, Ariz.). Plants were grown directly on soil in a growth chamber at 22-24° C. under long-day photoperiods (16 hours of illumination with a mixture of cool-white and GroLux fluorescent lamps) at an intensity of approximately 180 µE $m^{-2}s^{-1}$ in pots (8 cm diameter×7 cm height).

Seeds of *Helianthus annuus* L. (sunflower CF31, from Advanta Seeds) were grown in the soil pots in a culture chamber at 28° C. for variable periods of time depending on the purpose of the experiment, as further detailed in the figure legends.

Drought Assays

Depending on the particular Experiment, as detailed in the figure legends, sunflower seedlings were placed on a filter paper during 30 minutes, and R2 plants grown in soil pots were stressed by stopping watering (dehydration) during 15 days. Every one, two, or three days after this treatment, 1 cm diameter leaf disks were frozen in liquid nitrogen for further RNA analysis.

As a control of viability of the plants, plants were re-watered after the taking of the sample. Only the samples of the survivors were analyzed.

25-day-old *Arabidopsis* plants were subjected to drought stress by stopping of watering (dehydration) during 16-18 days. After this treatment, the plants were re-watered to saturation. Survivor plants were counted two days after recovery at normal growth conditions.

In the case of drought assays maintaining the same water volume, soil pots were weighed every 2-3 days, and water was added to those pots that needed watering in order to maintain the same weight in each soil pot. The weight differences were recorded so as to calculate the total water volume added to each pot.

Transformation of *Arabidopsis thaliana*

Transformed *Agrobacterium tumefaciens* strain LBA4404 was used to obtain transgenic *Arabidopsis* plants. The method employed for transforming *Arabidopsis thaliana* was the one using immersion (the floral dip procedure), as describe by Clough and Bent, *Plant J.* 16:735-743 (1998). Transformed plants were selected on the basis of kanamycin resistance and positive PCR, which was carried out on genomic DNA with specific oligonucleotides. Five positive independent lines were used to select homozygous T3 and T4 in order to analyze phenotypes and the expression levels of HaWRKY76. To assess HaWRKY76 expression, real time RT-PCR was performed on homozygous transformants, as described further below. Plants transformed with pBI101.3 were used as negative controls.

RNA Isolation and Expression Analyses by Real Time RT-PCR

RNA for real time RT-PCR was prepared with TRIZOL® reagent (Invitrogen™) according to the manufacturer's instructions. RNA (2 µg) was used for the RT-PCR reactions using M-MLV reverse transcriptase (Promega). Quantitative PCRs were carried out using a MJ-Chromo4 apparatus in a 20 µl final volume containing 1 µl SyBr green (10×), 9 pmol of each primer, 2 mM $MgCl_2$, 10 µl of a 1/30 dilution of the RT-PCR reaction, and 0.05 µk Platinum Taq (Invitrogen Inc.). Fluorescence was measured at 78-80° C. during 40 cycles. Sunflower total RNA was also prepared with the TRIZOL® (Invitrogen Inc.) technique.

Chlorophyll Quantification

Extracts from 100 weighed mg of leaves were prepared after freezing with liquid nitrogen. 1.5 ml of 80% acetone was added to each sample, and the tubes were placed in darkness for a period of 30 minutes. During this incubation, the sample solids were decanted and the absorbance at 645 and 663 nm, respectively, was measured in the supernatants with a spectrophotometer. Chlorophyll concentrations were quantified according to the methods disclosed in Whatley et al. (1963).

Injury Evaluation by the Ion Leakage Technique

The ion leakage technique was carried out essentially as described by Sukumaran and Weiser (1972) with minor modifications. The conductivity percentage was calculated as the ratio between C2/C1, i.e., [L=(C1/C2)*100], and was used as the index of injury. C1 represents the conductance after the treatment, and C2 represents the maximum conductance of each sample. L values higher than 50% indicate a severe injury.

Water Loss Evaluation

Fully expanded leaves were detached from Wild-Type (WT) and the 35S:HaWRKY76 transgenic plants, respectively, and placed on Petri dishes under strictly controlled conditions. Water loss was determined by weighing the leaves at the times indicated in the Figures as compared with the initial weight. The values are reported as a percentage of the initial weight.

Example 1

Seeds of *Helianthus annuus* L. (sunflower CF31, from Advanta Seeds) were grown in the soil pots in a culture chamber at 28° C. for a period of 5 days. The HaWRKY76 transcription levels were quantified by RT-PCR and normalized with housekeeping ACTIN transcripts. The obtained values were normalized with respect to the value measured in the root sample, which was arbitrarily assigned a value of 1. An Anova test was performed, followed by a Fisher LSD post-hoc test. The results are shown in FIG. 5. The different letters (a and b) indicate samples that were found to be significantly different (i.e., p value<0.05). As demonstrated by the results summarized in FIG. 5, HaWRKY76 expression patterns in 5-day-old sunflower seedlings indicated higher levels in roots and hypocotyls than in cotyledons.

Example 2

Seeds of *Helianthus annuus* L. (sunflower CF31, from Advanta Seeds) were grown in the soil pots for 5 days under control conditions and then placed for 30 minutes on a filter paper (Drought) or in MS 0.5× solution (Control). The HaWRKY76 transcription levels were quantified by RT-PCR and normalized with housekeeping ACTIN transcripts. The obtained values were normalized with respect to the value measured in the control root sample, which was arbitrarily assigned a value of 1. An Anova test was performed, followed by a Fisher LSD post-hoc test. The results are shown in FIG. 6A. The different letters (a, b, and c) indicate samples that were found to be significantly different (i.e., p value<0.05).

Figure 6:
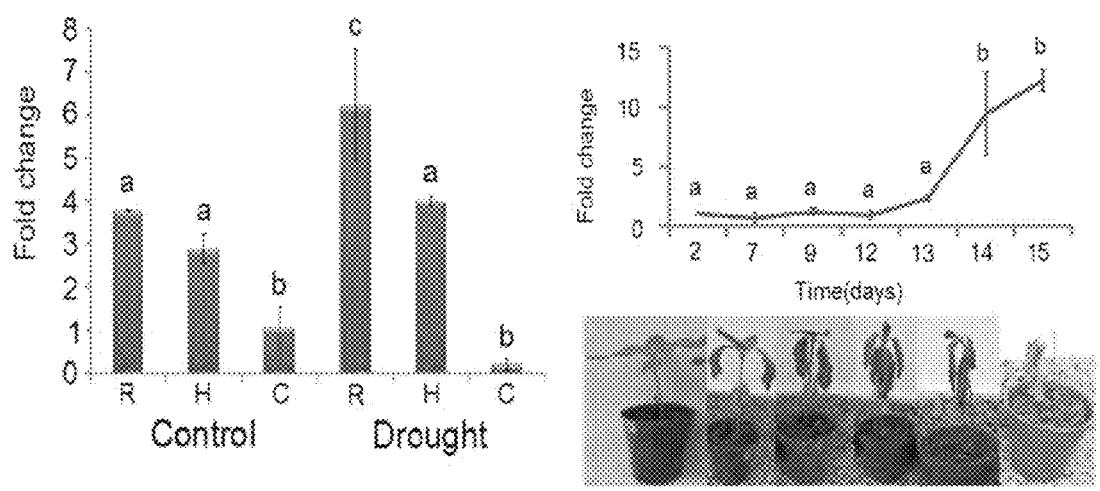
FIG. 6A shows the Ha WRKY76 expression levels in 5-day-old sunflower seedlings, in standard conditions (left) and under severe drought stress (right)
FIG. 6B shows the expression levels of sunflower R2 plants subjected to a continuous and severe drought stress during fifteen days. Different letters indicate samples that are significantly different (p value<0.05). An illustrative photograph of sunflower plants subjected to severe water stress and used to take the RNA samples is shown in the bottom of FIG. 6A.

Sunflower R2 plants were subjected to a continuous and severe drought stress (stopping watering during 15 days). The leaf disks were frozen at the period of time indicated in FIG. 6B. As a control of the plants viability, the plants were re-watered after sampling. The transcription levels of HaWRKY76 were quantified in these sunflower R2 plants subjected to a continuous and severe drought stress. The obtained values were normalized with respect to the value measured in the sample harvested at day 2 which was arbitrarily assigned a value of 1. An Anova test was performed, followed by a Fisher LSD post-hoc test. The results are shown in FIG. 6B. As demonstrated by the results summarized in FIG. 6, HaWRKY76 expression is up-regulated by water stress.

Example 3

Transgenic *Arabidopsis thaliana* plants bearing the construct 35S:HaWRKY76 were obtained by the floral dip method (see "Constructs" above), and three homozygous lines were selected for further analysis. Transcription levels of HaWRKY76 were quantified by real time RT-PCR. All of the values were normalized with respect to the value measured in line W76-C, which was arbitrarily assigned a value of 1 and considered as a low-level-expression line. WT plants were used as negative controls, and error bars correspond to the standard deviations from three biological replicas. An Anova test was performed, followed by a Fisher LSD post-hoc test. FIG. 7 shows the relative expression levels of HaWRKY76 in *Arabidopsis* transgenic plants bearing the construct 35S:HaWRKY76. Different letters (a, b, and c) indicate samples that were found to be significantly different (i.e., p value<0.05).

Example 4

Transgenic *Arabidopsis thaliana* plants bearing the construct 35S:HaWRKY76 were obtained by the floral dip method (see "Constructs" above), and three homozygous lines were selected for further analysis. The plants were grown in standard growth conditions. The root length was measured in the 35S:HaWRKY76 (W76-A, W76-B and W76-C) and the WT plants. An Anova test was performed, followed by a Fisher LSD post-hoc test. Error bars correspond to the standard deviations twenty biological replicas.

The average root lengths and standard deviations were calculated in 7- and 14-day-old seedlings. The averages of each genotype were calculated, and the results are shown in panel (A) of FIG. 8. Different letters (a, b, c, and d) indicate samples that were found to be significantly different (i.e., p value<0.05). Panel (B) of FIG. 8 is a photograph of the roots of the 7-day-old plants grown on Petri dishes. As demonstrated by the results shown in FIG. 8, *Arabidopsis* plants bearing the construct 35S:HaWRKY76 develop longer roots than the control plants in standard growth conditions.

Example 5

Transgenic *Arabidopsis thaliana* plants bearing the construct 35S:HaWRKY76 were obtained by the floral dip method (see "Constructs" above), and three homozygous lines were selected for further analysis. Roots were detached from 33-day-old 35S:HaWRKY76 (W76-A, W76-B and W76-C) and WT control plants grown on sand in standard conditions, and the average weights of the respective roots were measured. An Anova test was performed, followed by a Fisher LSD post-hoc test. Error bars correspond to the standard deviations from three biological replicas.

Figure 9:
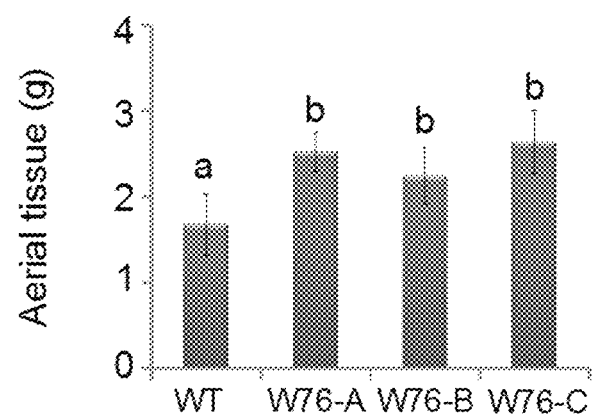
FIG. 9 shows the average aerial biomass (weight of detached rosettes and stems) of 35-day-old plants belonging to three homozygous transgenic lines of *Arabidopsis* transgenic plants bearing the construct 35S:HaWRKY76 and of 35-day-old WT control plants that were grown in standard conditions. Different letters indicate samples that are significantly different (p value<0.05).

The average root weight of each genotype is shown in FIG. 9. Different letters (a and b) indicate samples which were found to be significantly different (i.e., p value<0.05). As demonstrated by the results shown in FIG. 9, *Arabidopsis* plants bearing the construct 35S:HaWRKY76 grown on sand in standard growth conditions exhibit higher root biomass compared with WT control plants.

Example 6

Transgenic *Arabidopsis thaliana* plants bearing the construct 35S:HaWRKY76 were obtained by the floral dip method (see "Constructs" above), and three homozygous lines were selected for further analysis. The plants were grown on poor soil in standard growing conditions. Rosettes of 36-day-old 35S:HaWRKY76 (W76-A, W76-B and W76-C) and WT plants were detached, and the weight of the rosettes was measured. An Anova test was performed, followed by a Fisher LSD post-hoc test. Error bars correspond to the standard deviations from four or five biological replicas. The rosette weight (mg) of each genotype is shown in panel (A) of FIG. 10.

The weighed leaves of the 36-day-old plants were frozen, and chlorophyll was extracted with acetone and quantified by absorbance at 645 and 663 nm, respectively (see "Chlorophyll Quantification" conditions above). The total chlorophyll content per plant is shown in panel (B) of FIG. 10. The protein content was also determined using BSA as standard according to the method described in Bradford (1976). The protein concentration per plant is shown in panel (C) of FIG. 10.

Figure 10:
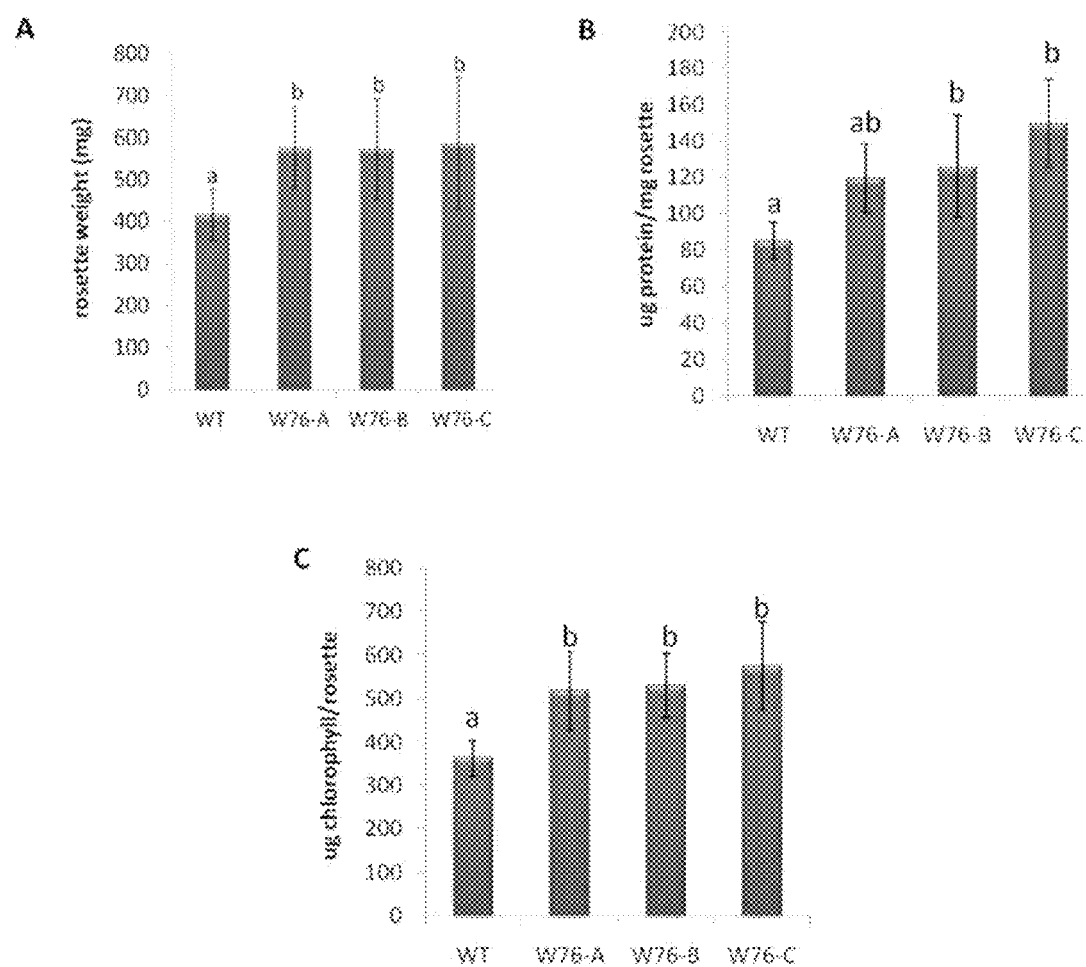
FIG. 10A shows the weight of rosettes detached from plants belonging to three homozygous transgenic lines of *Arabidopsis* transgenic plants bearing the construct 35S: HaWRKY76 and of the WT control plants grown on poor soil in standard conditions.
FIG. 10B shows the chlorophyll content per mg of rosette leaves of each of the respective plants.
FIG. 10C shows the total protein concentration of each of the respective plants. Different letters indicate samples that are significantly different (p value<0.05).

As demonstrated by the results shown in FIG. 10, *Arabidopsis* plants bearing the construct 35S:HaWRKY76 grown on poor soil in standard conditions exhibit higher rosette biomass compared with the WT control plants. Different letters (a and b) indicate samples which were found to be significantly different (i.e., p value<0.05). As also shown in FIG. 10B and FIG. 10C, the chlorophyll content (μg) per mg leaves is similar when comparing genotypes. However, because rosettes of the transgenic plants are larger, the total protein and chlorophyll contents differ when comparing genotypes, i.e., the contents are larger in the transgenic plants than in the WT control plants.

Figure 11:
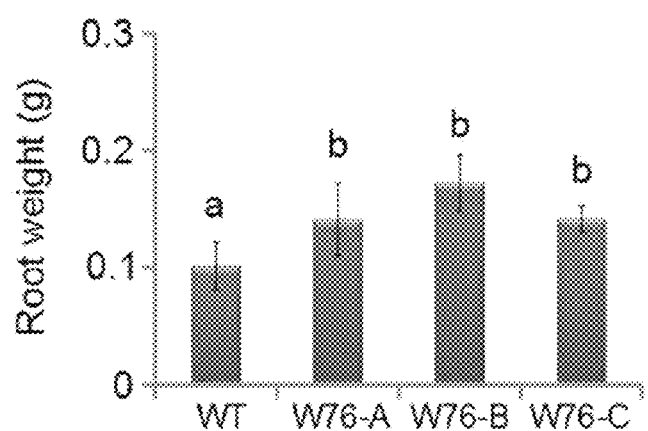
FIG. 11 shows the root biomass of 35-day-old plants belonging to three homozygous transgenic lines of *Arabidopsis* transgenic plants bearing the construct 35S:HaWRKY76 and the WT control plants, all grown on sand irrigated with Hoagland 0.5 x. Different letters indicate samples that are significantly different (p value<0.05).

As further shown in FIG. 11, 35-day-old *Arabidopsis* plants bearing the construct 35S:HaWRKY76 grown in standard conditions exhibit higher aerial biomass compared with the WT control plants. Error bars correspond to the standard deviations from four biological replicas.

Example 7

Transgenic *Arabidopsis thaliana* plants bearing the construct 35S:HaWRKY76 were obtained by the floral dip method (see "Constructs" above), and three homozygous lines were selected for further analysis. The plants were grown on poor soil in standard growing conditions. The seeds of each plant from each of the 35S:HaWRKY76 (W76-A, W76-B and W76-C) and WT genotype were separately harvested and weighed. The average yield of 4 plants of each genotype is shown in FIG. 12A. An Anova test was performed, followed by a Fisher LSD post-hoc test. Different letters (a and b) indicate samples which were found to be significantly different (i.e., p value<0.05).

Figure 12:
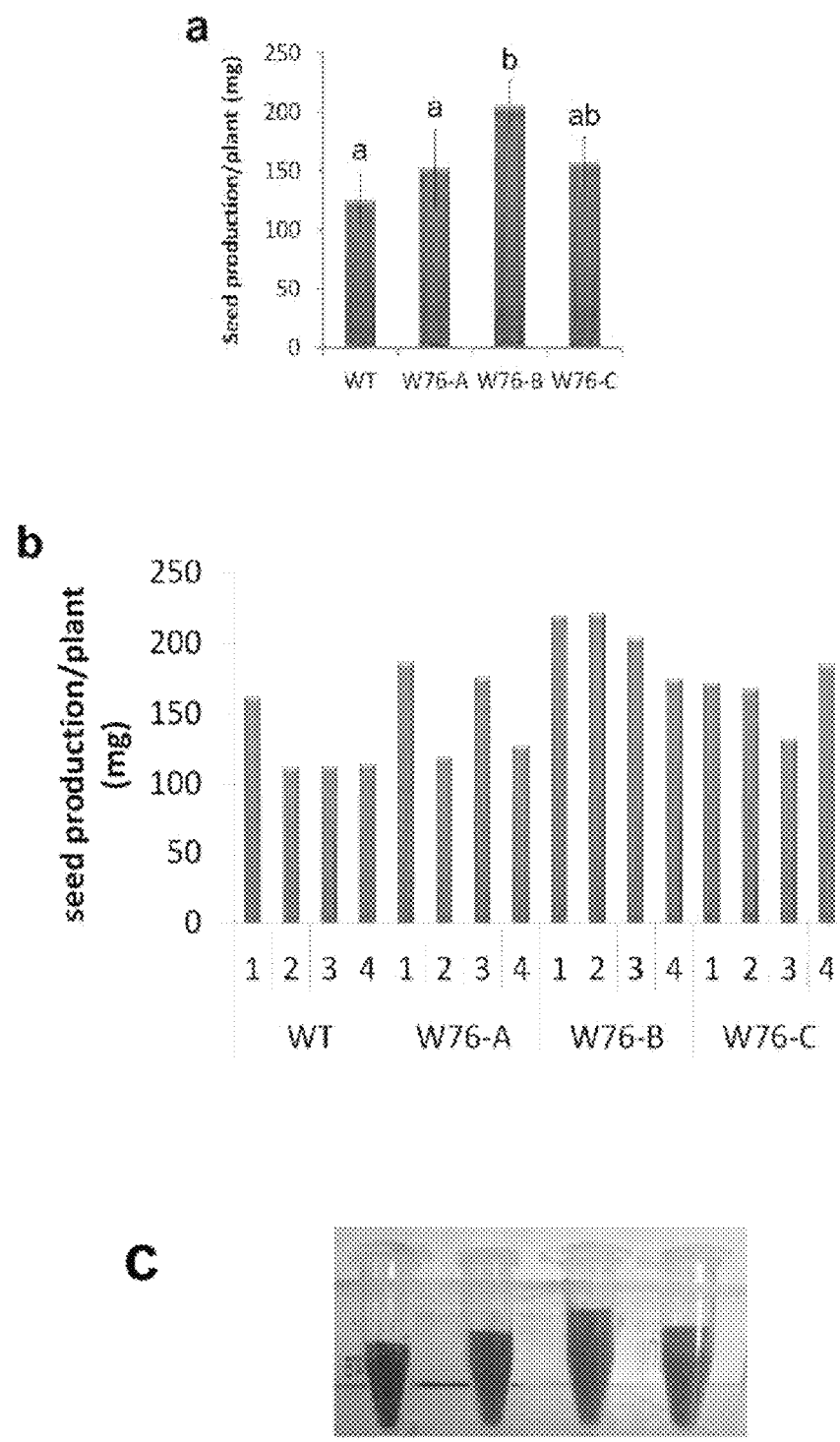
FIG. 12A shows the average seeds yield of 4 plants of each genotype grown on poor soil conditions (nutritional deficiency)
FIG. 12B shows the yield per individual plant.
FIG. 12C is a photograph of the harvested seeds (35S:HaWRKY76 transgenic seeds and WT control seeds). Different letters indicate samples that are significantly different (p value<0.05).

FIG. 12B shows the yield per plant, with the horizontal line representing the average value of the WT plants. FIG. 12C is a photograph of the harvested seeds of 4 plants of each genotype. As demonstrated by the results shown in FIG. 12, *Arabidopsis* plants bearing the construct 35S:HaWRKY76 grown in poor soil conditions exhibit higher yields than the WT control plants.

Figure 13:
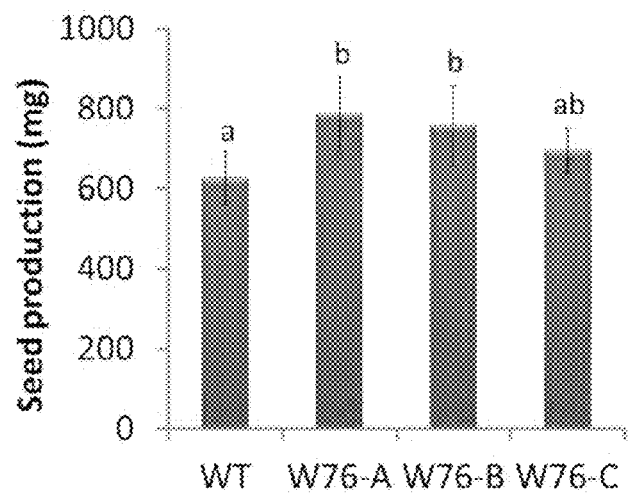
FIG. 13 shows the yields of plants belonging to three homozygous transgenic lines of *Arabidopsis* transgenic plants bearing the construct 35S:Ha WRKY76 and of the WT control plants grown in standard conditions. Different letters indicate samples that are significantly different (p value<0.05).

As additionally shown in FIG. 13, *Arabidopsis* plants bearing the construct 35S:HaWRKY76 grown on standard conditions also exhibit higher yields than the WT control plants. Specifically, FIG. 13 shows the average yield of 4 plants of each genotype. An Anova test was performed, followed by a Fisher LSD post-hoc test. Different letters (a and b) indicate samples which were found to be significantly different (i.e., p value<0.05).

Example 8

Figure 14:
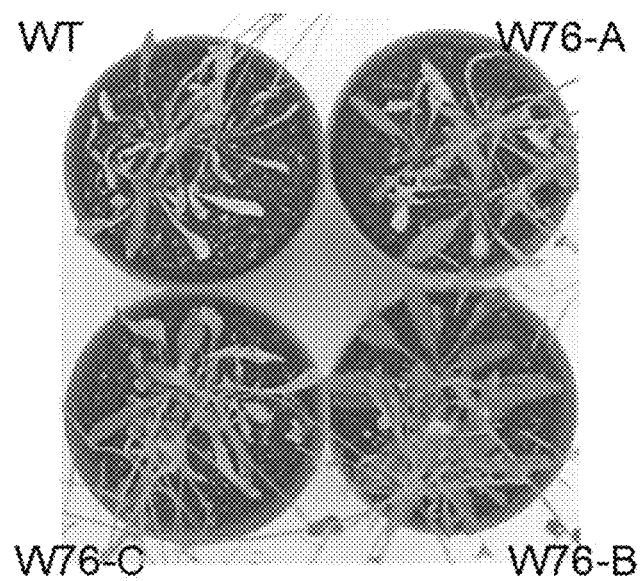
FIG. 14 is a photograph of plants belonging to three homozygous lines of *Arabidopsis* transgenic plants bearing the construct 35S:HaWRKY76 and of WT control plants that have been subjected to severe drought stress. The photograph is taken 4 days after the plants were re-watered following the severe drought stress treatment.

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were well irrigated for 25 days. Then, the 25-day-old well-irrigated plants were subjected to drought stress by stopping watering until severe damage was visible. At that time, the plants were re-watered. FIG. 14 is a photograph of the plants taken 4 days after the re-watering.

As can be seen in the photograph of FIG. 14, *Arabidopsis* plants bearing the construct 35S:HaWRKY76 are more tolerant to drought than their WT control plants.

Example 9

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were grown on poor soil (undefined stress), and were subjected to drought during the vegetative stage and also during the reproductive stage. The plants were subjected to drought stress by stopping watering until severe damage was visible. At that time, the plants were re-watered.

FIG. 15A is a photograph of the plants subjected to drought during the vegetative stage, and FIG. 15C is a photograph of the plants subjected to drought during the reproductive stage.

The yield (seed production) of the plants was measured. Error bars correspond to the standard deviations from four biological replicas. An Anova test was performed, followed by a Fisher LSC post-hoc test. FIG. 15B shows the yield of the plants when subjected to drought during the vegetative stage, and FIG. 15D shows the yield of the plants when subjected to drought during the reproductive stage. Different letters (a and b) indicate samples that were found to be significantly different (i.e., p value<0.05).

Figure 15:
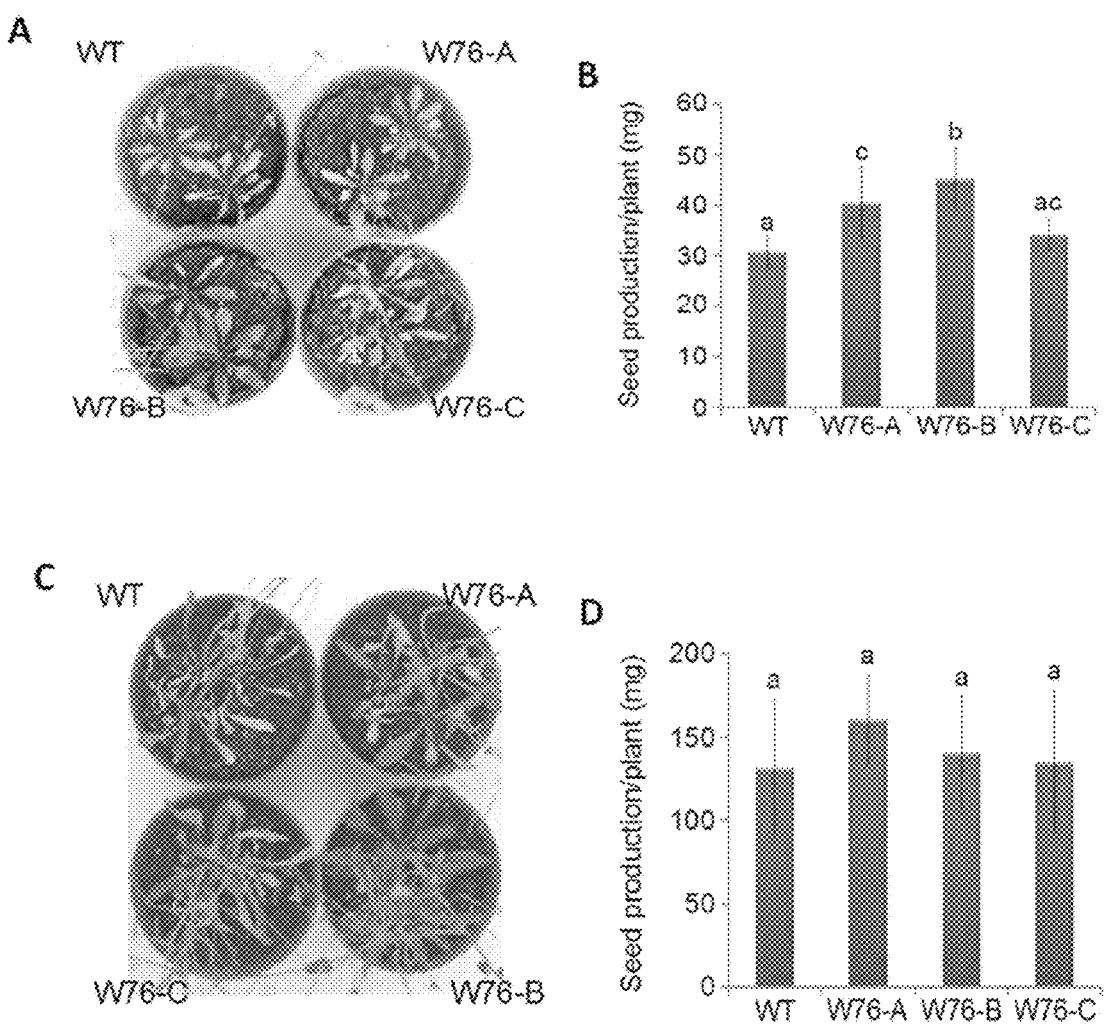
FIG. 15A is a photograph of the plants belonging to three homozygous transgenic lines of *Arabidopsis* transgenic plants bearing the construct 35S:HaWRKY76 and of WT control plants that were subjected to drought during the vegetative stage.
FIG. 15C is a photograph of the respective plants subjected to drought during the reproductive stage.
FIG. 15B shows yields of the respective plants subjected to drought during the vegetative stage.
FIG. 15D shows yields of the respective plants subjected to drought during the reproductive stage. In both treatments, a nutritional stress (generated by growing the plants on poor soil) was applied. Different letters indicate samples that are significantly different (p value<0.05).

As demonstrated by the results shown in FIG. 15, *Arabidopsis* plants bearing the construct 35S:HaWRKY76 grown in poor soil conditions are more tolerant to drought than their WT control plants and show enhanced yield when the stress is applied during the vegetative stage. When the stress was suffered during the reproductive stage, no significant differences between the genotypes were observed.

Figure 16:
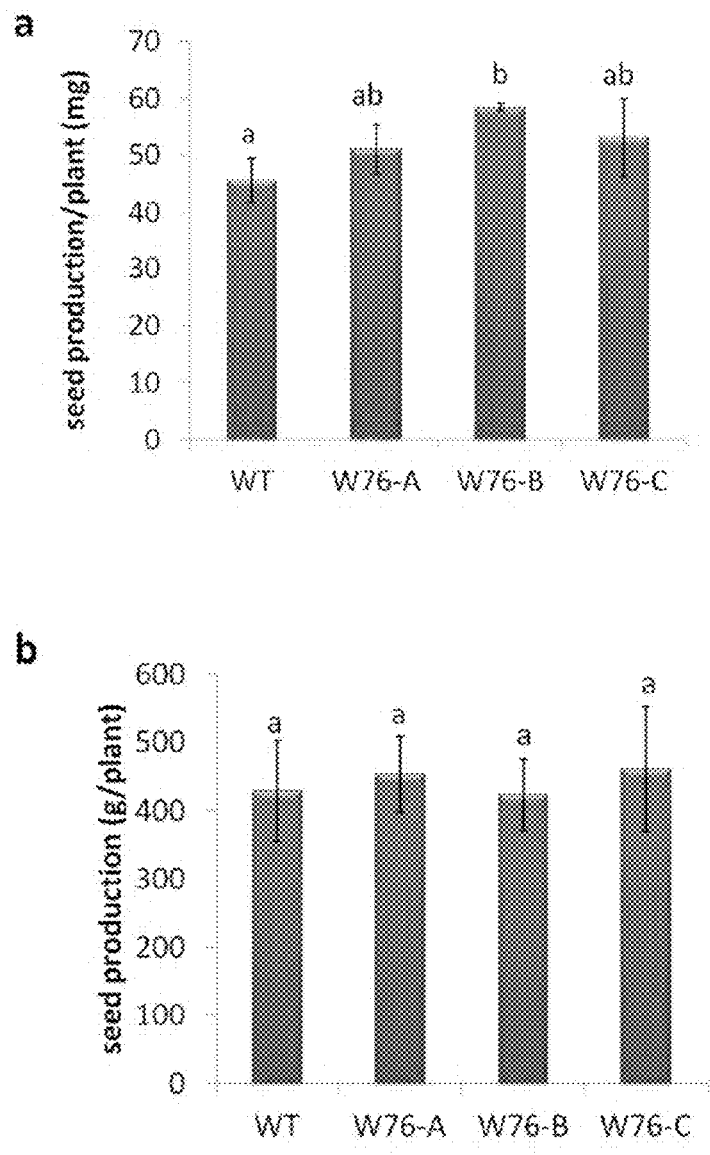
FIG. 16A shows the enhanced yield of *Arabidopsis* transgenic plants bearing the construct 35S:HaWRKY76 when drought stress was applied during the vegetative stage.
FIG. 16B shows that no significant differences in yield between the genotypes were observed when the drought stress was suffered during the reproductive stage. In these experiments, the only stress applied was drought and other conditions (soil) were standard. Different letters indicate samples that are significantly different (p value<0.05).

The top panel of FIG. 16 shows the enhanced yield of the transgenic plants when the drought stress was suffered during the vegetative stage, while the lower panel shows that no significant differences in yield between the genotypes were observed when the drought stress was suffered during the reproductive stage. In FIG. 16, error bars correspond to the standard deviations from four biological replicas.

Figure 35:
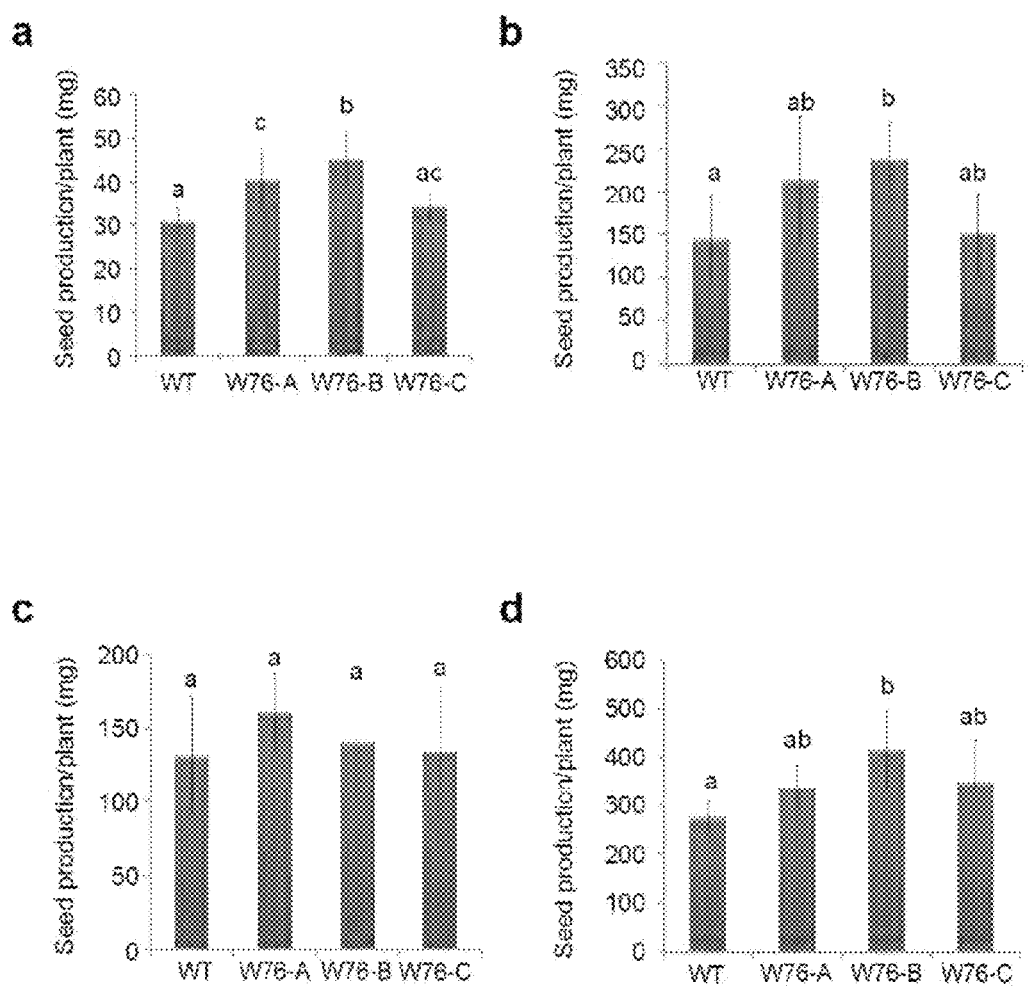
FIG. 35. HaWRKY76 transgenic plants exhibit equal or higher yield than WT after water deficit or water excess treatments. (a, b) Seeds production of transgenic (W76-A, W76-B, W76-C) and WT plants subjected to mild water deficit in the vegetative (a) or the reproductive (b) stage. c, d) Seeds production of transgenic (W76-A, W76-B, W76-C) and WT plants in the reproductive stage subjected to submergence (c) or waterlogging (d). Two or three plants per pot were assayed. Three experiments were done and error bars correspond to standard deviations from four biological replicas in each experiment. ANOVA test was performed, followed by a Fisher LSD post-hoc test. Asterisks indicate samples which are significantly different from WT (P<0.05)

Similar experiments were conducted in a second set of experiments and the results are shown in FIG. 35.

Example 10

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W6-B and W76-C) and WT plants were grown on soil and normal watering stopped when the plants were 25-days old (mild drought stress). Soil pots (poor soil) were weighed every two days during the assay and water was added to those that needed it to maintain the same weight in all pots. After harvesting, plant yield was evaluated for each individual plant of each genotype.

FIG. 17A shows the average amount (ml) of water added to the soil for each genotype, and FIG. 17B shows the average yield per plant of each genotype. An Anova test was performed, followed by a Fisher LSC post-hoc test. Error bars correspond to the standard deviations from 10 biological replicas. Different letters (a and b) indicate samples that were found to be significantly different (i.e., p value<0.05).

Figure 17:
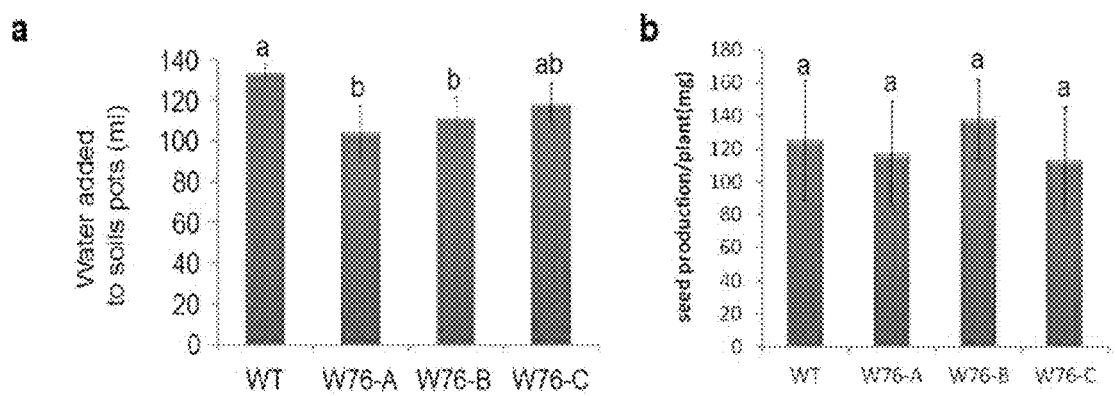
FIG. 17A shows the average water added.
FIG. 17B shows the average yield per plant for each of the three homozygous transgenic lines of *Arabidopsis* transgenic plants bearing the construct 35S:HaWRKY76 and the WT control plants. All of the plants were grown on soil and normal watering was stopped when the plants were 25 days old. Thereafter, the minimum quantity of water was added every two days to maintain the same weight in all pots. Different letters indicate samples that are significantly different (p value<0.05).

As demonstrated by the results shown in FIG. 17, *Arabidopsis* plants bearing the construct 35S:HaWRKY76 need less water than the WT control plants during a mild drought stress exhibiting similar yields.

Example 11

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were well irrigated (FIG. 18A) or subjected to moderate drought stress (FIG. 18B). In both cases, fully expanded leaves were detached from the 35S:HaWRKY76 and the WT plants that were (A) well irrigated and (B) subjected to moderate drought stress. The detached leaves were placed on Petri dishes under controlled conditions and weighed at the times indicated in FIGS. 18A and 18B, respectively. The values are reported as weight at each measured time with respect to the initial weight.

FIG. 18A shows the weight of leaves (% of initial weight) of the well-irrigated plants, FIG. 18B shows the weight of leaves (% of initial weight) of the plants subjected to moderate drought stress, and FIG. 18C is a photograph taken after 8 hours of treatment. An Anova test was performed, followed by a Fisher LSC post-hoc test. Error bars correspond to the standard deviations from 3 or 4 biological replicas. Different letters (a and b) indicate samples that were found to be significantly different (i.e., p value<0.05).

Figure 18:
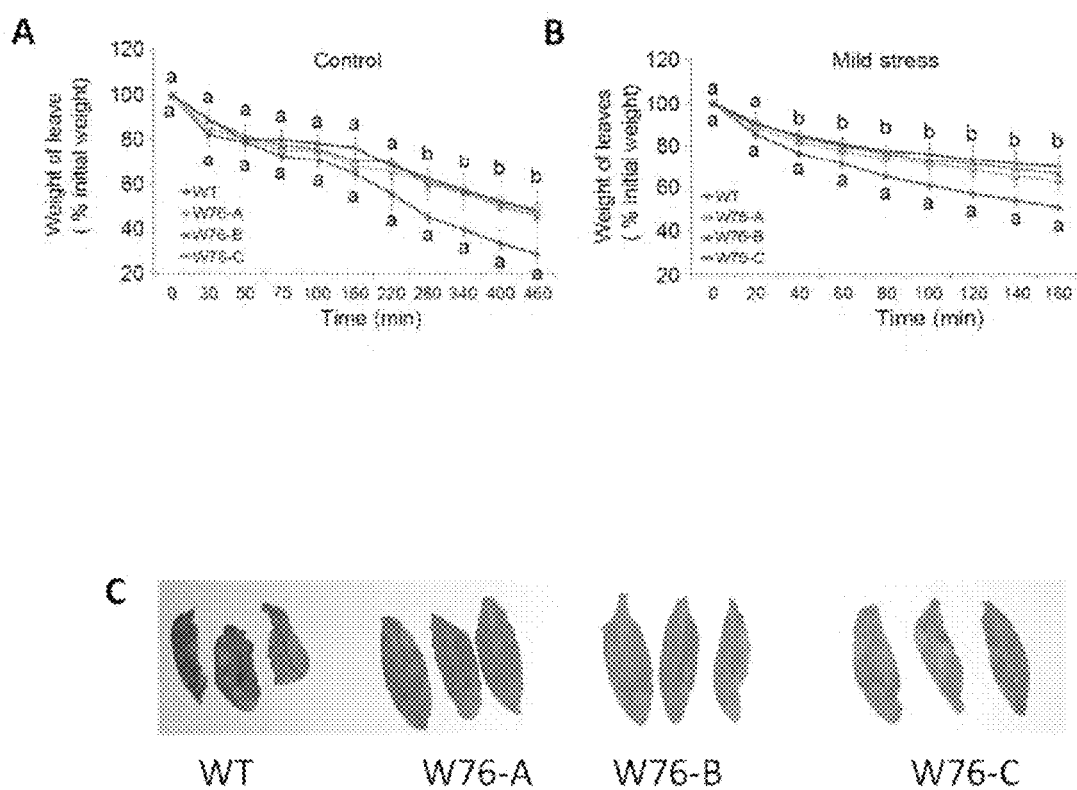
FIGS. 18A and 18B show the weight loss of leaves detached from plants belonging to three homozygous transgenic lines of *Arabidopsis* transgenic plants bearing the construct 35S:HaWRKY76 and WT control plants that were well-irrigated (FIG. 18A) and subjected to moderate drought stress (FIG. 18B).
FIG. 18C is an illustrative photograph of leaves of the respective plants taken after 8 hours of treatment. Different letters indicate samples that are significantly different (p value<0.05).

As demonstrated by the results shown in FIG. 18, *Arabidopsis* plants bearing the construct 35S:HaWRKY76 lost less water than their WT control plants.

Example 12

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were grown on poor soil for 25 days. The 25-day-old plants were then completely submerged during 5-6 days and placed in standard growing conditions until recovery. The number of survivors after treatment and the average seed yield of the survivors were calculated. One 6-day submergence experiment was performed with 12 plants of each genotype. As the number of survivors was not equal for all genotypes, the seed yield of survivors was calculated from one 5-day submerge experiment performed with 8 plants of each genotype.

FIG. 19A shows the percentage of survivors of each genotype after the treatment. FIG. 19B is a photograph of the plants taken after one week of recovery. FIG. 19C shows the average seed yield of survivors. An Anova test was performed, followed by a Fisher LSC post-hoc test. Error bars correspond to the standard deviations from 4-9 biological replicas. Different letters (a and b) indicate samples which were found to be significantly different (i.e., p value<0.05). FIG. 19D is an image of seeds produced by each genotype with respect to the average seed yields shown in FIG. 19C.

Figure 19:
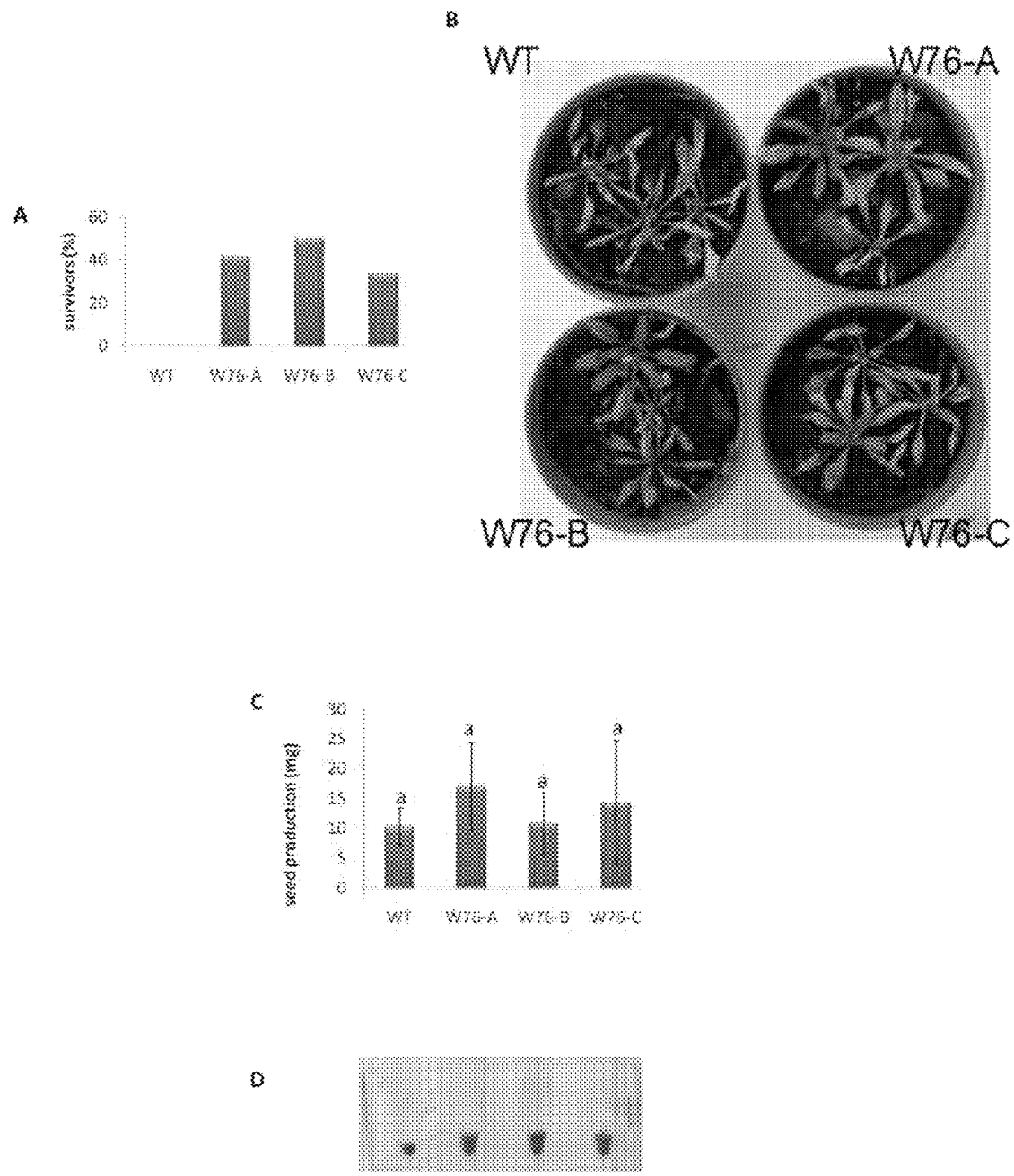
FIG. 19A shows the percentage of survivors after 25 day-old plants of three homozygous transgenic lines of *Arabidopsis* transgenic plants bearing the construct 35S:Ha WRKY76 and WT control plants were completely submerged during 6 days and then placed in standard growth conditions for recovery.
FIG. 19B is an illustrative photograph of the plants taken one week after recovery.
FIG. 19C shows the average seed yields of the recovered plants.
FIG. 19D shows the harvested seeds of each genotype. The number of survivors was lower for the WT genotype plants. Therefore, the total yield is significantly different (measured as the average) because only the survivors contribute. Different letters indicate samples that are significantly different (p value<0.05).

As demonstrated by the results shown in FIG. 19, *Arabidopsis* plants bearing the construct 35S:HaWRKY76 are more tolerant to submergence and exhibited higher yields after such submergence than their WT control plants.

Figure 20:
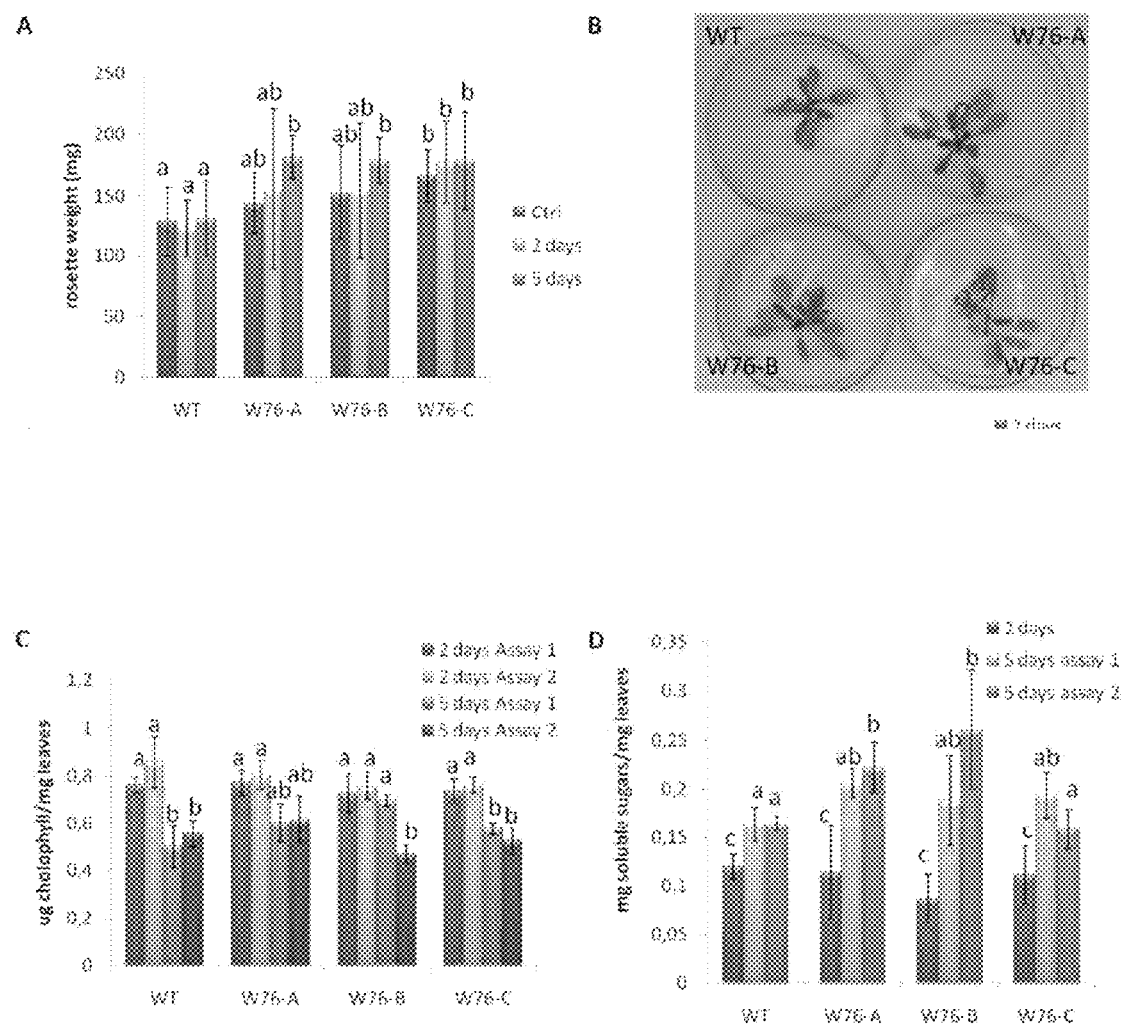
FIG. 20A shows the rosette weight of the respective plants measured 2 and 5 days after starting the treatment conditions referenced in FIG. 19.
FIG. 20B is an illustrative photograph of the rosettes of the plants taken 5 days after starting the treatment.
FIG. 20C shows the chlorophyll content/mg of rosette leaves of the respective plants measured 2 and 5 days after starting the treatment.
FIG. 20D shows the content of total soluble sugars/mg of rosette leaves that was enzymatically determined for each of the plants. This content was evaluated 2 and 5 days after starting the treatment. Different letters indicate samples that are significantly different (p value<0.05).

The 25-day-old 35S:HaWRKY76 (W76-A, W76-B and W76-C) and WT plants subjected to submergence during 5-6 days as described above were further evaluated according to different parameters after recovery. Specifically, the rosette weight of the respective plants was measured 2 and 5 days after the start of treatment (submergence), and the results are shown in FIG. 20A. FIG. 20B is a photograph of the rosettes taken 5 days after the start of treatment. The chlorophyll content of the plants was also measured at 2 and 5 days after the start of treatment, and the results are shown in FIG. 20C. Finally, the total content of soluble sugars (μg/mg leaves) was determined for each of the plants, and the results are shown in FIG. 20D. With respect to the results shown in FIGS. 20A, 20C, and 20D, an Anova test was performed, followed by a Fisher LSD post-hoc test. Error bars correspond to the standard deviations from four biological replicas. Different letters indicate samples that were found to be significantly different (i.e., p value<0.05).

Example 13

Transgenic *Arabidopsis thaliana* plants bearing the construct 35S:HaWRKY76 were obtained by the floral dip method (see "Constructs" above), and three homozygous lines were selected for further analysis. Soluble carbohydrates and starch were enzymatically determined in the rosettes of 25-day-old 35S:HaWRKY76 and WT plants that had been submerged during 2, 3, or 5 days.

Figure 21:
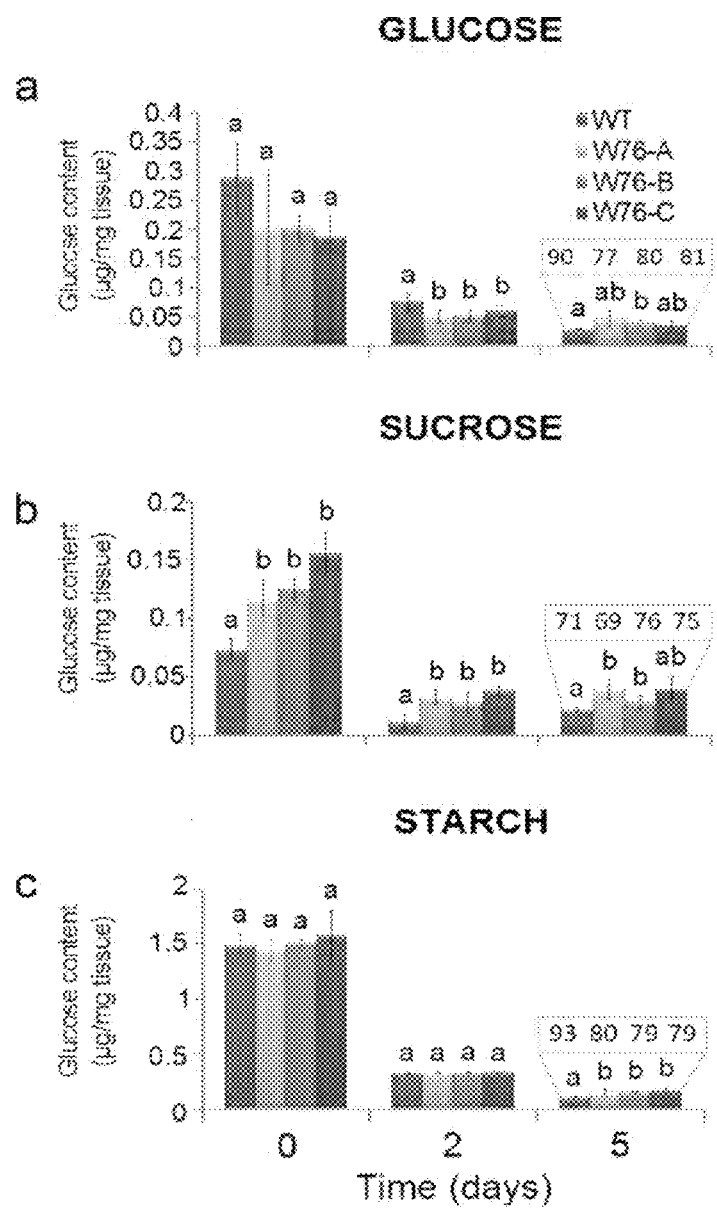
FIGS. 21A-C show the content of soluble carbohydrates and starch in rosettes of 25 day-old plants of three homozygous transgenic lines of *Arabidopsis* transgenic plants bearing the construct 35S:HaWRKY76 and of WT control plants. The 25-day old plants were submerged during 0, 2, 5 days.

FIG. 21A shows the soluble glucose per mg of fresh rosette weight in for each of the plants. FIG. 21B shows the sucrose content in the respective plants, and FIG. 21C shows the starch content in the respective plants. As can be seen from the results of FIG. 21, the transgenic plants have more soluble carbohydrates during submergence than the WT control plants. Error bars correspond to the standard deviations from 4 biological replicas. An Anova test was performed, followed by a Fisher LSC post-hoc test. Different letters (a, b, c, and d) indicate samples that were found to be significantly different (i.e., p value<0.05).

Example 14

Transgenic *Arabidopsis thaliana* plants bearing the construct 35S:HaWRKY76 were obtained by the floral dip method (see "Constructs" above), and three homozygous lines were selected for further analysis. 25-day-old transgenic plants bearing the construct 35S:HaWRKY76 and WT plants were completely submerged during 5 days.

Figure 22:
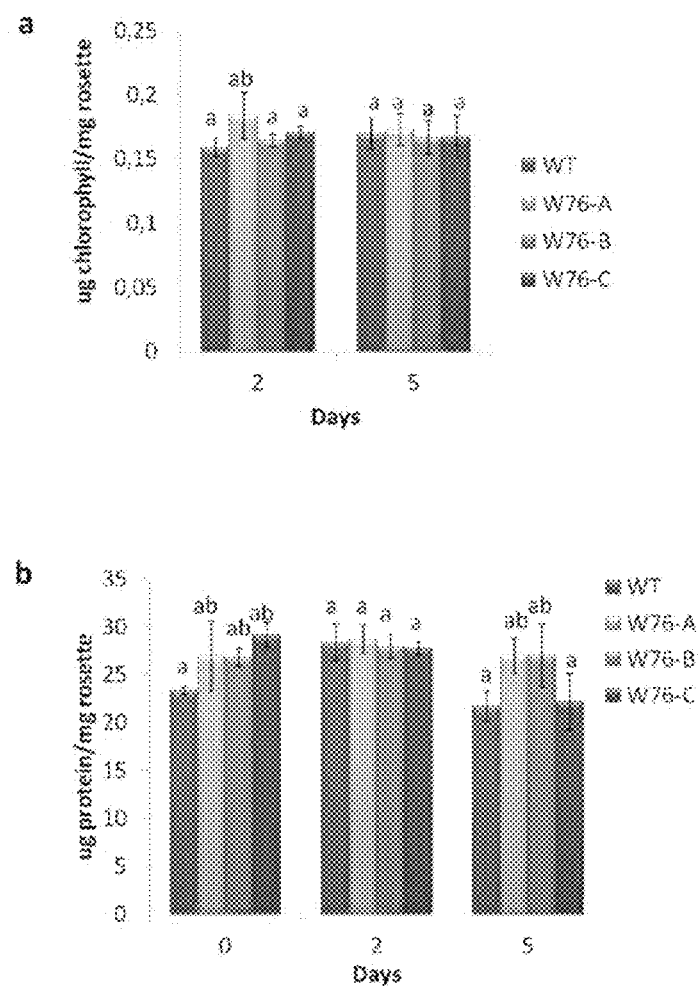
FIG. 22A shows the chlorophyll content per mg fresh rosette weight of 25 day-old plants of three homozygous transgenic lines of *Arabidopsis* transgenic plants bearing the construct 35S:HaWRKY76 and of WT control plants.
FIG. 22B shows the protein content per mg fresh rosette weight of the respective plants. The respective plants were completely submerged during 5 days. Different letters indicate samples that are significantly different (p value<0.05).

FIG. 22A shows the protein content per mg of fresh rosette weight of the respective plants, and FIG. 22B shows the chlorophyll content per mg of fresh rosette weight of the respective plants. As can be seen from the quantified results in FIG. 22, the transgenic plants exhibit higher protein concentrations than the WT control plants during submergence. Error bars correspond to the standard deviations from 4 biological replicas. An Anova test was performed, followed by a Fisher LSC post-hoc test. Different letters (a, b, c, and d) indicate samples that were found to be significantly different (i.e., p value<0.05).

Example 15

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 transgenic plants and WT plants were grown on sand for 35 days. On day 35, the complete root system was collected and weighed.

Figure 23:
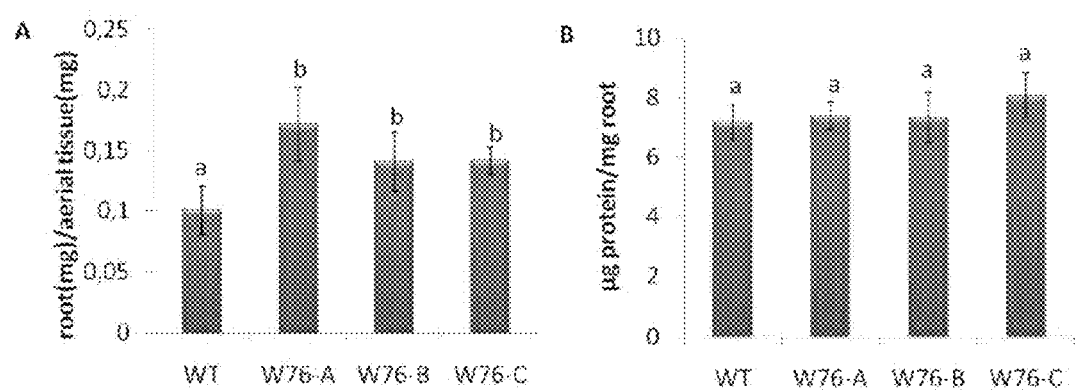
FIG. 23A shows the root/aerial biomass ratio of 35 day-old plants of three homozygous transgenic lines of *Arabidopsis* transgenic plants bearing the construct 35S:HaWRKY76 and of WT control plants.
FIG. 23B shows the root protein content of the respective plants. The respective plants were grown on sand, and on day 35 the complete root system was collected and weighed. Different letters indicate samples that are significantly different (p value<0.05).

FIG. 23A shows the root/aerial biomass ratio for each of the respective plants, and FIG. 23B shows the protein content of the roots collected from each of the respective plants. As can be seen from the results in FIG. 23, the transgenic plants show a higher root/aerial tissue biomass ratio than the WT control plants. Error bars correspond to the standard deviations from 7 biological replicas. An Anova test was performed, followed by a Fisher LSC post-hoc test. Different letters (a, b) indicate samples that were found to be significantly different (i.e., p value<0.05).

Example 16

Figure 24:
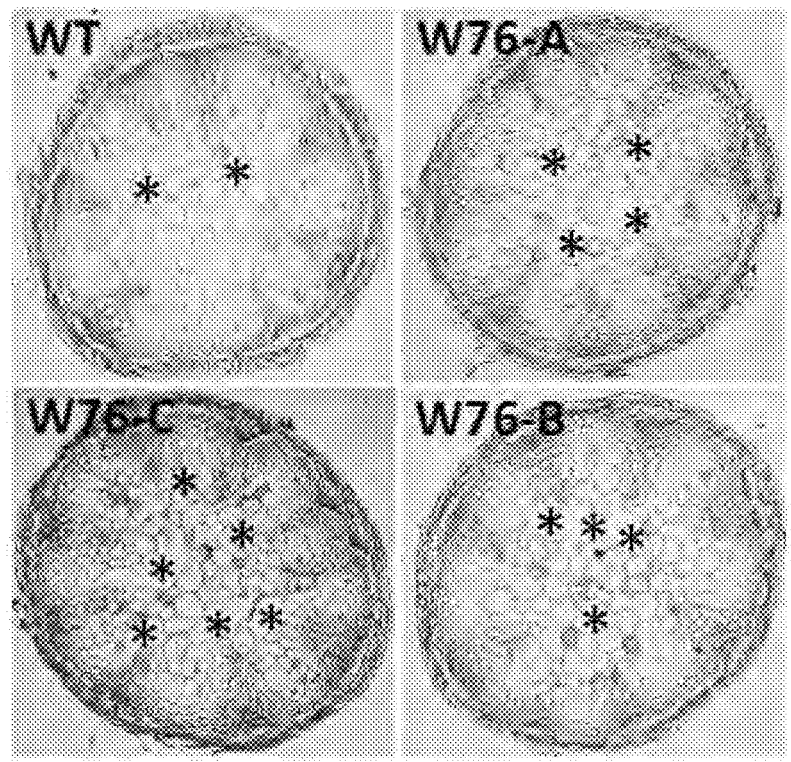
FIG. 24 includes photographic images of 25 day-old plants of three homozygous transgenic lines of *Arabidopsis* transgenic plants bearing the construct 35S:Ha WRKY76 and of WT control plants. The respective plants were subjected to waterlogging during 5 days, and transverse sections of stems were performed and stained.

Transgenic *Arabidopsis thaliana* plants bearing the construct 35S:HaWRKY76 were obtained by the floral dip method (see "Constructs" above), and three homozygous lines were selected for further analysis. 25-day-old 35S:HaWRKY76 transgenic plants and WT plants were subjected to waterlogging during 5 days. Transverse sections of stems of the respective plants were then obtained and stained. The results are shown in the photographs of FIG. 24. As can be seen from FIG. 24, the transgenic plants exhibit more aerenchyma than the WT control plants.

Example 17

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were initially grown in standard growing conditions, then subjected to submergence during 5 days, and finally recovered during one additional day. The sucrose content of the respective plants was measured.

Figure 25:
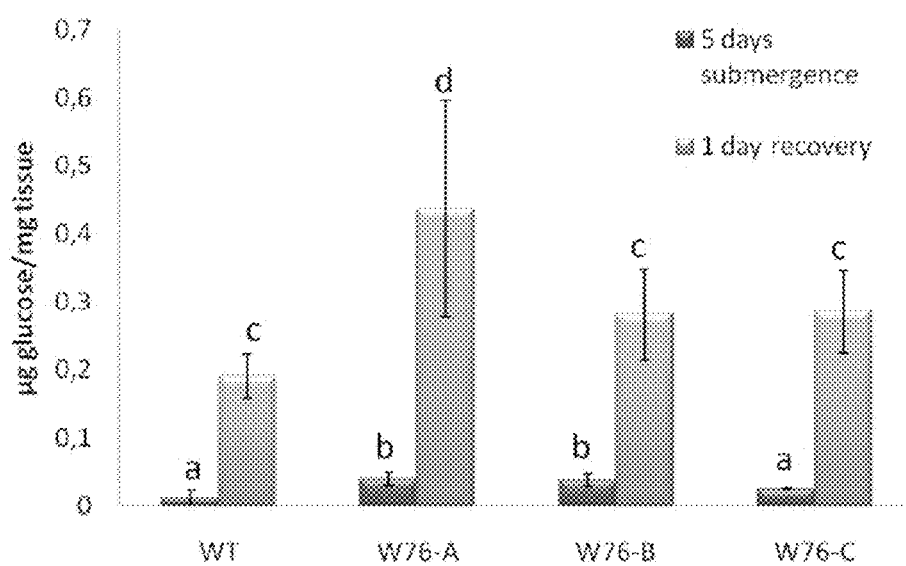
FIG. 25 shows the average glucose content obtained from 4 plants of each genotype (three homozygous transgenic lines of *Arabidopsis* transgenic plants bearing the construct 35S:HaWRKY76 and WT control plants) evaluated both after 5 days of complete submergence and one day after recovery. Different letters indicate samples that are significantly different (p value<0.05).

FIG. 25 shows the sucrose content expressed as μg of glucose/mg of leaves, with each bar representing the average value obtained from 4 plants. An Anova test was performed, followed by a Fisher LSC post-hoc test. Error bars correspond to the standard deviations from 4 biological replicas. Different letters (a, b, c, and d) indicate samples that were found to be significantly different (i.e., p value<0.05).

As demonstrated by the results shown in FIG. 25, the transgenic plants exhibit higher sucrose content after submerge than the WT control plants.

Example 18

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were initially grown in standard growing conditions. Thereafter, 25-day-old plants of each genotype were completely submerged during 5 days and placed in standard growing conditions until recovery. The average yield was measured in 5 plants per genotype.

Figure 26:
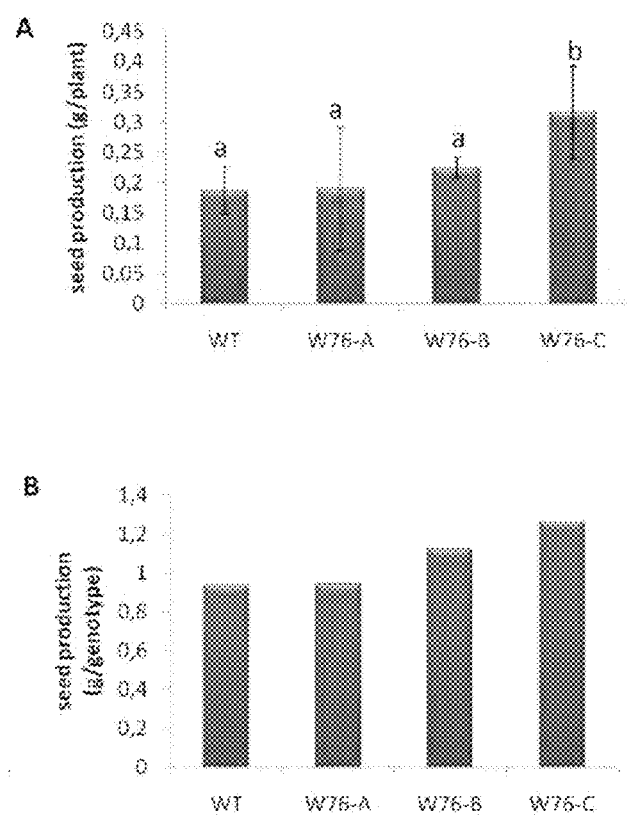
FIG. 26 shows the average yield (at the end of the life cycle) of 25-day-old plants of each genotype (three homozygous lines of *Arabidopsis* transgenic plants bearing the construct 35S:HaWRKY76 and WT control plants) that were grown in standard growing conditions, then completely submerged during 5 days, and then recovered. Different letters indicate samples that are significantly different (p value<0.05).

The results are shown in FIG. 26. An Anova test was performed, followed by a Fisher LSC post-hoc test. Error bars correspond to the standard deviations. Different letters (a and b) indicate samples that were found to be significantly different (i.e., p value<0.05).

As demonstrated by the results shown in FIG. 26, the transgenic plants exhibited slightly higher yields than the WT control plants after 5 days of submergence.

Example 19

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were grown on soil for 25 days. Then, the 25-day-old plants of each genotype were subjected to waterlogging treatment during one week. The tolerance of the respective plants to the waterlogging treatment was measured with respect to the rosette weight, membrane stability, and stem length.

Figure 27:
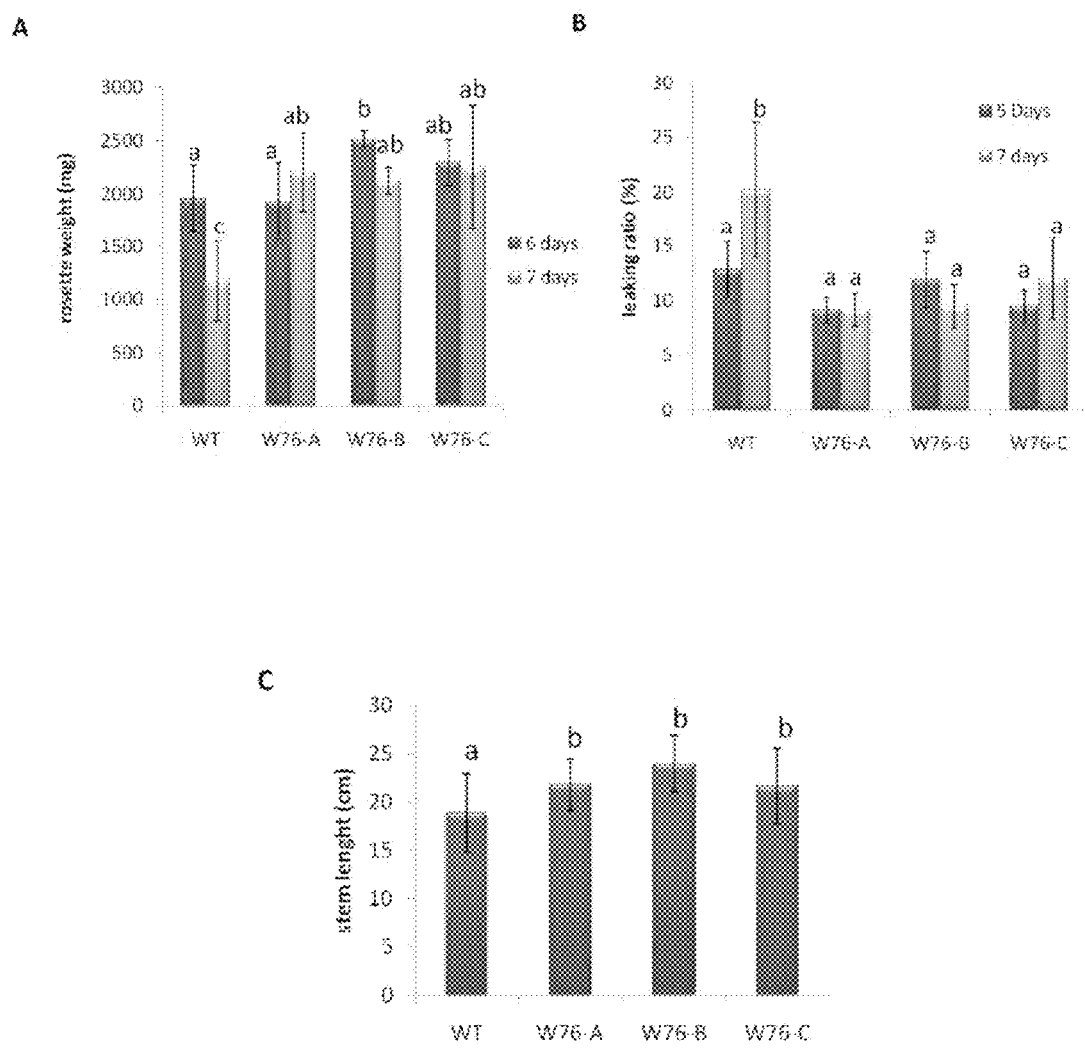
FIG. 27A shows rosette weight measured 6 and 7 days after waterlogging was applied during a week in 25-day-old plants of each genotype grown on poor soil conditions.
FIG. 27B shows the membrane stability of the respective plants, evaluated 5 and 7 days after the start of waterlogging.
FIG. 27C shows the stem length of the respective plants after waterlogging. Different letters indicate samples that are significantly different (p value<0.05).

Panel (A) of FIG. 27 shows the rosette weights of the plants measured 6 and 7 days after starting the waterlogging treatment. Panel (B) of FIG. 27 shows the membrane stability (% of ion leakage) measured 5 and 7 days after starting the treatment. Panel (C) of FIG. 27 shows the stem lengths of the plants after the waterlogging treatment, measured with a ruler. An Anova test was performed, followed by a Fisher LSD post-hoc test. Error bars correspond to standard deviations from 4 biological replicas. Different letters indicate samples that were found to be significantly different (i.e., p value<0.05).

As demonstrated by the results shown in FIG. 27, the 35S:HaWRKY76 transgenic plants are more tolerant to waterlogging than the WT control plants.

Example 20

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were grown on poor soil for 25 days. Then, the 25-day-old plants of each genotype were subjected to waterlogging treatment during one week. The 35S:HaWRKY76 and WT plants seeds were harvested and weighed after the waterlogging treatment. All of the plants survived the waterlogging treatment.

Figure 28:
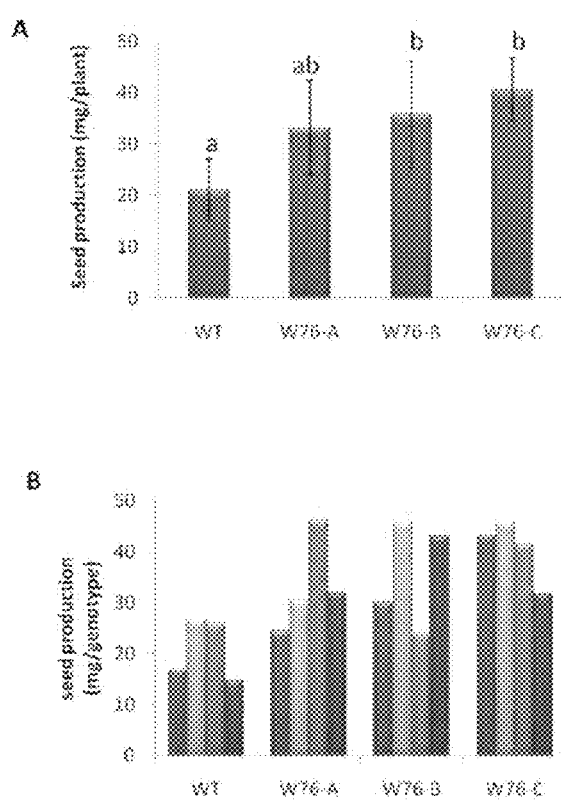
FIGS. 28A and 28B show the average yield and the yield of each plant at the end of the life cycle, respectively, after one week of the waterlogging treatment that was applied to 25-day old plants as described in FIG. 27. Different letters indicate samples that are significantly different (p value<0.05).

Panel (A) of FIG. 28 shows the average yield per genotype. Panel (B) of FIG. 28 shows the yield of each plant, the horizontal line representing the average value of the WT plants. An Anova test was performed, followed by a Fisher LSD post-hoc test. Error bars correspond to standard deviations from 4 biological replicas. Different letters (a and b) indicate samples that were found to be significantly different (i.e., p value<0.05).

As demonstrated by the results shown in FIG. 28, the 35S:HaWRKY76 transgenic plants exhibit higher yields after waterlogging than the WT control plants.

Example 21

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were grown in standard soil, and then subjected to a waterlogging treatment during one week. All of the plants survived the waterlogging treatment.

Figure 29:
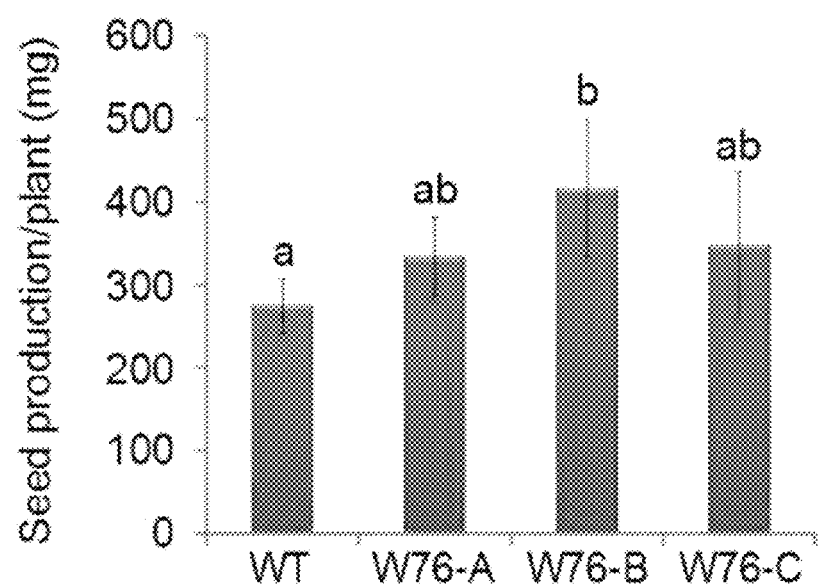
FIG. 29A shows the average yield per genotype.
FIG. 29B shows the yield of all plants of each genotype (three homozygous transgenic lines of *Arabidopsis* transgenic plants bearing the construct 35S:Ha WRKY76 and WT control plants) that were subjected to a waterlogging treatment during one week after being grown in standard soil. Different letters indicate samples that are significantly different (p value<0.05).

Following the waterlogging treatment, seeds of the 35S:HaWRKY76 and WT plants were harvested and weighed. The top panel of FIG. 29 shows the average yield per genotype, whereas the bottom panel of FIG. 29 shows the yield of all the plants of each genotype. An Anova test was performed, followed by a Fisher LSD post-hoc test. Error bars correspond to standard deviations from 4 biological replicas. Different letters (a and b) indicate samples that were found to be significantly different (i.e., p value<0.05).

As demonstrated by the results shown in FIG. 29, the 35S:HaWRKY76 transgenic plants exhibit higher yields after a week of waterlogging than the WT control plants.

Example 22

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were grown in standard growing conditions.

Figure 30:
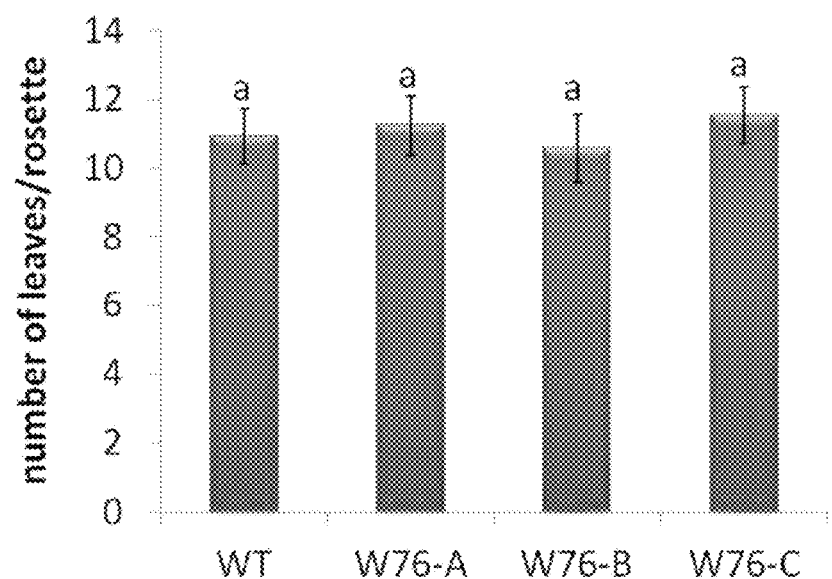
FIG. 30 shows the number of rosette leaves exhibited by plants belonging to three homozygous transgenic lines of *Arabidopsis* transgenic plants bearing the construct 35S:Ha WRKY76 and WT control plants that were grown in standard conditions. Different letters indicate samples that are significantly different (p value<0.05).

The number of rosette leaves of the 35S:HaWRKY76 and WT plants was counted, and the results are shown in FIG. 30. Error bars correspond to the standard deviations from eight biological replicas. As demonstrated by the results shown in FIG. 30, when grown in standard conditions, the transgenic plants do not exhibit significant differences in the number of leaves/rosettes in comparison to the WT control plants.

Example 23

Transgenic *Arabidopsis thaliana* plants bearing the construct 35S:HaWRKY76 were obtained by the floral dip method (see "Constructs" above), and three homozygous lines were selected for further analysis. The 35S:HaWRKY76 (W76-A, W76-B and W76-C) and WT plants were grown in standard growing conditions.

Figure 31:
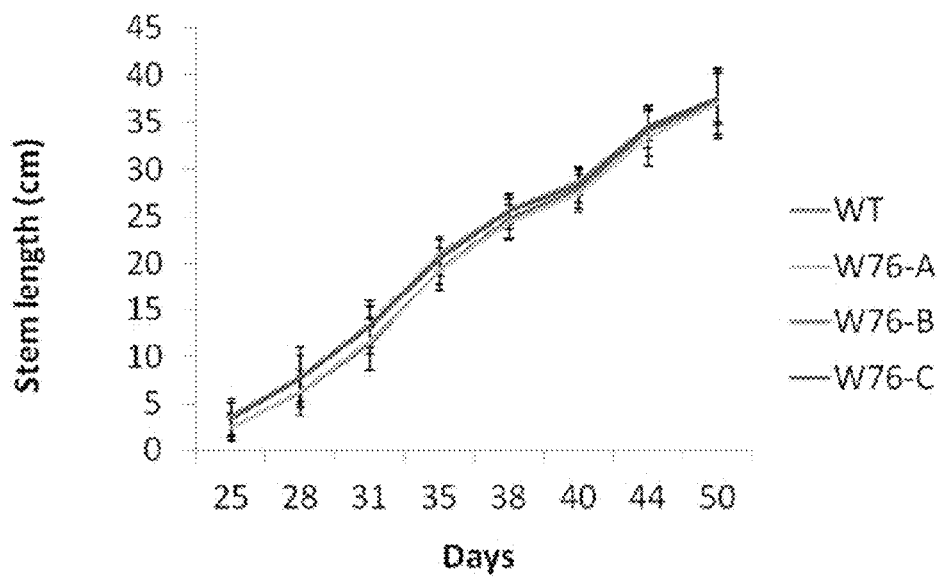
FIG. 31 shows the stem lengths measured during the life cycle of plants belonging to three homozygous transgenic lines of *Arabidopsis* transgenic plants bearing the construct 35S:HaWRKY76 and WT control plants. Different letters indicate samples that are significantly different (p value<0.05).

The stem lengths of the 35S:HaWRKY76 and WT control plants was measured during their life cycle. Specifically, the stem lengths were measured every 3-5 days starting during the plants transition from the vegetative to the reproductive stage. The results are shown in FIG. 31. Error bars correspond to the standard deviations from eight biological replicas. As demonstrated by the results shown in FIG. 31, when grown in standard conditions, the 35S:HaWRKY76 transgenic plants do not exhibit a delay in their life cycle in comparison to the WT control plants.

Example 24

Figure 32:
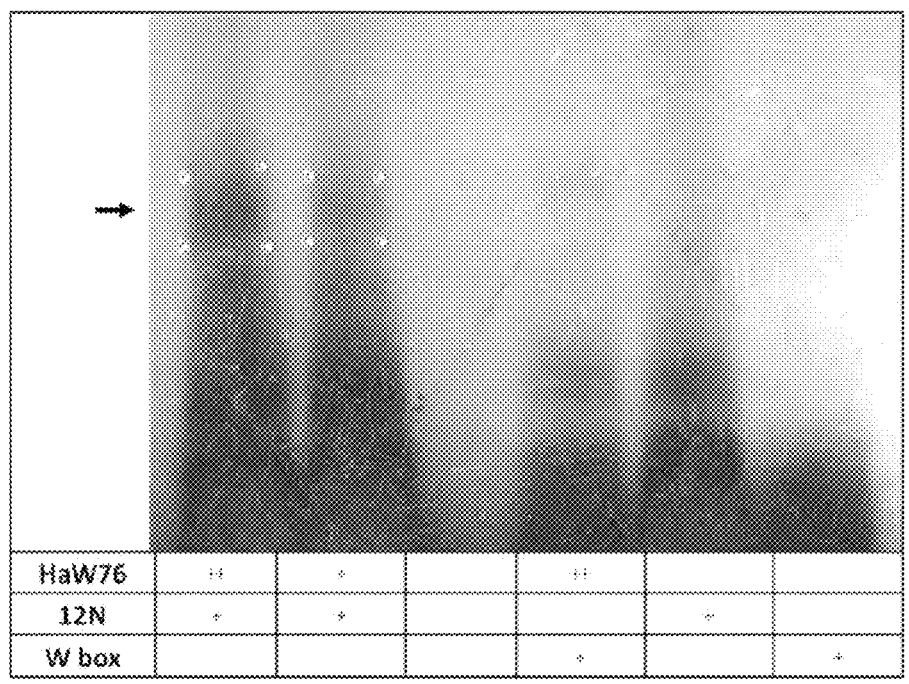
FIG. 32 is an image of an EMSA assay performed with purified recombinant HaWRKY76-GST. 12N is a double stranded oligonucleotide exhibiting a random sequence whereas W-Box is a double stranded oligonucelotide having the canonical W-box.
Figure 33:
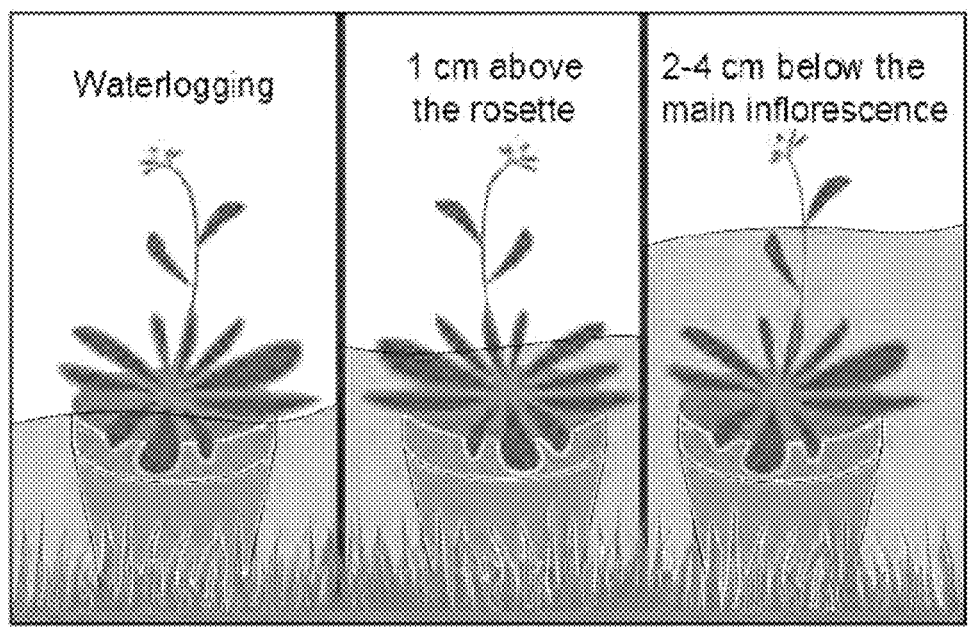
FIG. 33 is a schematic representation of three kinds of assays with different water levels: a) hardly on the substrate, b) 1 cm above the rosette leaves, and c) 2-4 cm below the basal portion of the main inflorescence.
Figure 34:
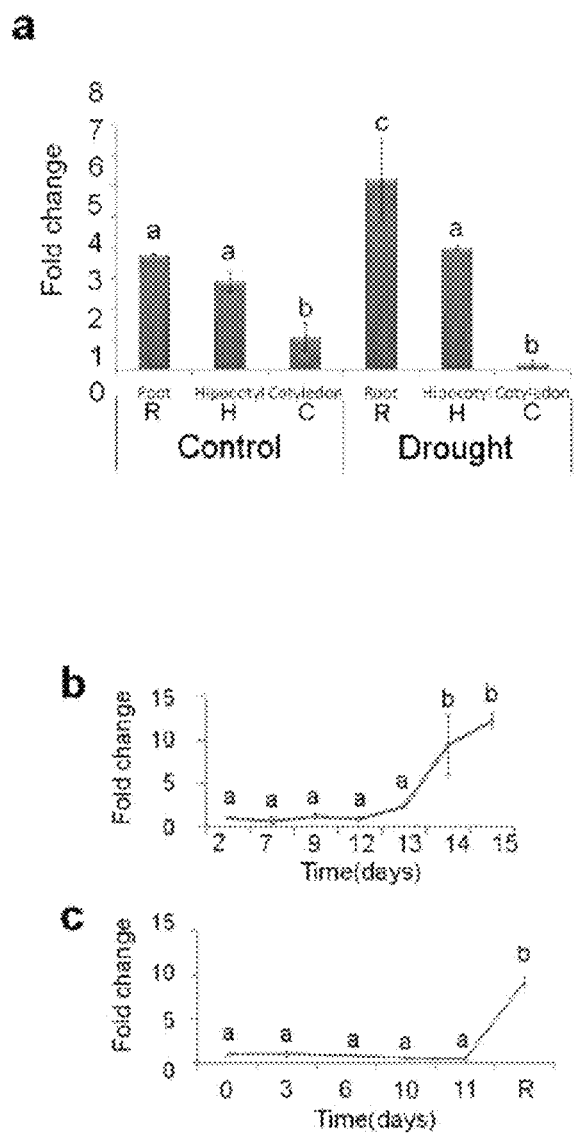
FIG. 34 HaWRKY76 expression in sunflower. (a) 5-day-old seedlings well irrigated (control panel) or exposed to severe water stress (drought panel), (b) 15-day-old plantlets (time 0) exposed to severe drought stress or (c) submergence during 11 days and recovery (R). Transcript levels of HaWRKY76 were quantified by RT-qPCR, normalized with sunflower actin (ACTIN2 and ACTIN8), and thereafter with respect to the value (a) measured in the cotyledon sample under control conditions, (b) in the sample exposed to water stress during 2 days, or (c) in the beginning of the treatment, the three arbitrarily assigned a value of one. Two independent experiments were done and error bars correspond to standard deviations from three biological replicas in each experiment. An ANOVA test was performed, followed by a Fisher LSD post-hoc test. Different numbers of asterisks indicate samples with significant differences (P<0.05).

FIG. 32 is an image of an EMSA assay performed with purified recombinant HaWRKY76-GST. Lines 1 and 2 are 20 ng of W2-GST with a 12N labeled nucleotide (10,000 and 17,000 cpm respectively). Line 4 is 20 ng of W2-GST with 10,000 cpm of labeled oligonucleotide exhibiting 2 W-Boxes (C/TTGACT/C) separated by 5 nucleotides. Lines 5 and 6 are negative controls without the protein and with the same amount of labeled oligonucleotides used in lines 2 and 4 respectively.

The results of the assay show that the recombinant protein HaWRKY76 binds with more affinity an oligonucleotide with a central core 12N (4 nucleotides per position) than a selected oligonucleotide exhibiting two W-Boxes separated by 5 nucleotides. This indicates a different binding affinity than their related WRKY proteins.

Incorporation By Reference

All references and nucleotide and polypeptide sequences cited are hereby incorporated by reference in their entireties herein.

Sequence Information

HaWRK76 cDNA

SEQ ID NO: 1 atggcggttgatttcgtcggaattcaatctaccgatcatcttctaaaccg catgttccagttattaagtcacgatttaaacgtttcgtcaacctacacgc acgcggtttctgctttcaaacgcaccggtcacgcacggttccgccgtgga ccgtcgtctaccaccggagacactaacggaccttcaacttcttcacattc ggaaggtaaatcacgagatacgacttcgtttgtacaaaacgagtgttttt -continued
```
caaacaaaccggtgacggagataacgacgacgacgacgtcaacgagctcg
tcgtctgtagtatcgtcttccaccggtggaaacttagacggaagtgtttc
caacggtaaacagttttcttcgttaggtatagtagctccggcgccgacgt
tctcgtctagaaaaccaccgttaccgtcgacacaccggaaaaggtgcggc
gctgatcgtcctgttgcttccgtacacggatccggaagcggttgccattg
ttgttccaagagaaggaaaaccggatctaaacgtgaaattagaagagttc
cgattaccggatctaaaattacaagcatacctgctgatgattactcatgg
aaaaagtacggcgagaagaagatcgacggttcactttatccacgagtata
ttacaaatgtattaccggaaaaggatgtccggcgaggaagcgcgtggagt
taagcgccgacgattcgaagatgcttattgttacttacgacggagaacac
cgtcaccgtgaccgtcacgcgccggtacctatgagtttgaccggtgtgta
tggtgagccaaagtgaa
```

HaWRK76 protein
                                SEQ ID NO: 2
MAVDFVGIQSTDHLLNRMFQLLSHDLNVSSTYTHAVSAFKRTGHARFRRG
PSSTTGDTNGPSTSSHSEGKSRDTTSFVQNECFSNKPVTEITTTTTSTSS
SSVVSSSTGGNLDGSVSNGKQFSSLGIVAPAPTFSSRKPPLPSTHRKRCG
ADRPVASVHGSGSGCHCCSKRRKTGSKREIRRVPITGSKITSIPADDYSW
KKYGEKKIDGSLYPRVYYKCITGKGCPARKRVELSADDSKMLIVTYDGEH
RHRDRHAPVPMSLTGVYGEPK HaT131007971 GENE
                                SEQ ID NO: 3
```
cccccttctaccccctcatatctctcatcaatctctctttctctctcttag
ggtttcaacttccaaccttcttctacaacaatggcggttgatttcgtcgg
aattcaatctaccgatcatcttctaaaccgcatgttccagttattaagtc
acgatttaaacgtttcgtcaacctacacgcacgcggtttctgctttcaaa
cgcaccggtcacgcacggttccgccgtggaccgtcgtctaccaccggaga
cactaacggaccttcaacttcncacattcggaaggtaaatcacgagatac
gacttcgtttgtacaaaacgagtgtttttcaaacaaatcggtgacggaga
taacgacgacgacgacgtcaacgagctcgtcgtctgtagtatcttcttcc
accggtggaaacttagacggaagtgtttccaacggtaaacagttttcttc
gttaggtatagtagctccggcgccgacgttctcgtctagaaaaccaccgt
taccgtcgacacaccggaaaaggtgcggcgctgatcgtcctgttgcttcc
gtacacggatccggaagcggttgccattgttgttccaagagaaggaaaac
cggatctaaacgtgaaattagaagagttccgattaccggatctaaaatta
caagcatacctgctgatgattactcatggaaaaagtacggcgagaagaag
atcgacggttcactttatccacgagtatattacaaatgtattaccggaaa
aggatgtccggcgaggaagcgcgtggagttaagcgccgacgattcgaaga
tgcttattgttacttacgacggagaacaccgtcaccgtgaccgtcacgcg
ccggtacctatgagtttgaccggtgtgtatggtgagtcaaagtgagggg
acacatgtgtggtccgtgagcactttgcacagttnctaaggtcaacagga
agagagagaaaataactattttattcttggtttagttgagggttaatttg
tacatttgacaaaagatgaagggtgtaattggtaatttagaagatgcccc
cagatctgatattcgatttttgtttggactaattactttataaaagttgat
attggtatatttaaaatttaattaaagaggaaaagtaattagtccaaaca
aaatcgaatatcagatctg
```

HaT131007971 PROTEIN
                                SEQ ID NO: 4
Met Ala Val Asp Phe Val Gly Ile Gln Ser Thr Asp
His Leu Leu Asn Arg Met Phe Gln Leu Leu Ser His
Asp Leu Asn Val Ser Ser Thr Tyr Thr His Ala Val
Ser Ala Phe Lys Arg Thr Gly His Ala Arg Phe Arg
Arg Gly Pro Ser Ser Thr Thr Gly Asp Thr Asn Gly
Pro Ser Thr Ser Ser His Ser Glu Gly Lys Ser Arg
Asp Thr Thr Ser Phe Val Gln Asn Glu Cys Phe Ser
Asn Lys Ser Val Thr Glu Ile Thr Thr Thr Thr Thr
Ser Thr Ser Ser Ser Ser Val Val Ser Ser Ser Thr
Gly Gly Asn Leu Asp Gly Ser Val Ser Asn Gly Lys
Gln Phe Ser Ser Leu Gly Ile Val Ala Pro Ala Pro
Thr Phe Ser Ser Arg Lys Pro Pro Leu Pro Ser Thr
His Arg Lys Arg Cys Gly Ala Asp Arg Pro Val Ala
Ser Val His Gly Ser Gly Ser Gly Cys His Cys Cys
Ser Lys Arg Arg Lys Thr Gly Ser Lys Arg Glu Ile
Arg Arg Val Pro Ile Thr Gly Ser Lys Ile Thr Ser
Ile Pro Ala Asp Asp Tyr Ser Trp Lys Lys Tyr Gly
Glu Lys Lys Ile Asp Gly Ser Leu Tyr Pro Arg Val
Tyr Tyr Lys Cys Ile Thr Gly Lys Gly Cys Pro Ala
Arg Lys Arg Val Glu Leu Ser Ala Asp Asp Ser Lys
Met Leu Ile Val Thr Tyr Asp Gly Glu His Arg His
Arg Asp Arg His Ala Pro Val Pro Met Ser Leu Thr
Gly Val Tyr Gly Glu Ser Lys

HuCL13748C001 GENE
                                SEQ ID NO: 5
```
cttggcggggatcatctctctttctctctctctcttagggtttcaact
tccaaccttcttctacaacaatggcggttgatttcgtcggaattcaatct
acagatcatcatctaaaccgcatgtttcagttatcaactcacgatttaaa
cgtttcgtcaacctacacacgcggtttctgctttcaaacgcaccggtc
acgcacggttccgccgtggaccgtcgtctaccaccggagacactaacgga
ccttcaacttcttcacattcggaaggtaaatcacgagatacgacgtcgtt
tgtacaaaacgagtgtttttcaaacaaatcggtgacggagataacgacga
cgacgacgtcaacgagctcgtcgtctgtagtatcgtcttccaccggtgga
aacttagacggaagtgtttccaacggtaaacagttttttcgttaggtat
agtagctccggcgccgacgttctcgtctagaaaaccaccgctaccgtcga
ctcatcggaaaaggtgcagcgctgatcgtcctgttgcttccgtacacgga
tctggaagcggttgccattgttgttccaagagaaggaaaaccggatctaa
```

```
acgtgaaattagaagagttccgattaccggatctaaaattacaagcatac
ctgctgatgattactcatggaaaaagtacggcgagaagaagatcgacgt
tcactttatccacgagtgtattacaaatgtattaccggaaaaggatgtcc
ggcgaggaagcgcgtggagttaagcgccgacgattcgaagatgcttattg
ttacttacgacggagaacaccgtcaccgtgaccgtcacgtgccggtactt
atgagtttgaccggtgtgtatggtgagtcaaagtgagggggacacatgtg
t
```

HuCL13748C001 PROTEIN

SEQ ID NO: 6

Met Ala Val Asp Phe Val Gly Ile Gln Ser Thr Asp
His His Leu Asn Arg Met Phe Gln Leu Ser Thr His
Asp Leu Asn Val Ser Ser Thr Tyr Thr His Ala Val
Ser Ala Phe Lys Arg Thr Gly His Ala Arg Phe Arg
Arg Gly Pro Ser Ser Thr Thr Gly Asp Thr Asn Gly
Pro Ser Thr Ser Ser His Ser Glu Gly Lys Ser Arg
Asp Thr Thr Ser Phe Val Gln Asn Glu Cys Phe Ser
Asn Lys Ser Val Thr Glu Ile Thr Thr Thr Thr Thr
Ser Thr Ser Ser Ser Val Val Ser Ser Ser Thr
Gly Gly Asn Leu Asp Gly Ser Val Ser Asn Gly Lys
Gln Phe Phe Ser Leu Gly Ile Val Ala Pro Ala Pro
Thr Phe Ser Ser Arg Lys Pro Pro Leu Pro Ser Thr
His Arg Lys Arg Cys Ser Ala Asp Arg Pro Val Ala
Ser Val His Gly Ser Gly Ser Gly Cys His Cys Cys
Ser Lys Arg Arg Lys Thr Gly Ser Lys Arg Glu Ile
Arg Arg Val Pro Ile Thr Gly Ser Lys Ile Thr Ser
Ile Pro Ala Asp Asp Tyr Ser Trp Lys Lys Tyr Gly
Glu Lys Lys Ile Asp Gly Ser Leu Tyr Pro Arg Val
Tyr Tyr Lys Cys Ile Thr Gly Lys Gly Cys Pro Ala
Arg Lys Arg Val Glu Leu Ser Ala Asp Asp Ser Lys
Met Leu Ile Val Thr Tyr Asp Gly Glu His Arg His
Arg Asp Arg His Val Pro Val Leu Met Ser Leu Thr
Gly Val Tyr Gly Glu Ser Lys

SEQ ID NO: 7
WKKYGEK

SEQ ID NO: 8
WRKYGQK

HaWRK76 genomic DNA

SEQ ID NO: 9
```
aatacaattgattactcagtcgaataatggccaatatccgttcataatcg
acgacgacgtcactagggttttttctcttccggttaccaggcctatcatc
tggtttctggtttattttgagggtgagggttttgcattgattcctacgct
ccaatcatctgcttcctgaattgaatctgaatctgaatctgaaagttaac
tagacccctcaagttgtcattcgtaacaactaagcgtctggagattccaa
gcattttatcgtgtgttgtaattttaatgaagcaatgaagattgaatatg
cactagggtgagggttttgcattgattcctgcgctccaatcatctgcttc
ctgaattgaatctgaatctgaaagttaactagacccctcaagttgtcatt
cgtaacaactaagcgtctggagaagagtatgttgatataggagagttgaa
cccgacacgtcttctgtgatgattcaaaacattccgaataactagcagaa
cccgatccacttacattcgaataacgctgagaatccacaacgcttatggc
cagattctttccttcaatcttggcaaaatcaatgcctgcttgttttatta
tcacgaaagtactgaacaaccgagataggcacaataacaacaacagcttt
ccatgatttggagactgatcggaatcgaatcagtgattttactggaagcc
gttttgattatgttttattatcacgaaagtactgaacaaccgagatagaca
caataacaacaacaactttccatgatttggagactgatcagaatcgaaac
agtgattttactttactggaagccgtttgattatttcctcttggatctcg
aaaggcacgttgtctgacatcttgattttgattaccaactcaccatatca
atttctaggtagttaacaacgctaattagaaaaaaaaacgtgattcatat
acacaacggtctctttgcttcgtccactagaactatttgtgtatgcattc
ttttggtagttaacaacgctaattagaaaaaaatctgtaaaattaatcat
atcgattgctataacaggatggatgtgacacacacagatagataagctgt
cacagttgtcaagactgtttgtcgggtttccaatgctcacacagggtgat
aaacaatgctgatacgaacacatgtgtttcgaaataggcttttgttcttgg
tttaatgaagttacatgtaacatctacttatattcagatttaaacaatgc
ccgcctcaactgagataacggacatccatcaagctcaaaaagaaaacttg
tgtttcccatagtcacaaaagattgcggtttgtatttcgcatagccaccg
tttccgtagtaaaaaacggttgcggtttgtatttcgcatagccaccgtttt
ccgtagtaaaaaacggttgggtttgcacattcaatcttcaatacttcatt
aaaataccactagtagaagaacccgacacgtcttcatgttacggagaatg
ttctacaaattgaaggaaaaggaaaagatttgttgaaatcgaatttgaca
actatgacagcttattaaaagtagcaatcacctccaatcatttcctggtc
aaatcacacaccataaagtttaaagttatcgtgtgttgtagtttggaaag
atgaccgaacaaagatctgaataacaaactgtggagaacttgtttgtgtc
gggtcttctgctagttacttgatcaacggactgatcgttaacgttactc
tacttgtgctccgatttaagcggcgtgttccgatcaacgttgtttaaagg
tgatgaagagtttagaaacccctagaatgatggtgcttttacgggaaaaa
cgtgataattgaaaaacatcaatctatacggcctgtatacaattatacgg
cccgtatacatttggtaaacatcaaaaacctcccaaaataaatccattga
gccgtatagttttacaaatcgtatacacatgtatacggctcgtataact
atatacgggccgtatatgtaaaaaaaacattctttacgcattgtcctat
taaaaaacattctatacggaccgtatattttgtatacggtccgtataaac
taaagtatgaaaataaaatatagggggtgtgggaataagaggagcgtta
ttaaaatacacaaataattttcgtcatgactccaactacatgttttattg
tgttcttgtttgtcgttattaatattttctttgacatagaaagtcgaaac
gcatggtatccagctacgtacacatttattcaacttatatttattttagt
```

```
cctcgtttgactttatgcctccactagctttctccatctgtttatcacgc
tgcaaataagtcaaacaattctccaccgtccgatcaaaacagtatctcat
tgactccactttcccaattggacctttataaccccttctacccctcata
tctctcatcaatctctctttctctctcttagggtttcaacttccaacctt
cttctacaacaatggcggttgatttcgtcggaattcaatctaccgatcat
cttctaaaccgcatgttccagttattaagtcacgatttaaacgtttcgtc
aacctacacgcacgcggtttctgctttcaaacgcaccggtcacgcacggt
tccgccgtggaccgtcgtctaccaccggagacactaacggaccttcaact
tcttcacattcggaaggtaaatcacgagatacgacttcgtttgtacaaaa
cgagtgttttcaaacaaatcggtgacggagataacgacgacgacgacgt
caacgagctcgtcgtctgtagtatcttcttccaccggtggaaacttagac
ggaagtgtttccaacgtaaacagttttcttcgttaggtatagtagctcc
ggcgccgacgttctcgtctagaaaaccaccgttaccgtcgacacaccgga
aaaggtgcggcgctgatcgtcctgttgcttccgtacacggatccggaagc
ggttgccattgggaaaaccggatctaaacgtgaaattagaagagttccga
ttaccggatctaaaattacaagcatacctgctgatgattactcatggaaa
aagtacggcgagaagaagatcgacggttcactttatccacgagtatatta
caaatgtattaccggaaaaggatgtccggcgaggaagcgcgtggagttaa
gcgccgacgattcgaagatgcttattgttacttacgacggagaacaccgt
caccgtgaccgtcacgcgccggtacctatgagtttgaccggtgtgtatgg
tgagtcaaagtgaggggacacatgtgtggtccgtgagcactttgcacag
ttttctaaggtcaacaggaagagagagaaattaactttttttattcttgg
tttagttgagggttaatttgtacatttgacaaaagatgaagggtgtaatt
ggtaatttagaagatgccccagatctgatattcgattttgtttggactaa
ttactttataaaagttgatattggtatatttaaaatttaattaaagagga
aaagtaatttgaataagtttgatgccacagcagagtcaatgggttttaaa
gtctctttaaatgactaaaaaattagataattgaatgaattttttaatgg
caaatgtagtctttattttcatatttattatggtcgttggtgcgacttt
ggcaaattgatttcgacaatgtattgatggcgatgatctggaatggtcca
atccaatttttatttgttttattgtttaatatttaggagactttggaaa
aatagcaagggttgaccctgatgaatattaataagtgtgtttactaaag
aagcaagaatgtaacagctagcgatgagatgttaactaacgggtaccgta
ttgatgtcgagctaaaaccaaaaccaaataacataatgtgtatgttcagt
tggtattggtattatacggtaccgctaaaaatcccaaacaggtaagtgcc
acatggtatcgatactgcagcttagataaaataaaattgaatatcacacc
gtatatgtttggtcgacatcaataacaggtattcggtatgaagtttccca
tctcaagactggcacgtaatatcatatatatacaactatagttggtttta
tactttcggagtttacggtttcaacttctattagtttgggtgaagagcatc
caagaggtcatcaatctgta
```

HaWRK76 promoter 5'UTRs underlined

SEQ ID NO: 10
```
aatacaattgattactcagtcgaataatggccaatatccgttcataatcg
acgacgacgtcactagggttttttctcttccggttaccaggcctatcatc
tggtttctggtttatttgagggtgagggttttgcattgattcctacgct
ccaatcatctgcttcctgaattgaatctgaatctgaatctgaaagttaac
tagacccctcaagttgtcattcgtaacaactaagcgtctggagattccaa
gcattttatcgtgtgttgtaattttaatgaagcaatgaagattgaatatg
cactagggtgagggttttgcattgattcctgcgctccaatcatctgcttc
ctgaattgaatctgaatctgaaagttaactagacccctcaagttgtcatt
cgtaacaactaagcgtctggagaagagtatgttgatataggagagttgaa
cccgacacgtcttctgtgatgattcaaaacattccgaataactagcagaa
cccgatccacttacattcgaataacgctgagaatccacaacgcttatggc
cagattcttccttcaatcttggcaaaatcaatgcctgcttgttttatta
tcacgaaagtactgaacaaccgagataggcacaataacaacaacagcttt
ccatgatttggagactgatcggaatcgaatcagtgatttactggaagcc
gtttgattatgttttattatcacgaaagtactgaacaaccgagatagaca
caataacaacaacaactttccatgatttggagactgatcagaatcgaaac
agtgattttactttactggaagccgtttgattatttcctcttggatctcg
aaaggcacgttgtctgacatcttgatttgattaccaactcaccatatca
atttctaggtagttaacaacgctaattagaaaaaaaaacgtgattcatat
acacaacggtctctttgcttcgtccactagaactatttgtgtatgcattc
ttttggtagttaacaacgctaattagaaaaaaatctgtaaaattaatcat
atcgattgctataacaggatggatgtgacacacacagatagataagctgt
cacagttgtcaagactgtttgtcgggtttccaatgctcacacagggtgat
aaacaatgctgatacgaacacatgtgtttcgaaataggctttgttcttgg
tttaatgaagttacatgtaacatctacttatattcagatttaaacaatgc
ccgcctcaactgagataacggacatccatcaagctcaaaaagaaaacttg
tgtttcccatagtcacaaaagattgcggtttgtatttcgcatagccaccg
tttccgtagtaaaaaacggttgcggtttgtatttcgcatagccaccgttt
ccgtagtaaaaaacggttgggtttgcacattcaatcttcaatacttcatt
aaaataccactagtagaagaacccgacacgtcttcatgttacggagaatg
ttctacaaattgaaggaaaaggaaaagatttgttgaaatcgaatttgaca
actatgacagcttattaaaagtagcaatcacctccaatcatttcctggtc
aaatcacacaccataaagtttaaagttatcgtgtgttgtagtttggaaag
atgaccgaacaaagatctgaataacaaactgtggagaacttgtttgtgtc
gggttcttctgctagttacttgatcaacggactgatcgttaacgttactc
tacttgtgctccgatttaagcggcgtgttccgatcaacgttgtttaaagg
tgatgaagagtttagaaaccctagaatgatggtgcttttacgggaaaaaa
cgtgataattgaaaaacatcaatctatacggcctgtatacaattatacgg
cccgtatacatttggtaaacatcaaaaacctcccaaaataaatccattga
``` gccgtatagttttttacaaatcgtatacacatgtatacggctcgtataact atatacgggccgtatatagtaaaaaaaacattctttacgcattgtcctat taaaaaacattctatacggaccgtatattttgtatacggtccgtataaac taaagatatgaaaataaatataggggggtgtgggaataagaggagcgtta ttaaaatacacaaataattttcgtcatgactccaactacatgttttattg tgttcttgtttgtcgttattaatattttctttgacatagaaagtcgaaac gcatggtatccagctacgtacacatttattcaacttatatttattttagt cctcgtttgactttatgcctccactagctttctccatctgtttatcacgc tgcaaataagtcaaacaattctccaccgtccgatcaaaacagtatctcat tgactccactttcccaattggacctttataacccccttctaccccctcata tctctcatcaatctctctttctctctcttagggtttcaacttccaacctt cttctacaaca variant HaWRK76 cDNA. This has a g in position 220 (underlined) and encodes a protein as shown in SEQ ID No. 12 has an A in the motif SRDAT instead of a T.

SEQ ID NO: 11

Atggcggttgatttcgtcggaattcaatctaccgatcatcttctaaaccg catgttccagttattaagtcacgatttaaacgtttcgtcaacctacacgc acgcggtttctgctttcaaacgcaccggtcacgcacggttccgccgtgga ccgtcgtctaccaccggagacactaacggaccttcaacttcttcacattc ggaaggtaaatcacgagatgcgacttcgtttgtacaaaacgagtgttttt caaacaaaccggtgacggagataacgacgacgacgtcaacgagctcg tcgtctgtagtatcgtcttccaccggtggaaacttagacgaagtgtttc caacggtaaacagttttcttcgttaggtatagtagctccggcgccgacgt tctcgtctagaaaaccaccgttaccgtcgacacaccggaaaaggtgcggc gctgatcgtcctgttgcttccgtacacggatccggaagcggttgccattg ttgttccaagagaaggaaaaccggatctaaacgtgaaattagaagagttc cgattaccggatctaaaattacaagcatacctgctgatgattactcatgg aaaaagtacggcgagaagaagatcgacggttcactttatccacgagtata ttacaaatgtattaccggaaaaggatgtccggcgaggaagcgcgtggagt taagcgccgacgattcgaagatgcttattgttacttacgacggagaacac cgtcaccgtgaccgtcacgcgccggtacctatgagtttgaccggtgtgta tggtgagccaaagtgaa variant HaWRK76 protein. This has an A in the motif SRDAT instead of a T (see underlined A)

SEQ ID NO: 12

MAVDFVGIQSTDHLLNRMFQLLSHDLNVSSTYTHAVSAFKRTGHARFRRG

PSSTTGDTNGPSTSSHSEGKSRDATSFVQNECFSNKPVTEITTTTTSTSS

SSVVSSSTGGNLDGSVSNGKQFSSLGIVAPAPTFSSRKPPLPSTHRKRCG

ADRPVASVHGSGSGCHCCSKRRKTGSKREIRRVPITGSKITSIPADDYSW

KKYGEKKIDGSLYPRVYYKCITGKGCPARKRVELSADDSKMLIVTYDGEH

RHRDRHAPVPMSLTGVYGEPK

---

The invention claimed is:

1. A polynucleotide having at least 95% sequence identity with the full-length nucleotide sequence of SEQ ID NO: 1, wherein the polynucleotide contains at least one of:
   (a) adenine as the nucleotide corresponding to position 817 of the full-length nucleotide sequence of SEQ ID NO: 1;
   (b) cytosine as the nucleotide corresponding to position 808 of the full-length nucleotide sequence of SEQ ID NO: 1;
   (c) cytosine as the nucleotide corresponding to position 33 of the full-length nucleotide sequence of SEQ ID NO: 1;
   (d) cytosine as the nucleotide corresponding to position 259 of the full-length nucleotide sequence of SEQ ID NO: 1; and
   (e) guanine as the nucleotide corresponding to position 315 of the full-length nucleotide sequence of SEQ ID NO: 1.

2. The polynucleotide of claim 1, wherein the polynucleotide contains adenine as the nucleotide corresponding to position 817 of the full-length nucleotide sequence of SEQ ID NO: 1, and cytosine as the nucleotide corresponding to position 808 of the full-length nucleotide sequence of SEQ ID NO: 1.

3. The polynucleotide of claim 1, wherein the polynucleotide has at least 98% sequence identity with the full-length nucleotide sequence of SEQ ID NO: 1.

4. The polynucleotide of claim 1, wherein the polynucleotide has the full-length nucleotide sequence of SEQ ID NO: 1.

5. A vector comprising the polynucleotide of claim 1.

6. A recombinant expression cassette comprising the cDNA polynucleotide of claim 1, wherein the polynucleotide is operably linked to a promoter and is in sense or antisense orientation.

7. The recombinant expression cassette of claim 6, wherein the promoter is selected from the group consisting of a tissue-preferred promoter, a constitutive promoter, and an inducible promoter.

8. The recombinant expression cassette of claim 6, wherein the promoter is a HaWRKY76 promoter.

9. A host cell comprising the vector of claim 5.

10. A recombinant expression cassette comprising the vector of claim 5.

11. A transgenic plant comprising a nucleic acid construct comprising a polynucleotide having at least 90% sequence identity with the full-length nucleotide sequence of SEQ ID NO: 1, wherein the polynucleotide contains at least one of:
    (a) adenine as the nucleotide corresponding to position 817 of the full-length nucleotide sequence of SEQ ID NO: 1,
    (b) cytosine as the nucleotide corresponding to position 808 of the full-length nucleotide sequence of SEQ ID NO: 1,
    (c) cytosine as the nucleotide corresponding to position 33 of the full-length nucleotide sequence of SEQ ID NO: 1,
    (d) cytosine as the nucleotide corresponding to position 259 of the full-length nucleotide sequence of SEQ ID NO: 1, and
    (e) guanine as the nucleotide corresponding to position 315 of the full-length nucleotide sequence of SEQ ID NO: 1.

12. The transgenic plant of claim 11, wherein the nucleic acid construct is a vector.

13. The transgenic plant of claim 11, wherein the nucleic acid construct is a recombinant expression cassette, and wherein the polynucleotide is operably linked to a promoter.

14. The transgenic plant of claim 11, wherein the plant is selected from the group consisting of maize, soybean, sorghum, canola, wheat, alfalfa, cotton, rice, barley, oilseed rape, and millet.

15. A seed from the transgenic plant of claim 11, wherein the seed comprises the nucleic acid construct comprising the polynucleotide.

16. A method of producing a transgenic plant, comprising:
    introducing into a plant cell an expression vector comprising a polynucleotide having at least 90% sequence identity with the full-length nucleotide sequence of SEQ ID NO: 1, wherein the polynucleotide contains at least one of:
    (a) adenine as the nucleotide corresponding to position 817 of the full-length nucleotide sequence of SEQ ID NO: 1,
    (b) cytosine as the nucleotide corresponding to position 808 of the full-length nucleotide sequence of SEQ ID NO: 1,
    (c) cytosine as the nucleotide corresponding to position 33 of the full-length nucleotide sequence of SEQ ID NO: 1,
    (d) cytosine as the nucleotide corresponding to position 259 of the full-length nucleotide sequence of SEQ ID NO: 1, and
    (e) guanine as the nucleotide corresponding to position 315 of the full-length nucleotide sequence of SEQ ID NO: 1; and
    generating from the plant cell a transgenic plant that expresses the polynucleotide.

17. A method of modulating a plant phenotype, comprising:
    introducing and expressing in a plant a nucleic acid construct comprising a polynucleotide having at least 90% sequence identity with the full-length nucleotide sequence of SEQ ID NO: 1, wherein the polynucleotide contains at least one of:
    (a) adenine as the nucleotide corresponding to position 817 of the full-length nucleotide sequence of SEQ ID NO: 1;
    (b) cytosine as the nucleotide corresponding to position 808 of the full-length nucleotide sequence of SEQ ID NO: 1;
    (c) cytosine as the nucleotide corresponding to position 33 of the full-length nucleotide sequence of SEQ ID NO: 1;

(d) cytosine as the nucleotide corresponding to position 259 of the full-length nucleotide sequence of SEQ ID NO: 1; and (e) guanine as the nucleotide corresponding to position 315 of the full-length nucleotide sequence of SEQ ID NO: 1.

18. The method of claim 17 wherein said method increases yield of a plant.

19. The method of claim 17 wherein said method increases tolerance to abiotic and biotic stress conditions.

20. The method of claim 19 wherein said stress is abiotic stress.

21. The method of claim 20 wherein said abiotic stress is selected from drought or irrigation.

22. The method of claim 19 wherein said stress is severe or moderate stress.

23. A recombinant expression cassette comprising a polynucleotide operably linked to a promoter, wherein the polynucleotide encodes a polypeptide comprising a sequence having at least 90% sequence identity with the full-length amino acid sequence of SEQ ID NO: 2, the polypeptide sequence containing at least one of:
(a) proline as the amino acid corresponding to position 270 of the full-length amino acid sequence of SEQ ID NO: 2;
(b) proline as the amino acid corresponding to position 87 of the full-length amino acid sequence of SEQ ID NO: 2;
(c) proline as the amino acid corresponding to position 260 of the full-length amino acid sequence of SEQ ID NO: 2;
(d) serine as the amino acid corresponding to position 123 of the full-length amino acid sequence of SEQ ID NO: 2;
(e) leucine as the amino acid corresponding to position 14 of the full-length amino acid sequence of SEQ ID NO: 2;
(f) leucine as the amino acid corresponding to position 22 of the full-length amino acid sequence of SEQ ID NO: 2; and
(g) serine as the amino acid corresponding to position 23 of the full-length amino acid sequence of SEQ ID NO: 2.

24. A transgenic plant comprising a recombinant polynucleotide encoding a polypeptide comprising a sequence having at least 90% sequence identity with the full-length amino acid sequence of SEQ ID NO: 2, the polypeptide sequence containing at least one of:
(a) proline as the amino acid corresponding to position 270 of the full-length amino acid sequence of SEQ ID NO: 2;
(b) proline as the amino acid corresponding to position 87 of the full-length amino acid sequence of SEQ ID NO: 2;
(c) proline as the amino acid corresponding to position 260 of the full-length amino acid sequence of SEQ ID NO: 2;
(d) serine as the amino acid corresponding to position 123 of the full-length amino acid sequence of SEQ ID NO: 2;
(e) leucine as the amino acid corresponding to position 14 of the full-length amino acid sequence of SEQ ID NO: 2;
(f) leucine as the amino acid corresponding to position 22 of the full-length amino acid sequence of SEQ ID NO: 2; and
(g) serine as the amino acid corresponding to position 23 of the full-length amino acid sequence of SEQ ID NO: 2.

25. The transgenic plant of claim 24, wherein the transgenic plant has improved tolerance to drought, submergence, and/or waterlogging, as well as increased yield, compared to a corresponding wild-type control plant that does not express the polypeptide encoded by the recombinant polynucleotide.

26. The transgenic plant of claim 24, wherein the transgenic plant expresses the polypeptide at elevated levels compared to a corresponding wild-type control plant.

27. A method of producing a transgenic plant, comprising:
introducing into a plant cell an expression cassette comprising a polynucleotide operably linked to a promoter, wherein the polynucleotide encodes a polypeptide comprising a sequence having at least 90% sequence identity with the full-length amino acid sequence of SEQ ID NO: 2, the polypeptide sequence containing at least one of:
(a) proline as the amino acid corresponding to position 270 of the full-length amino acid sequence of SEQ ID NO: 2;
(b) proline as the amino acid corresponding to position 87 of the full-length amino acid sequence of SEQ ID NO: 2;
(c) proline as the amino acid corresponding to position 260 of the full-length amino acid sequence of SEQ ID NO: 2;
(d) serine as the amino acid corresponding to position 123 of the full-length amino acid sequence of SEQ ID NO: 2;
(e) leucine as the amino acid corresponding to position 14 of the full-length amino acid sequence of SEQ ID NO: 2;
(f) leucine as the amino acid corresponding to position 22 of the full-length amino acid sequence of SEQ ID NO: 2; and
(g) serine as the amino acid corresponding to position 23 of the full-length amino acid sequence of SEQ ID NO: 2; and
generating from the plant cell a transgenic plant that expresses the polypeptide.

28. The method of claim 27, wherein the generated transgenic plant expresses the polypeptide at elevated levels compared to a corresponding wild-type control plant.

29. A recombinant expression cassette comprising an isolated polynucleotide operably linked to a promoter, wherein the polynucleotide is a member selected from the group consisting of:
(a) a polynucleotide that encodes the polypeptide of SEQ ID NO: 2; and
(b) the polynucleotide of SEQ ID NO: 1.

30. A transgenic plant comprising the recombinant expression cassette of claim 29.

31. A method of producing a transgenic plant, comprising:
(a) introducing into a plant cell the recombinant expression cassette of claim 29; and
b) culturing the plant cell under plant growing conditions to produce a transgenic plant.

32. The method of claim 17, wherein the polynucleotide is operably linked to a promoter.

33. The method of claim 32, wherein the promoter is selected from the group consisting of a tissue-preferred promoter, a constitutive promoter, and an inducible promoter.

34. The method of claim 17, wherein the plant is selected from the group consisting of maize, soybean, sorghum, canola, wheat, alfalfa, cotton, rice, barley, oilseed rape, and millet.

\* \* \* \* \*

SEQUENCE LISTING

<160> NUMBER OF SEQ ID NOS: 12

<210> SEQ ID NO 1
<211> LENGTH: 817
<212> TYPE: DNA
<213> ORGANISM: Helianthus annuus

<400> SEQUENCE: 1
atggcggttg atttcgtcgg aattcaatct accgatcatc ttctaaaccg catgttccag      60
ttattaagtc acgatttaaa cgtttcgtca acctacacgc acgcggtttc tgctttcaaa     120
cgcaccggtc acgcacggtt ccgccgtgga ccgtcgtcta ccaccggaga cactaacgga     180
ccttcaactt cttcacattc ggaaggtaaa tcacgagata cgacttcgtt tgtacaaaac     240
gagtgttttt caaacaaacc ggtgacggag ataacgacga cgacgtc aacgagctcg     300 tcgtctgtag tatcgtcttc caccggtgga aacttagacg aagtgtttc caacggtaaa     360 cagttttctt cgtaggtat agtagctccg gcgccgacgt tctcgtctag aaaaccaccg     420
ttaccgtcga cacaccggaa aggtgcggc gctgatcgtc ctgttgcttc cgtacacgga     480
tccggaagcg gttgccattg ttgttccaag agaaggaaaa ccggatctaa acgtgaaatt     540
agaagagttc cgattaccgg atctaaaatt acaagcatac ctgctgatga ttactcatgg     600
aaaaagtacg gcgagaagaa gatcgacggt tcactttatc cacgagtata ttacaaatgt     660
attaccggaa aaggatgtcc ggcgaggaag cgcgtggagt taagcgccga cgattcgaag     720
atgcttattg ttacttacga cggagaacac cgtcaccgtg accgtcacgc gccggtacct     780

```
atgagtttga ccggtgtgta tggtgagcca aagtgaa                            817
```

<210> SEQ ID NO 2
<211> LENGTH: 271
<212> TYPE: PRT
<213> ORGANISM: Helianthus annuus

<400> SEQUENCE: 2

Met Ala Val Asp Phe Val Gly Ile Gln Ser Thr Asp His Leu Leu Asn
1               5                   10                  15

Arg Met Phe Gln Leu Leu Ser His Asp Leu Asn Val Ser Ser Thr Tyr
            20                  25                  30

Thr His Ala Val Ser Ala Phe Lys Arg Thr Gly His Ala Arg Phe Arg
        35                  40                  45

Arg Gly Pro Ser Ser Thr Thr Gly Asp Thr Asn Gly Pro Ser Thr Ser
    50                  55                  60

Ser His Ser Glu Gly Lys Ser Arg Asp Thr Thr Ser Phe Val Gln Asn
65                  70                  75                  80

Glu Cys Phe Ser Asn Lys Pro Val Thr Glu Ile Thr Thr Thr Thr Thr
                85                  90                  95

Ser Thr Ser Ser Ser Val Val Ser Ser Thr Gly Gly Asn Leu
            100                 105                 110

Asp Gly Ser Val Ser Asn Gly Lys Gln Phe Ser Ser Leu Gly Ile Val
        115                 120                 125

Ala Pro Ala Pro Thr Phe Ser Ser Arg Lys Pro Pro Leu Pro Ser Thr
    130                 135                 140

His Arg Lys Arg Cys Gly Ala Asp Arg Pro Ala Ser Val His Gly
145                 150                 155                 160

Ser Gly Ser Gly Cys His Cys Cys Ser Lys Arg Lys Thr Gly Ser
                165                 170                 175

Lys Arg Glu Ile Arg Arg Val Pro Ile Thr Gly Ser Lys Ile Thr Ser
            180                 185                 190

Ile Pro Ala Asp Asp Tyr Ser Trp Lys Lys Tyr Gly Glu Lys Lys Ile
        195                 200                 205

Asp Gly Ser Leu Tyr Pro Arg Val Tyr Tyr Lys Cys Ile Thr Gly Lys
    210                 215                 220

Gly Cys Pro Ala Arg Lys Arg Val Glu Leu Ser Ala Asp Asp Ser Lys
225                 230                 235                 240

Met Leu Ile Val Thr Tyr Asp Gly Glu His Arg His Arg Asp Arg His
                245                 250                 255

Ala Pro Val Pro Met Ser Leu Thr Gly Val Tyr Gly Glu Pro Lys
            260                 265                 270

<210> SEQ ID NO 3
<211> LENGTH: 1172
<212> TYPE: DNA
<213> ORGANISM: Helianthus annuus

<400> SEQUENCE: 3

```
cccccttcta cccctcatat ctctcatcaa tctctctttc tctctcttag ggtttcaact     60 tccaacctt c ttctacaaca atggcggttg atttcgtcgg aattcaatct accgatcatc    120
ttctaaaccg catgttccag ttattaagtc acgatttaaa cgtttcgtca acctacacgc    180
acgcggtttc tgctttcaaa cgcaccggtc acgcacggtt ccgccgtgga ccgtcgtcta    240
ccaccggaga cactaacgga ccttcaactt cttcacattc ggaaggtaaa tcacgagata    300
```

```
cgacttcgtt tgtacaaaac gagtgttttt caaacaaatc ggtgacggag ataacgacga    360
cgacgacgtc aacgagctcg tcgtctgtag tatcttcttc caccggtgga aacttagacg    420
gaagtgtttc aacggtaaaa cagttttctt cgttaggtat agtagctccg gcgccgacgt    480
tctcgtctag aaaaccaccg ttaccgtcga cacaccggaa aaggtgcggc gctgatcgtc    540
ctgttgcttc cgtacacgga tccggaagcg gttgccattg ttgttccaag agaaggaaaa    600
ccggatctaa acgtgaaatt agaagagttc cgattaccgg atctaaaatt acaagcatac    660
ctgctgatga ttactcatgg aaaaagtacg gcgagaagaa gatcgacggt tcactttatc    720
cacgagtata ttacaaatgt attaccggaa aaggatgtcc ggcgaggaag cgcgtggagt    780
taagcgccga cgattcgaag atgcttattg ttacttacga cggagaacac cgtcaccgtg    840
accgtcacgc gccggtacct atgagtttga ccggtgtgta tggtgagtca aagtgagggg    900
gacacatgtg tggtccgtga gcactttgca cagttttcta aggtcaacag gaagagagag    960
aaaataactt ttttattct tggtttagtt gagggttaat ttgtacattt gacaaaagat   1020
gaagggtgta attggtaatt tagaagatgc ccccagatct gatattcgat tttgtttgga   1080
ctaattactt tataaaagtt gatattggta tatttaaaat ttaattaaag aggaaaagta   1140
attagtccaa acaaaatcga atatcagatc tg                                 1172
```

<210> SEQ ID NO 4
<211> LENGTH: 267
<212> TYPE: PRT
<213> ORGANISM: Helianthus annuus

<400> SEQUENCE: 4

```
Met Ala Val Asp Phe Val Gly Ile Ser Thr Asp His Leu Leu Asn Arg
1               5                   10                  15

Met Phe Gln Leu Leu Ser His Asp Leu Asn Val Ser Ser Thr Tyr Thr
            20                  25                  30

His Ala Val Ser Ala Phe Lys Arg Thr Gly Ala Arg Phe Arg Arg Gly
        35                  40                  45

Pro Ser Ser Thr Thr Gly Asp Thr Asn Gly Pro Ser Thr Ser Ser His
    50                  55                  60

Ser Glu Gly Lys Ser Arg Asp Thr Thr Ser Phe Val Asn Glu Cys Phe
65                  70                  75                  80

Ser Asn Lys Ser Val Thr Glu Ile Thr Thr Thr Thr Ser Thr Ser
                85                  90                  95

Ser Ser Ser Val Val Ser Ser Ser Thr Gly Gly Asn Leu Asp Gly Ser
            100                 105                 110

Val Ser Asn Gly Lys Phe Ser Ser Leu Gly Ile Val Ala Pro Ala Pro
        115                 120                 125

Thr Phe Ser Ser Arg Lys Pro Pro Leu Pro Ser Thr His Arg Lys Arg
    130                 135                 140

Cys Gly Ala Asp Arg Pro Val Ala Ser Val His Gly Ser Gly Ser Gly
145                 150                 155                 160

Cys His Cys Cys Ser Lys Arg Arg Lys Thr Gly Ser Lys Arg Glu Ile
                165                 170                 175

Arg Arg Val Pro Ile Thr Gly Ser Lys Ile Thr Ser Ile Pro Ala Asp
            180                 185                 190

Asp Tyr Ser Trp Lys Lys Tyr Gly Glu Lys Lys Ile Asp Gly Ser Leu
        195                 200                 205

Tyr Pro Arg Val Tyr Tyr Lys Cys Ile Thr Gly Lys Gly Cys Pro Ala
    210                 215                 220
```

Arg Lys Arg Val Glu Leu Ser Ala Asp Asp Ser Lys Met Leu Ile Val
225                 230                 235                 240

Thr Tyr Asp Gly Glu His Arg His Arg Asp Arg His Ala Pro Val Pro
            245                 250                 255

Met Ser Leu Thr Gly Val Tyr Gly Glu Ser Lys
            260                 265

<210> SEQ ID NO 5
<211> LENGTH: 901
<212> TYPE: DNA
<213> ORGANISM: Helianthus annuus

<400> SEQUENCE: 5

```
cttggcgggg atcatctctc tttctctctc tctctcttag ggtttcaact tccaaccttc    60
ttctacaaca atggcggttg atttcgtcgg aattcaatct acagatcatc atctaaaccg   120
catgtttcag ttatcaactc acgatttaaa cgtttcgtca acctacacac acgcggtttc   180
tgctttcaaa cgcaccggtc acgcacggtt ccgccgtgga ccgtcgtcta ccaccggaga   240
cactaacgga ccttcaactt cttcacattg gaaggtaaa tcacgagata cgacgtcgtt   300
tgtacaaaac gagtgttttt caaacaaatc ggtgacggag ataacgacga cgacgacgtc   360
aacgagctcg tcgtctgtag tatcgtcttc caccggtgga aacttagacg gaagtgtttc   420
caacggtaaa cagtttttt cgttaggtat agtagctccg gcgccgacgt tctcgtctag   480
aaaaccaccg ctaccgtcga ctcatcggaa aaggtgcagc gctgatcgtc ctgttgcttc   540
cgtacacgga tctggaagcg gttgccattg ttgttccaag agaaggaaaa ccggatctaa   600
acgtgaaatt agaagagttc cgattaccgg atctaaaatt acaagcatac ctgctgatga   660
ttactcatgg aaaaagtacg gcgagaagaa gatcgacggt tcactttatc cacgagtgta   720
ttacaaatgt attaccggaa aaggatgtcc ggcgaggaag cgcgtggagt taagcgccga   780
cgattcgaag atgcttattg ttacttacga cggagaacac cgtcaccgtg accgtcacgt   840
gccggtactt atgagtttga ccggtgtgta tggtgagtca aagtgagggg gacacatgtg   900
t                                                                  901
```

<210> SEQ ID NO 6
<211> LENGTH: 267
<212> TYPE: PRT
<213> ORGANISM: Helianthus annuus

<400> SEQUENCE: 6

Met Ala Val Asp Phe Val Gly Ile Ser Thr Asp His His Leu Asn Arg
1               5                   10                  15

Met Phe Leu Ser Thr His Asp Leu Asn Val Ser Ser Thr Tyr Thr His
            20                  25                  30

Ala Val Ser Ala Phe Lys Arg Thr Gly His Ala Arg Phe Arg Arg Gly
        35                  40                  45

Pro Ser Ser Thr Thr Gly Asp Thr Asn Gly Pro Ser Thr Ser Ser His
    50                  55                  60

Ser Glu Gly Lys Ser Arg Asp Thr Thr Ser Phe Val Asn Glu Cys Phe
65                  70                  75                  80

Ser Asn Lys Ser Val Thr Glu Ile Thr Thr Thr Thr Ser Thr Ser
            85                  90                  95

Ser Ser Ser Val Val Ser Ser Ser Thr Gly Gly Asn Leu Asp Gly Ser
            100                 105                 110

| | | | | | | | | | | | |
|---|---|---|---|---|---|---|---|---|---|---|---|
|Val|Ser|Asn|Gly|Lys|Phe|Phe|Ser|Leu|Gly|Ile|Val|Ala|Pro|Ala|Pro|
| | |115| | | |120| | | |125| |

Val Ser Asn Gly Lys Phe Phe Ser Leu Gly Ile Val Ala Pro Ala Pro
          115                120               125

Thr Phe Ser Ser Arg Lys Pro Pro Leu Pro Ser Thr His Arg Lys Arg
    130                  135               140

Cys Ser Ala Asp Arg Pro Val Ala Ser Val His Gly Ser Gly Ser Gly
145               150               155              160

Cys His Cys Cys Ser Lys Arg Arg Lys Thr Gly Ser Lys Arg Glu Ile
        165                170            175

Arg Arg Val Pro Ile Thr Gly Ser Lys Ile Thr Ser Ile Pro Ala Asp
          180              185              190

Asp Tyr Ser Trp Lys Lys Tyr Gly Glu Lys Lys Ile Asp Gly Ser Leu
    195                200              205

Tyr Pro Arg Val Tyr Lys Cys Ile Thr Gly Lys Gly Cys Pro Ala
    210              215             220

Arg Lys Arg Val Glu Leu Ser Ala Asp Asp Ser Lys Met Leu Ile Val
225               230              235         240

Thr Tyr Asp Gly Glu His Arg His Arg Asp Arg His Val Pro Val Leu
        245                250            255

Met Ser Leu Thr Gly Val Tyr Gly Glu Ser Lys
    260                265

<210> SEQ ID NO 7
<211> LENGTH: 7
<212> TYPE: PRT
<213> ORGANISM: Helianthus annuus

<400> SEQUENCE: 7

Trp Lys Lys Tyr Gly Glu Lys
1             5

<210> SEQ ID NO 8
<211> LENGTH: 7
<212> TYPE: PRT
<213> ORGANISM: Helianthus annuus

<400> SEQUENCE: 8

Trp Arg Lys Tyr Gly Gln Lys
1             5

<210> SEQ ID NO 9
<211> LENGTH: 4454
<212> TYPE: DNA
<213> ORGANISM: Helianthus annuus

<400> SEQUENCE: 9

```
aatacaattg attactcagt cgaataatgg ccaatatccg ttcataatcg acgacgacgt      60
cactagggtt ttttctcttc cggttaccag gcctatcatc tggtttctgg tttattttga    120
gggtgagggt tttgcattga ttcctacgct ccaatcatct gcttcctgaa ttgaatctga    180
atctgaatct gaaagttaac tagacccctc aagttgtcat cgtaacaac taagcgtctg     240
gagattccaa gcattttatc gtgtgttgta attttaatga agcaatgaag attgaatatg    300
cactagggtg agggttttgc attgattcct gcgctccaat catctgcttc ctgaattgaa    360
tctgaatctg aaagttaact agacccctca agttgtcatt cgtaacaact aagcgtctgg    420
agaagagtat gttgatatag gagagttgaa cccgacacgt cttctgtgat gattcaaaac    480
attccgaata actagcagaa cccgatccac ttacattcga ataacgctga gaatccacaa    540
cgcttatggc cagattcttt ccttcaatct tggcaaaatc aatgcctgct tgttttatta    600
```

```
tcacgaaagt actgaacaac cgagataggc acaataacaa caacagcttt ccatgatttg      660
gagactgatc ggaatcgaat cagtgatttt actggaagcc gtttgattat gttttattat      720
cacgaaagta ctgaacaacc gagatagaca caataacaac acaactttc catgatttgg       780 agactgatca gaatcgaaac agtgatttta ctttactgga agccgtttga ttatttcctc      840
ttggatctcg aaaggcacgt tgtctgacat cttgattttg attaccaact caccatatca      900
atttctaggt agttaacaac gctaattaga aaaaaaacg tgattcatat acacaacggt       960
ctctttgctt cgtccactag aactatttgt gtatgcattc ttttggtagt taacaacgct     1020
aattagaaaa aaatctgtaa aattaatcat atcgattgct ataacaggat ggatgtgaca     1080
cacacagata gataagctgt cacagttgtc aagactgttt gtcgggtttc caatgctcac     1140
acagggtgat aaacaatgct gatacgaaca catgtgtttc gaaataggct tgttcttgg      1200 tttaatgaag ttacatgtaa catctactta tattcagatt taaacaatgc ccgcctcaac     1260
tgagataacg gacatccatc aagctcaaaa agaaaacttg tgtttcccat agtcacaaaa     1320
gattgcggtt tgtatttcgc atagccaccg tttccgtagt aaaaaacggt tgcggtttgt     1380
atttcgcata gccaccgttt ccgtagtaaa aaacggttgg gtttgcacat tcaatcttca     1440
atacttcatt aaaataccac tagtagaaga acccgacacg tcttcatgtt acggagaatg     1500
ttctacaaat tgaaggaaaa ggaaaagatt tgttgaaatc gaatttgaca actatgacag     1560
cttattaaaa gtagcaatca cctccaatca tttcctggtc aaatcacaca ccataaagtt     1620
taaagttatc gtgtgttgta gtttggaaag atgaccgaac aaagatctga ataacaaact     1680
gtggagaact tgtttgtgtc gggttcttct gctagttact tgatcaacgg actgatcgtt     1740
aacgttactc tacttgtgct ccgatttaag cggcgtgttc cgatcaacgt tgtttaaagg     1800
tgatgaagag tttagaaacc ctagaatgat ggtgctttta cgggaaaaaa cgtgataatt     1860 gaaaacatc aatctatacg gcctgtatac aattatacgg cccgtataca tttggtaaac      1920
atcaaaaacc tcccaaaata aatccattga gccgtatagt ttttacaaat cgtatacaca     1980
tgtatacggc tcgtataact atatacgggc cgtatatagt aaaaaaaaca ttctttacgc     2040
attgtcctat taaaaaacat tctatacgga ccgtatattt tgtatacggt ccgtataaac     2100
taaagatatg aaaatataat atagggggtg tgggaataag aggagcgtta ttaaaataca     2160
caaataattt tcgtcatgac tccaactaca tgttttattg tgttcttgtt tgtcgttatt     2220
aatattttct ttgacataga aagtcgaaac gcatggtatc cagctacgta cacatttatt     2280
caacttatat ttattttagt cctcgtttga ctttatgcct ccactagctt tctccatctg     2340
tttatcacgc tgcaaataag tcaaacaatt ctccaccgtc cgatcaaaac agtatctcat     2400
tgactccact ttcccaattg gacctttata accccttct acccctcata tctctcatca      2460
atctctcttt ctctctctta gggtttcaac ttccaacctt cttctacaac aatggcggtt     2520
gatttcgtcg gaattcaatc taccgatcat cttctaaacc gcatgttcca gttattaagt     2580
cacgatttaa acgtttcgtc aacctacacg cacgcggttt ctgctttcaa acgcaccggt     2640
cacgcacggt tccgccgtgg accgtcgtct accaccggag acactaacgg accttcaact     2700
tcttcacatt cggaaggtaa atcacgagat acgacttcgt tgtacaaaa cgagtgtttt      2760 tcaaacaaat cggtgacgga gataacgacg acgacgacgt caacgagctc gtcgtctgta     2820
gtatcttctt ccaccggtgg aaacttagac ggaagtgttt ccaacggtaa acagttttct     2880
tcgttaggta tagtagctcc ggcgccgacg ttctcgtcta gaaaaccacc gttaccgtcg     2940
```

```
acacaccgga aaaggtgcgg cgctgatcgt cctgttgctt ccgtacacgg atccggaagc    3000
ggttgccatt gttgttccaa gagaaggtgc gtatgcgctc tcggcgaacg ttagcaaatt    3060
tatgtactta ttatatatct tacgcctgtt ttcgtaaagt aaactaataa aaatatcttc    3120
cttttcgtgt attctctcag gaaaaccgga tctaaacgtg aaattagaag agttccgatt    3180
accggatcta aaattacaag catacctgct gatgattact catggaaaaa gtacggcgag    3240
aagaagatcg acggttcact ttatccacgg taattaatca cagtcttcat aaatttataa    3300
tatttataat tataattata attataatta taatttaatg gatttctgat ttagattcta    3360
atttgaaata tacagagtat attacaaatg tattaccgga aaaggatgtc cggcgaggaa    3420
gcgcgtggag ttaagcgccg acgattcgaa gatgcttatt gttacttacg acggagaaca    3480
ccgtcaccgt gaccgtcacg cgccggtacc tatgagtttg accggtgtgt atggtgagtc    3540
aaagtgaggg ggacacatgt gtggtccgtg agcactttgc acagttttct aaggtcaaca    3600
ggaagagaga gaaattaact tttttattc ttggtttagt tgagggttaa tttgtacatt    3660
tgacaaaaga tgaagggtgt aattggtaat ttagaagatg ccccagatct gatattcgat    3720 tttgttgga ctaattactt tataaaagtt gatattggta tatttaaaat ttaattaaag    3780
aggaaaagta atttgaataa gtttgatgcc acagcagagt caatgggttt taaagtctct    3840
ttaaatgact aaaaaattag ataattgaat gaattttta atggcaaatg tagtctttat    3900
tttcatattt attatggtcg ttggtgcgac ttttggcaaa ttgatttcga caatgtattg    3960
atggcgatga tctggaatgg tccaatccaa ttttttattt gttttattgt ttaatattta    4020
ggagactttg gaaaaatagc aagggttgac cctgatgaat attaataagt tgtgtttact    4080
aaagaagcaa gaatgtaaca gctagcgatg agatgttaac taacgggtac cgtattgatg    4140
tcgagctaaa accaaaacca aataacataa tgtgtatgtt cagttggtat tggtattata    4200
cggtaccgct aaaaatccca aacaggtaag tgccacatgg tatcgatact gcagcttaga    4260
taaaataaaa ttgaatatca caccgtatat gtttggtcga catcaataac aggtattcgg    4320
tatgaagttt cccatctcaa gactggcacg taatatcata tatatacaac tatagttggt    4380
tttatacttt cggagtttac ggtttcaact tctattagtt gggtgaagag catccaagag    4440
gtcatcaatc tgta                                                      4454
```

<210> SEQ ID NO 10
<211> LENGTH: 2511
<212> TYPE: DNA
<213> ORGANISM: Helianthus annuus

<400> SEQUENCE: 10

```
aatacaattg attactcagt cgaataatgg ccaatatccg ttcataatcg acgacgacgt      60
cactagggtt ttttctcttc cggttaccag gcctatcatc tggtttctgg tttattttga    120
gggtgagggt tttgcattga ttcctacgct ccaatcatct gcttcctgaa ttgaatctga    180
atctgaatct gaaagttaac tagacccctc aagttgtcat tcgtaacaac taagcgtctg    240
gagattccaa gcattttatc gtgtgttgta attttaatga agcaatgaag attgaatatg    300
cactagggtg agggttttgc attgattcct gcgctccaat catctgcttc ctgaattgaa    360
tctgaatctg aaagttaact agacccctca agttgtcatt cgtaacaact aagcgtctgg    420
agaagagtat gttgatatag gagagttgaa cccgacacgt cttctgtgat gattcaaaac    480
attccgaata actagcagaa cccgatccac ttacattcga ataacgctga gaatccacaa    540
cgcttatggc cagattcttt ccttcaatct tggcaaaatc aatgcctgct tgttttatta    600
```

```
tcacgaaagt actgaacaac cgagataggc acaataacaa caacagcttt ccatgatttg      660
gagactgatc ggaatcgaat cagtgatttt actggaagcc gtttgattat gttttattat      720
cacgaaagta ctgaacaacc gagatagaca caataacaac aacaactttc catgatttgg      780
agactgatca gaatcgaaac agtgatttta ctttactgga agccgtttga ttatttcctc      840
ttggatctcg aaaggcacgt tgtctgacat cttgattttg attaccaact caccatatca      900
atttctaggt agtaacaac gctaattaga aaaaaaacg tgattcatat acacaacggt       960
ctctttgctt cgtccactag aactatttgt gtatgcattc ttttggtagt taacaacgct     1020
aattagaaaa aaatctgtaa aattaatcat atcgattgct ataacaggat ggatgtgaca     1080
cacacagata gataagctgt cacagttgtc aagactgttt gtcgggtttc caatgctcac     1140
acagggtgat aaacaatgct gatacgaaca catgtgtttc gaataggct tgttcttgg      1200 tttaatgaag ttacatgtaa catctactta tattcagatt taaacaatgc ccgcctcaac     1260
tgagataacg gacatccatc aagctcaaaa agaaaacttg tgtttcccat agtcacaaaa     1320
gattgcggtt tgtatttcgc atagccaccg tttccgtagt aaaaaacggt tgcggtttgt     1380
atttcgcata gccaccgttt ccgtagtaaa aaacggttgg gtttgcacat tcaatcttca     1440
atacttcatt aaaataccac tagtagaaga acccgacacg tcttcatgtt acggagaatg     1500
ttctacaaat tgaaggaaaa ggaaaagatt tgttgaaatc gaatttgaca actatgacag     1560
cttattaaaa gtagcaatca cctccaatca tttcctggtc aaatcacaca ccataaagtt     1620
taaagttatc gtgtgttgta gtttggaaag atgaccgaac aaagatctga ataacaaact     1680
gtggagaact tgtttgtgtc gggttcttct gctagttact tgatcaacgg actgatcgtt     1740
aacgttactc tacttgtgct ccgatttaag cggcgtgttc cgatcaacgt tgtttaaagg     1800
tgatgaagag tttagaaacc ctagaatgat ggtgctttta cgggaaaaaa cgtgataatt     1860
gaaaaacatc aatctatacg gcctgtatac aattatacgg cccgtataca tttggtaaac     1920
atcaaaaacc tcccaaaata aatccattga gccgtatagt ttttacaaat cgtatacaca     1980
tgtatacggc tcgtataact atatacgggc cgtatatagt aaaaaaaaca ttctttacgc     2040
attgtcctat taaaaaacat tctatacgga ccgtatattt tgtatacggt ccgtataaac     2100
taaagatatg aaaataaaat ataggggtg tgggaataag aggagcgtta ttaaaataca     2160
caaataattt tcgtcatgac tccaactaca tgttttattg tgttcttgtt tgtcgttatt     2220
aatattttct ttgacataga aagtcgaaac gcatggtatc cagctacgta cacatttatt     2280
caacttatat ttattttagt cctcgtttga ctttatgcct ccactagctt tctccatctg     2340
tttatcacgc tgcaaataag tcaaacaatt ctccaccgtc cgatcaaaac agtatctcat     2400
tgactccact ttcccaattg gacctttata accccttct acccctcata tctctcatca     2460
atctctcttt ctctctctta gggtttcaac ttccaacctt cttctacaac a              2511
```

<210> SEQ ID NO 11
<211> LENGTH: 817
<212> TYPE: DNA
<213> ORGANISM: Helianthus annuus

<400> SEQUENCE: 11

```
atggcggttg atttcgtcgg aattcaatct accgatcatc ttctaaaccg catgttccag       60
ttattaagtc acgatttaaa cgtttcgtca acctacacgc acgcggtttc tgctttcaaa      120
cgcaccggtc acgcacggtt ccgccgtgga ccgtcgtcta ccaccggaga cactaacgga      180
```

```
ccttcaactt cttcacattc ggaaggtaaa tcacgagatg cgacttcgtt tgtacaaaac    240
gagtgttttt caaacaaacc ggtgacggag ataacgacga cgacgacgtc aacgagctcg    300
tcgtctgtag tatcgtcttc caccggtgga aacttagacg gaagtgtttc caacggtaaa    360
cagttttctt cgttaggtat agtagctccg gcgccgacgt tctcgtctag aaaaccaccg    420
ttaccgtcga cacaccggaa aaggtgcggc gctgatcgtc ctgttgcttc cgtcacggca    480
tccggaagcg gttgccattg ttgttccaag agaaggaaaa ccggatctaa acgtgaaatt    540
agaagagttc cgattaccgg atctaaaatt acaagcatac ctgctgatga ttactcatgg    600
aaaaagtacg gcgagaagaa gatcgacggt tcactttatc cacgagtata ttacaaatgt    660
attaccggaa aaggatgtcc ggcgaggaag cgcgtggagt taagcgccga cgattcgaag    720
atgcttattg ttacttacga cggagaacac cgtcaccgtg accgtcacgc gccggtacct    780
atgagtttga ccggtgtgta tggtgagcca aagtgaa                            817
```

<210> SEQ ID NO 12
<211> LENGTH: 271
<212> TYPE: PRT
<213> ORGANISM: Helianthus annuus

<400> SEQUENCE: 12

```
Met Ala Val Asp Phe Val Gly Ile Gln Ser Thr Asp His Leu Leu Asn
1               5                   10                  15

Arg Met Phe Gln Leu Leu Ser His Asp Leu Asn Val Ser Ser Thr Tyr
            20                  25                  30

Thr His Ala Val Ser Ala Phe Lys Arg Thr Gly His Ala Arg Phe Arg
        35                  40                  45

Arg Gly Pro Ser Ser Thr Thr Gly Asp Thr Asn Gly Pro Ser Thr Ser
    50                  55                  60

Ser His Ser Glu Gly Lys Ser Arg Asp Ala Thr Ser Phe Val Gln Asn
65                  70                  75                  80

Glu Cys Phe Ser Asn Lys Pro Val Thr Glu Ile Thr Thr Thr Thr Thr
                85                  90                  95

Ser Thr Ser Ser Ser Ser Val Val Ser Ser Ser Thr Gly Gly Asn Leu
            100                 105                 110

Asp Gly Ser Val Ser Asn Gly Lys Gln Phe Ser Ser Leu Gly Ile Val
        115                 120                 125

Ala Pro Ala Pro Thr Phe Ser Ser Arg Lys Pro Pro Leu Pro Ser Thr
    130                 135                 140

His Arg Lys Arg Cys Gly Ala Asp Arg Pro Val Ala Ser Val His Gly
145                 150                 155                 160

Ser Gly Ser Gly Cys His Cys Cys Ser Lys Arg Arg Lys Thr Gly Ser
                165                 170                 175

Lys Arg Glu Ile Arg Arg Val Pro Ile Thr Gly Ser Lys Ile Thr Ser
            180                 185                 190

Ile Pro Ala Asp Asp Tyr Ser Trp Lys Lys Tyr Gly Glu Lys Lys Ile
        195                 200                 205

Asp Gly Ser Leu Tyr Pro Arg Val Tyr Tyr Lys Cys Ile Thr Gly Lys
    210                 215                 220

Gly Cys Pro Ala Arg Lys Arg Val Glu Leu Ser Ala Asp Asp Ser Lys
225                 230                 235                 240
```

```
Met Leu Ile Val Thr Tyr Asp Gly Glu His Arg His Arg Asp Arg His
                245                 250                 255
Ala Pro Val Pro Met Ser Leu Thr Gly Val Tyr Gly Glu Pro Lys
                260                 265                 270
```